US009056906B2

(12) United States Patent
Koenig et al.

(10) Patent No.: US 9,056,906 B2
(45) Date of Patent: Jun. 16, 2015

(54) METHODS FOR THE TREATMENT OF AUTOIMMUNE DISORDERS USING IMMUNOSUPPRESSIVE MONOCLONAL ANTIBODIES WITH REDUCED TOXICITY

(75) Inventors: Scott Koenig, Rockville, MD (US);
Ronald L. Wilder, Rockville, MD (US);
Ezio Bonvini, Rockville, MD (US);
Leslie S. Johnson, Darnestown, MD (US)

(73) Assignee: MACROGENICS, INC., Rockville, MD (US)

( * ) Notice: Subject to any disclaimer, the term of this patent is extended or adjusted under 35 U.S.C. 154(b) by 426 days.

(21) Appl. No.: 11/763,434

(22) Filed: Jun. 14, 2007

(65) Prior Publication Data

US 2008/0095766 A1 Apr. 24, 2008

Related U.S. Application Data

(60) Provisional application No. 60/813,903, filed on Jun. 14, 2006, provisional application No. 60/871,361, filed on Dec. 21, 2006.

(51) Int. Cl.
*A61K 39/395* (2006.01)
*A61K 39/40* (2006.01)
*C07K 16/28* (2006.01)
*C07K 16/00* (2006.01)
*A61K 39/00* (2006.01)

(52) U.S. Cl.
CPC ....... *C07K 16/2809* (2013.01); *A61K 2039/505* (2013.01); *A61K 2039/545* (2013.01); *C07K 2317/41* (2013.01); *C07K 2317/71* (2013.01)

(58) Field of Classification Search
None
See application file for complete search history.

(56) References Cited

U.S. PATENT DOCUMENTS

| 4,079,126 | A | 3/1978 | Homma et al. |
|---|---|---|---|
| 4,221,794 | A | 9/1980 | Simon et al. |
| 4,361,549 | A | 11/1982 | Kung et al. |
| 4,515,893 | A | 5/1985 | Kung et al. |
| 4,658,019 | A | 4/1987 | Kung et al. |
| 4,695,624 | A | 9/1987 | Marburg et al. |
| 4,830,852 | A | 5/1989 | Marburg et al. |
| 4,882,317 | A | 11/1989 | Marburg et al. |
| 4,882,424 | A | 11/1989 | Schlossman et al. |
| 5,078,998 | A | 1/1992 | Bevan et al. |
| 5,585,089 | A | 12/1996 | Queen et al. |
| 5,624,821 | A | 4/1997 | Winter et al. |
| 5,885,573 | A | 3/1999 | Bluestone et al. |
| 6,113,901 | A | 9/2000 | Bluestone et al. |
| 6,143,297 | A | 11/2000 | Bluestone et al. |
| 6,406,696 | B1 | 6/2002 | Bluestone et al. |
| 6,491,916 | B1 | 12/2002 | Bluestone et al. |
| 7,041,289 | B1 | 5/2006 | Bach et al. |
| 2003/0108548 | A1 | 6/2003 | Bluestone et al. |
| 2003/0216551 | A1 | 11/2003 | Delovitch |
| 2005/0037000 | A1 | 2/2005 | Stavenhagen |
| 2005/0064514 | A1 | 3/2005 | Stavenhagen |
| 2005/0196395 | A1 | 9/2005 | Weiner et al. |
| 2006/0002933 | A1 | 1/2006 | Zivin et al. |
| 2006/0078557 | A1 | 4/2006 | Bluestone et al. |
| 2006/0177896 | A1 | 8/2006 | Mach et al. |
| 2006/0188494 | A1 | 8/2006 | Bach et al. |
| 2006/0292142 | A1 | 12/2006 | Bluestone et al. |
| 2007/0077246 | A1 | 4/2007 | Koenig et al. |
| 2007/0190045 | A1 | 8/2007 | Herold et al. |
| 2008/0095766 | A1* | 4/2008 | Koenig et al. ............. 424/133.1 |

FOREIGN PATENT DOCUMENTS

| EP | 0440373 | 1/1991 |
|---|---|---|
| EP | 0497883 | 8/1992 |
| EP | 0613944 | 9/1994 |
| JP | 60-248622 | 12/1985 |
| WO | WO 90/05541 | 5/1990 |
| WO | WO 91/01143 | 2/1991 |
| WO | WO 91/04053 | 4/1991 |
| WO | WO 91/09966 | 7/1991 |
| WO | WO 91/09968 | 7/1991 |

(Continued)

OTHER PUBLICATIONS

Dugdale. Medline Plus. May 3, 2009. pp. 1-3.*
Sherry et al. The Lancet Aug. 6, 2011, vol. 378;pp. 487-497.*
Aletaha et al. Ann. Rheum Dis 2010;69:1580-1588.*
Bardwell et al., 2002, Rheumatology 41:38-45.*
Adair et al., "Humanization of the Murine Anti-Human CD3 Monoclonal Antibody OKT3," Hum. Antibodies Hybridomas, 5(1):41-47, 1994.
Alegre et al., "A Non-Activating "Humanized" Anti-CD3 Monoclonal Antibody Retains Immunosuppressive Properties In Vivo," Transplantation, 57(11):1537-1543,1994.
Alegre et al., "Cytokine Release Syndrome Induced by the 145-2C11 Anti-CD3 Monoclonal Antibody in Mice: Prevention by High Doses of Methylprednisolone," The Journal of Immunology, 146(4):1184-1191,1991.
Alegre et al., "Effect of a Single Amino Acid Mutation in the Fc Portion of a "Humanized" OKT3 on T Cell Responses In Vitro," J. Am. Soc. Nephol., 2(3):1991.

(Continued)

*Primary Examiner* — Chun Dahle
(74) *Attorney, Agent, or Firm* — Margaret B. Brivanlou; Nicole Fortune; King & Spalding LLP

(57) ABSTRACT

The present invention provides methods of treating, preventing, slowing the progression of, or ameliorating the symptoms of T cell mediated immunological diseases, particularly autoimmune diseases (e.g., autoimmune diabetes (i.e. type 1 diabetes or insulin-dependent diabetes mellitus (IDDM)) and multiple sclerosis) through the use of anti-human CD3 antibodies. The antibodies of the invention of the invention are preferably used in low dose dosing regimens, chronic dosing regimens or regimens that involve redosing after a certain period of time. The methods of the invention provide for administration of antibodies that specifically bind the epsilon subunit within the human CD3 complex. Such antibodies modulate the T cell receptor/alloantigen interaction and, thus, regulate the T cell mediated cytotoxicity associated with autoimmune disorders. Additionally, the methods of the invention provide for use of anti-human CD3 antibodies modified such that they exhibit reduced or eliminated effector function and T cell activation as compared to non-modified anti-human CD3 antibodies.

8 Claims, 5 Drawing Sheets

(56) References Cited

FOREIGN PATENT DOCUMENTS

Figure 3:
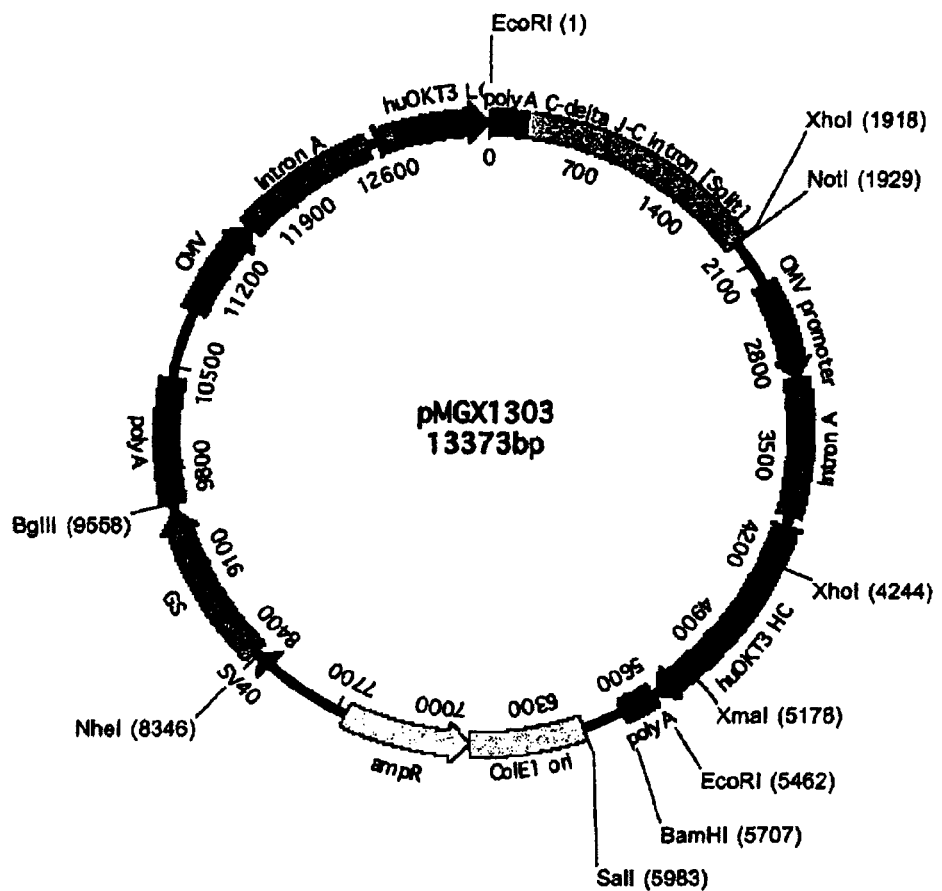

| WO | WO 92/00092 | 1/1992 |
|---|---|---|
| WO | WO 92/15671 | 9/1992 |
| WO | WO 93/00431 | 1/1993 |
| WO | WO 93/19196 | 9/1993 |
| WO | WO 93/19767 | 10/1993 |
| WO | WO 93/25712 | 12/1993 |
| WO | WO 94/23760 | 1/1994 |
| WO | WO 94/28912 | 12/1994 |
| WO | WO 95/03408 | 2/1995 |
| WO | WO 98/47531 | 10/1998 |
| WO | WO 01/25398 | 4/2001 |
| WO | WO 03/026692 | 4/2003 |
| WO | WO 03/102132 | 12/2003 |
| WO | WO 2007/009064 | 1/2007 |
| WO | WO 2007/117600 | 10/2007 |
| WO | WO 2007/145941 | 12/2007 |
| WO | WO 2008/079713 | 7/2008 |

OTHER PUBLICATIONS

Alegre et al., "Effect of a Single Amino Acid Mutation on the Activating and Immunosuppressive Properties of a "Humanized" OKT3 Monoclonal Antibody," The Journal of Immunology, 148(11):3461-3468, 1992.

Alegre et al., "An Anti-Murine CD3 Monoclonal Antibody with a Low Affinity for Fcγ Receptors Supresses Transplantation Responses While Minimizing Acute Toxicity and Immunogenicity" Journal of Immunology, 1544-1554, AUQ 1995.

Archer et al., "Inverse Relationship Between Immune Interferon Induction and Mitogen Effects on the Maturation of the Primary Antibody Response," Immunopharmacology, 3:71-81, 1981.

Aruffo, A. and Seed, B., "Molecular Cloning of a CD28 cDNA by a High-Efficiency COS Cell Expression System," Proc Natl. Acad. Sci. USA, 84:8573-8577, 1987.

Azuma et al., "Involvement of CD28 in MHC-Unrestricted Cytotoxicity Mediated by a Human Natural Killer Leukemia Cell Line," The Journal of Immunology,149:1115-1123,1992.

Azuma, M., et al., "B70 Antigen is a Second Ligand for CTLA-4 and CD28," Nature, 366:76-79, 1993.

Beyers et al, "Activation of T Lymphocytes via Monoclonal Antibodies Against Rat Cell Surface Antigens with Particular Reference to CD2 Antigen," Immunological Reviews, (111):59-77, 1989.

Bierer and Burakoff, "T-Lymphocyte Activation: The Biology and Function of CD2 and CD4," Immunological Reviews, (111):267-293,1989.

Bluestone, J., Hirsch, R., and Ellenhorn J., "In Vivo Administration of Monoclonal Anti-T Cell Antibodies Can Activate Immune Responses and Prevent Malignant Progressive Tumor Growth." Presented at U.S. Japan Cooperative Program in Cancer Research, Honolulu, Hawaii (Jan. 1989).

Bolt et al, "The Generation of a Humanized, Non-mitogenic CD3 Monoclonal Antibody Which Retains in vitro Immunosuppressive Properties,"Eur. J. Immunol., 23:403-411,1993.

Boussiotis et al., "B7 But Not Intercellular Adhesion Molecule-1 Costimulation Prevents the Induction of Human Alloantigen-Specific Tolerance," J. Exp. Med., 178:1753-1763,1993.

Boussiotis, V., et al., "Activated Human B Lymphocytes Express Three CTLA-4 Counterreceptors That Costimulate T-cell activation," Proc. Natl.. Acad. Sci, USA, 90:11059-11063,1993.

Bruce et al., "Enhanced humoral response to HIV-peptidic antigen with coadministration of lowdose anti-CD3 monoclonal antibody in mice," abstract for the Joint Meeting of the American Society for Biochemistry and Molecular Biology and the American Association of Immunologists, New Orleans, LA, Jun. 4-7, 1990, FASEB, 4(7):A2015, 1990.

Burton, "Immunoglobin G: Functional Sites," Molecular Immunology, 22(3):161-206, 1985.

Canfield et al., "The Binding Affinity of Human IgG for its High Affinity Fc Receptor Is Determined by Multiple Amino Acids in the CH2 Domain and Is Modulated by the Hinge Region," J. Exp. Med, 173: 1483-1491 (1991).

Carayanniotis and Barber, "Adjuvant-free IgG Responses Induced with Antigen Coupled to Antibodies Against Class II MHC," Nature, 327:59-61, 1987.

Ceuppens et al., "Failures of OKT3 Monoclonal Antibody to Induce Lymphocyte Mitogenesis: A Familial Defect in Monocyte Helper Function," The Journal of Immunology, 134(3): 1498-1502 (1985).

Ceuppens et al.,"T Cell Unresponsiveness to the Mitogenic Activity of OKT3 Antibody Results from a Deficiency of Monocyte Fcγ Receptors for Murine IgG2a and Inability to Cross-Link the T3-Ti Complex," The Journal of Immunology, 135(6) 3882-3886 (1985).

Chang et al., "Does OKT3 Monoclonal Antibody React with an Antigen-Recognition Structure on Human T Cells?" Proc. Natl. Acad. Sci. USA, 78(3):1805-1808, 1981.

Chappel et al., "Identification of a Secondary FcγRI Binding Site within a Genetically Engineered Human IgG Antibody," The Journal of Biological Chemistry, 268(33): 251 24-25131 (1993).

Chappel et al., "Identification of the Fcγ receptor class I binding site in human IgG through the use of recombinant IgG1/IgG2 hybrid and point-mutilated antibodies," Proc. Natl. Acad Sci. USA, 88: 9036-9040 (1991).

Chatenoud et al., "Systemic Reaction to the Anti-T-Cell Monoclonal Antibody OKT3 in Relation to Serum Levels of Tumor Necrosis Factor and Interferon-α," The New England Journal of Medicine, 320(21):1420-1421, 1989.

Chatenoud et al., "Anti-CD3 antibody induces long-term remission of overt autoimmunity in nonobese diabetic mice," Proc. Nat!. Acad. Sci. USA, 91: 123-128 (1994).

Chen et al., "Costimulation of T Cells for Tumor Immunity," Immunology Today, 14(10):483-486,1993.

Choi I et aL, "Recombinant chimeric OKT3 scFv IgM antibodies mediate immune suppression while reducing T cell activation in vitro," Eur. J. Immunol. ,vol. 31(3), pp. 94-106.

Cole et al., "Human IgG2 variants of chimeric anti-CD3 are nonmitogenic to T cells," J. Immunol., 159:3613-3621,1997.

Cosimi et al., "Prolonged Survival of Nonhuman Primate Renal Allograft Recipients Treated Only with Anti-CD4 Monoclonal Antibody," Surgery,108(2):406-414, 1990.

Danbolt et al., "Purification and Reconstitution of the Sodium- and Potassium-Coupled Glutamate Transport Glycoprotein from Rat Brain," Biochemistry, 29:6734-6740, 1990.

DeVries et al., "Interplay between the TCR/CD3 Complex and CD4 or CD8 in the Activation of Cytotoxic T Lymphocytes," Immunological Reviews, 109:119-141, 1989.

Duncan et al., "Localization of the binding site for the human high-affinity Fc receptor on IgG," Nature, 332:563-564, 1988.

Emmrich et al., "Cross-linking of the T cell Receptor Complex with the Subset-Specific Differentiation Antigen Stimulates Interleukin 2 Receptor Expression in Human CD4 and CD8 T Cells," Eur. J. Immunol., 17:529-534, 1987.

Flens et al., "Efficient Expansion of Tumor-Infiltrating Lymphocytes from Solid Tumors by Stimulation with Combined CD3 and CD28 Monoclonal Antibodies," Cancer Immunol. Immunother., 37:323-328,1993.

Fraser, J.D., et al., "Regulation of Interleukin-2 Gene Enhancer Activity by the T Cell Accessory Molecule CD28," Science, pp. 313-316, Jan. 18, 1991.

Freedman, A.S., et al, "Selective Induction of B7/BB-1 on Interferon-g Stimulated Monocytes: A Potential Mechanism for Amplification of T Cell Activation Through the CD28 Pathway," Cellular Immunology, 137:429-437,1991.

Freeman, G.J., et al., "Cloning of B7-2: A CTLA-4 Counter-Receptor That Costimulates Human T Cell Proliferation," Science, 262:909-911, 1993.

Freeman, G.J., et al., "Murine B7-2, an Alternative CTLA4 Counter-receptor That Costimulates T Cell Proliferation and Interleukin 2 Production," The Journal of Experimental Medicine, 178:2185-2192,1993.

Freeman, G.J., et al., "Uncovering of Functional Alternative CTLA-4 Counter-Receptor in B7-Deficient Mice," Science, 262:907-909,1993.

Friend P Jet al, "Phase I study of an engineered aglycosylated humanised CD3 antibody in renal transplant rejection," Transplantation, 1999, vol. 68( II}, pp. 1625-1626.

(56) References Cited

OTHER PUBLICATIONS

Gabizon et al., "Effect of Liposome Composition and Other Factors on the Targeting of Liposomes to Experimental Tumors: Biodistribution and Imaging Studies," Cancer Research, 50:6371-6378,1990.

Geppert et al., "Accessory Cell Independent Proliferation of Human T4 Cells Stimulated by Immobilized Monoclonal Antibodies to CD3," J. Immunol., 1987, 138(6):1660-1666.

Gergely and Sarmay, "The two binding-site models of human IgG binding Fcg receptors," The FASEB Journal, 4:3275-3283, 1990.

Gimmi, C.D., et al., "B-cell Surface Anigen B7 Provides a Costimulatory Signal That Induces T Cells to Proliferate and Secrete Interleuldn 2," Proc. Natl. Acad, Sci, USA, 88:6575-6579, 1991.

Gosselin et al., "The Monoclonal Antibody 41 H16 Detects the Leu 4 Responder Form of Human FcγRII," The Journal of Immunology, 144: 1817-1822 (1990).

Greenwood et a/., "Structural motifs involved in human IgG antibody effector functions," European Journal of Immunology, 23: 1098-1104 (1993).

Gross, J.A., et al., "Identification and Distribution of the Costimulatory Receptor CD28 in the Mouse," The Journal of Immunology,149:380-388,1992.

Guerder, S., et al., "Costimulator B7-1 Confers Antigen-Presenting-Cell Function to Parenchymal Tissue and in Conjunction with Tumor Necrosis Factor a Leads to Autoimmunity in Transgenic Mice," Proc. Natl. Acad. Sci. USA, 91:5138-5142,1994.

Harding and Allison, "CD28-B7 Interactions Allow the Induction of $CDB^+$ Cytotoxic T Lymphocytes in the Absence of Exogenous Help," J. Exp. Med., 177:1791-1796, 1993.

Harding, F.A., et al., "CD28-Mediated Signalling Co-Stimulates Murine T Cells and Prevents Induction of Anergy in T-cell Clones," Nature, 356:607-609, 1992.

Harlow and Lane, "Storing and Purifying Antibodies," Antibodies A Laboratory Manual, 284-287,1988.

Harper, K., et al, "CTLA-4 and CD28 Activated Lymphocyte Molecules Are Closely related in Both Mouse and Human as to Sequence, Message Expression, Gene Structure, and Chromosomal Location," The Journal of Immunology, 147:1037-1044,1991.

Harris et al., "Therapeutic Antibodies—the Coming of Age," Tiblech, 1993, 11:42-44, Feb. 1993.

Havran et al., "Expression and Function of the CD3-Antigen Receptor on Murine $CD4^+8^+$ Thymocytes," Nature, 330(12):170-173,1987.

Heath, W.R, et al., "Autoimmune Diabetes as a Consequence of Locally Produced Interleuldn-2," Nature, 359:547-549,1992.

Hering Bernhard J. et al., "Transplantation of cultured islets from two-layer preserved pancreases in type 1 diabetes with anti-CD3 antibody," American Journal of Transplantation, 2004, vol. 4(3), pp. 390-401.

Herold et al., "Prevention of Autoimmune Diabetes with Nonactivating Anti-CD3 Monoclonal Antibody," Diabetes, 41: 385-391 (1992).

Herold et al "Treatment of Type 1 Diabetes with Anti-CD3 Monoclonal Antibody," Immunologic Research, 28(2):141-150 (2000).

Herold Kevan C et al., A single course of anti-CD3 monoclonal antibody hOKT3y1 (Ala-Ala) results in improvement in C-Peptide responses and clinical parameters for at least 2 years after onset of type 1 diabetes., Diabetes, 2005, vol. 54, pp. 1763-1769.

Herold Kevan C et al., "Activation of human T cells by FcR nonbinding anti-CD3 mAb, hOKT3gammal(Ala-Ala)," J. Clin. Invest, 2003, vol. 111(3), pp. 409-418.

Herold Kevan C et al., "Anti-CD3 monoclonal antibody in new-onset type I diabetes mellitus," N. Engl. J. Med., 2002, vol. 346(22), pp. 1692-1698.

Hirsch et al., "Anti-CD3 F(ab')2 Fragments are Immunosuppressive In Vivo Without Evoking Either the Strong Humoral Response or Morbidity Associated with Whole mAb," Transplantation, 49(6): 1117-1123 (1990).

Jackson et al., "A monoclonal antibody to human brain-type creatine kinase," Biochem, J, 215: 505-512 (1983).

Janeway, "The T Cell Receptor as a Multicomponent Signalling Machine: CD4/CD8 Coreceptors and CD45 in T Cell Activation," Annu. Rev. Immunol., 10:645-74, 1992.

Jefferis et al., "Molecular Definition of Interaction Sites on Human IgG for Fc Receptors (huFcgR)," Molecular Immunology, 27(12):1237-1240, 1990.

Jenkins, M.K., et al., "CD28 Delivers a Costimulatory Signal Involved in Antigen-specific IL-2 Production by Human T Cells," The Journal of Immunology, 147:2461-2466, 1991.

Jenkins, M.K., et al., "Induction and Maintenance of Anergy in Mature T Cells," Advances in Experimental Medicine and Biology, 292:167-176, 1991.

Jolliffe, Linda K., "Humanized Antibodies: Enhancing Therapeutic Utility Through Antibody Engineering," Intern. Rev. Immunol. ,10:241-250,1993.

June, C.H., et al., "The B7 and CD28 Receptor Families," Immunol. Today, 15(7):321-331, 1994.

Keymeulen et aI., "Insulin needs after CD3-antibody therapy in new-onset type I diabetes," N Engl!. J Med, 2005, vol. 352(25), pp. 2598-2608.

Lenschow, D.J., et al., "Expression and Functional Significance of an additional Ligand for CTLA-4," Proc. Natl. Acad. Sci. USA, 90:11054-11058,1993.

Lenschow, D.J., et at, "Long-Tern Survival of Xenogeneic Pancreatic Islet Grafts Induced by CTLA4Ig," Science, 257:789-792,1992.

Li et al., "Costimulation of Tumor-Reactive $CD4^+$ and $CD8^+$ T Lymphocytes by B7, a Natural Ligand for CD38, Can Be Used to Treat Established Mouse Melanoma," The Journal of Immunology, 421-428, Jul. 1994.

Lin et al., "Long-Term Acceptance of Major Histocompatibility Complex Mismatched Cardiac Allografts Induced by CTLA4Ig Plus Donor-specific Transfusion," J. Exp. Med,178:1801-1806, Nov. 1993.

Lindsten, T., et al., "Characterization of CTLA-4 Structure and Expression on Human T Cells," The Journal of Immunology, 151:3489-3499,1993.

Lindsten, T., et al., "Regulation of Lymphokine Messenger RNA Stability by a Surface-Mediated T Cell Activation Pathway," Science, 244:339-343, 1989.

Linsley, P.S., et al, "CTLA-4 is a Second Receptor for the B Cell Activation Antigen B7," J. Exp. Med., 174:561-569,1991.

Liu and Linsley, "Costimulation of T-cell Growth," Current Opinion in Immunology, 4:265-270, 1992.

Looney et al., "Human Monocytes and U937 Cells Bear Two Distinct Fc Receptors for IgG," The Journal of Immunology, 136(5) 1641-1647 (1986).

Lund et al., "Human FcγRI and FcγRlIInteract with Distinct But Overlapping Sites on Human IgG," The Journal of Immunology, 147(8) 2657-2662 (1991).

Lund et al., "Multiple Binding Sites on the CH2 Domain of IgG for Mouse FcγRII," Molecular Immunology, 29(1): 53-39 (1991).

Maino et al., "Mechanism of THY-1-Mediated T Cell Activation: Roles of Fc Receptors, T200, la, and H-2 Glycoproteins in Accessory Cell Function," The Journal of Immunology, 126(5): 1829-1836 (1981).

Male et al., Advanced Immunology, pp. 11.8-11.9, Gower Medical Publishing, London, England, H. Hadjidimitriadou, ed., 1987.

Mannik, M. and Person R, "New antigenic determinants revealed on human IgG by binding two immunoblotting membranes," Journal of immunological Methods, 144:265-267,1991.

Morrison et al., "Recombinant Chimeric Monoclonal Antibodies," (1990).

Newell et al., "Death of Mature T Cells by Separate Ligation fo CD4 and the T-Cell Receptor for Antigen," Nature, 347:286-289,1990.

Newell et al., "In vivo TCR-mediated and T cell activation results in immunopotentiation and tumor regression," abstract for the Joint Meeting of the American Society for Biochemistry and Molecular Biology and the American Association of Immunologists, New Orleans, LA, Jun. 4-7, 1990, FASEB, 4(7):A2022,1990.

Nickoloff, B.J., et al., "Discordant Expression of CD28 Ligands, BB-1, and B7 on Keratinocytes in Vitro and Psoriatic Cells in Vivo," American Journal of Pathology, 142(4):1029-1040, 1993.

(56) References Cited

OTHER PUBLICATIONS

Ortho Multicenter Transplant Study Group, "A Randomized Clinical Trial of OKT3 Monoclonal Antibody for Acute Rejection of Gadaveric Renal Transplants," The New England Journal of Medicine, 313(6):337-342,1985.
Parlevliet et al., "Anti-CD3 Murine Monoclonal Isotype Switch Variants Tested for Toxicity and Immunologic Monitoring in Four Chimpanzees," Brief Communications, 50(5):889-892, 1990.
Parren et al., "Characterization of IgG FcR-Mediated Proliferation of Human T Cells Induced by Mouse and Human Anti-CD3 Monoclonal Antibodies: Identification of a Functional Polymorphism to Human IgG2 Anti-CD3," The Journal ofimmunoflV, 148(3): 695-701 (1992).
Partridge et al., "The Use of Anti-IgG Monoclonal Antibodies in Mapping the Monocyte Receptor Site in IgG," Molecular Immunology, 23(12):1365-1372, 1986.
PCT International Search Report mailed Nov. 2, 1994, pp. 1-8.
PCT International Search Report Dated Dec. 28, 2007, pp. 1-11.
Raasveld et al., "Complement activation during OKT3 treatment: A possible explanation for respiratory side effects," Kidney International, 43: 1140-1149 (1993).
Rao et al., "OKT3E, An Anti-CD3 Antibody That Does Not Elicit Side Effects or Antildiotype Responses in Chimpanzees," Transplantation, 52(4): 691-697 (1991).
Ravetch et al., "Fc Receptors," Annu. Rev. Immunol. 9: 457-492 (1991).
Razi-Wolf, et al, "Expression and Function of the Murine B7 Antigen, the Major Costimulatory Molecule Expressed by Peritoneal Exudate Cells," Proc. Natl. Acad. Sci. USA, 89:4210-4214, 1992.
Reiser, et al., "Murine B7 Antigen Provides an Efficient Costimulatory Signal for Activation of Murine T Lymphocytes via the T-Cell Receptor/CD3 Complex," Proc. Natl. Acad. Sci. USA, 89:271-275,1992.
Richards et al, "Phase IB Evaluation of OKT3," 82nd Annual Meeting of the American Association for Cancer Research, Houston, Texas, USA, May 15-18, 1991.
Robbins and Bergdoll, "Production of rabbit antisera to the *Staphylococcal* enterotoxins," Immunology, 78(5):4028, abstract No. 35589, 1984.
Roitt et al, Immunology, p. 9.9, Gower Medical Publishing, London, England, van den Berghe, ed., 1989.
Routledge et aI., "A humanized monovalent CD3 antibody which can activate homologous complement," C105 European Journal of Immunology, 21: 2717-2725 (1991).
Rudd et al., "Molecular Interactions, T-Cell Subsets and a Role of the CD4/CD8:p56$^{lck}$ Complex in Human T-Cell Activation," Immunological Reviews, 111:225-266,1989.
Rudd, "CD4, CD8 and the TCR-CD3 Complex: a Novel Class of Protein-Tyrosine Kinase Receptor," Immunology Today, 11(11):400-406,1990.
Schiff et al., "Lymphocyte killing of macrophages induced by OKT3 monoclonal antibody," FASEB, 70th Annual Meeting, St. Louis, Missouri, Apr. 13-18, 1986, p. 1100, No. 5499.
Schwartz, R.H., "A Cell Culture Model for T Lymphocyte Clonal Anergy," Science, 248:1349-1356,1990.
Schwartz, RH., et al., "T-Cell Clonal Anergy," Cold Spring Harbo Symposia on Quantitative Biology, LIV:605-610,1989.
Seed, B. and Aruffo, A., "Molecular cloning of the CD2 antigen, the T-cell erythrocyte receptor, by a rapid immunoselection procedure," Proc. Natl. Acad. Sci. USA, 84:3365-3369,1987.
Seed, Brian, "An LFA-3 cDNA encodes a phospholipid-linked membrane protein homologous to its receptor CD2," Nature, 329:840-842, 1987.
Sehon, "Carl Prausnitz Memorial Lecture, Suppression of Antibody Responses by Chemically Modified Antigens," Int. Arch. Allergy Appl. Immunol., 94:11-20, 1991.
Shahinian, A., et al., "Differential T Cell Costimulatory Requirements in CD28-Deficient Mice," Med. and Clin. Microbiol., 83(10):AB-590, abstract No. 98234, 1987.

Shinagawa et al., "Purification of *Staphylococcal* Toxic Shock Syndrome Toxin-1 (Enterotoxin F) and Preparation of Anti-Toxic Shock Syndrome Toxin-1 Serum," J. Fac. Agriciwate Univ., 18(1):47-58,1987.
Smith et al., "Inhibition of T Cell Activation by a Monoclonal Antibody Reactive Against the a3 Domain of Human MHC Class I Molecules," The Journal of Immunology, 1054-1067, Jul. 1994.
Smith et al., "T cell activation by anti•T3 antibodies: comparison of IgG1 and IgG2b switch variants and direct evidence for accessory function of macrophage Fc receptors," European Journal of Immunology, 16: 478-486 (1986).
Spits et al., "Characteristics of a Monoclonal Antibody (WT•31) That Recognizes a Common Epitope on the Human T Cell Receptor for Antigen," The Journal of Immunology, 135(3): 1922-1928 (1985).
Tan et al., "Influence of the hinge region on complement activation, C1q binding, and segmental flexibility in chimeric human immunoglobulins," Proc. Nat!. Acad. Sci, USA, 87:162-166 (1990).
Tao et al.,"Structural Features of Human Immunoglobulin G that Determine Isotype-specific Differences in Complement Activation," J Exp, Med, 178: 661-667 (1993).
Tao et al., "The Differential Ability of Human IgG1 and IgG4 to Activate Complement Is Determined by the COOH terminal Sequence of the CH2 Domain," J Exp, Med., 173: 1025-1028 (1991).
Thistlethwaite, Jr. et al., "OKT3 Treatment of Steroid-Resistant Renal Allograft Rejection," Transplantation, 43(2):176-184,1987.
Urba et al., "Anti-CD3 monoclonal antibody treatment of patients with CD3-negative tumors," Canc. Res., 52:2394-2401, May 1, 1992.
Utset Tammy et al., "Modified anti-CD3 therapy in psoriatic arthritis: a phase 1/11 clinical trial," The Journal of Rheumatology, 2002, vol. 29(9), pp. 1907-1913.
von Herrath et al., "Non mitogenic CD3 antibody reverses virallY induced (rat insulin promoter-lymphocyte choriomeningitis virus) autoimmune diabetes without impeding viral clearance," J. Immunol., 2002, vol. 168(2), pp. 933-941.
Waid et al., "Treatment of Acute Cellular Rejection with T1OB9.1A-31 or OKT3 in Renal Allograft Recipients," Transplantation, 53(1):80-86,1992.
Wedrychowski et al., "Immune Enhancers Composed of Polyvalent Binding Sites of Anti-CD3 Antibodies," Bio/Technology, 11:486-489,1993.
White et al., "The Vβ-Specific Superantigen *Staphylococcal* Enterotoxin B: Stimulation of Mature T Cells and Clonal Deletion in Neonatal Mice," Cell, 56:27-35, 1989.
Weiss, "Structure and Function of the T Cell Antigen Receptor," J Clin. Invest., 86: 1015-1022 (1990).
Woodle et al, "Humanized OKT3 Antibodies: Successful Transfer of Immune Modulating Properties and Idiotype Expression," The Journal of Immunology,148:2756-2763, May 1992.
Woodle et al., "T-Cell Activation and Lymphokine Production Induced by Antihuman CD3 Monoclonal Antibodies," Transplantation Proceedings, 23(1): 81-82 (1991).
Woodle et al,"OKT3 F(AB')2 Fragments—Retention of the Immunosuppressive Properties of Whole Antibody with Marked Reduction in T Cell Activation and Lymphokine Release," Transplantation, 52(2): 354-360 (1991).
Wu, Y., et al., "A Major Costimulatory Molecule on Antigen-Presenting Cells, CTLA4 Ligand A, is Distinct From B7," J. Exp. Med., 178:1789-1793, 1993.
Xu D et aI., "In vitro characterization of five humanized OKT3 effector function variant antibodies," Cellular Immunology, 2000, vol. 200(1), pp. 16-26.
Xu et al., "Construction of a mouse-human chimeric light chain from murine monoclonal antibodies 33.28 against colorectal carcinoma-associated antigens," abstract No. 2109, FASEB 75th Annual Meeting, Atlanta, GA, Apr. 21-25, 1991.
Zivin, R.A., A talk presented by Linda Jolliffe, sponsored by Journal of Human Anflbod'les and Hybridomas, abstract for Second International Conference on Human Antibodies and Hybridomas, Mar. 24-26, 1992, Cambridge, England.
Zivin, R.A., "Functional Analysis of Humanized OKT3 and OKT4A," Second Annual IBC International Conference on Antibody Engineering, Dec. 16-18, 1991, San Diego, CA.

(56) References Cited

OTHER PUBLICATIONS

Hale et al., "Phase I Study of an Engineered Aglycosylated Humanized CD3 Antibody in Renal Transplant Rejection" Transplantation, 68(11): 1632-1637, 1999.
PCT Search Report dated Aug. 8, 2008 in corresponding PCT/US2007/071275.
Achenbach et al., "Modulating the Autoimmune Response in Type 1 Diabetes," The Review of Diabetic Studies, 1(3), pp. 137-140, 2004.
Bresson et al., "Limitations in Immunotherapy with CD3 Antibodies: Comment on the Article by Drs. Chatenoud and Bach," The Review of Diabetic Studies, 2(4), pp. 187-189, 2005.
Bresson et al., "Immunotherapy After Recent-Onset Type 1 Diabetes: Combinatorial Treatment for Achieving Long-Term Remission in Humans?," The Review of Diabetic Studies, 1(3), pp. 108-112, 2004.
Chatenoud et al., "Questioning Four Preconceived Ideas on Immunotherapy of Clinical Type 1 Diabetes: Lessons from Recent CD3 Antibody Trials," The Review of Diabetic Studies, 2(3), pp. 116-120, 2005.
Belmar et al., "Efficacy of an Anti-Mouse CD3 FC Modified Antibody on Experimental Autoimmune Encephalomyelitis (EAE)," Clinical Immunology, vol. 119, p. S106, Jan. 1, 2006.
Supplementary European Search Report for European Application No. EP 07812153 dated May 19, 2010.
"MacroGenics and Lilly Announce Pivotal Clinical Trial of Teplizumab Did Not Meet Primary Efficacy Endpoint," Eli Lilly and Company Press Release Archives, Oct. 2010.
Shao et al., "Expression of Chimeric Anti-CD3 IgG Antibody in Mammalian Cells and Analysis of its Biological Activity," Sheng Wu Gong Cheng Xue Bao, 19(5), pp. 527-531, Sep. 2003, Abstract only.
Search Report and Written Opinion from corresponding Singapore Patent Application No. 201005116-7 issued on Feb. 15, 2011.
Beltzer et al., "Yeast LEU4 Encodes Mitochondrial and Nonmitochondrial Forms of α-Isopropylmalate Synthase," Journal of Biological Chemistry, 1998, 26:3(1), pp. 368-374.
Diabetes Mellitus (DM), Merck Manuals, pp. 2-21, Feb. 16, 2011.
Herold, K.C., et al., "Treatment with hOKT311 (Ala-Ala) improves Insulin Responses and Reduces Insulin Requirements in PTS With New Onset Type 1 Diabetes (T1DM)," $64^{th}$ Annual Meetings of the American Diabetes Association, vol. 53, No. 2, p. A63, Jun. 2004.
Lernmark et al., "Immunomodulation with Human Recombinant Autoantigens," Trends immunol., 26(11), pp. 608-612, Sep. 2005.
Leslie, R.D.G., et al., "Clinical Review: Type 1 Diabetes and Latent Autoimmune Diabetes in Adults: One End of the Rainbow," J. Clin. Endocrinol. Metab., Feb. 2006, vol. 91, pp. 1654-1659.
Renders et al, "Engineered CD3 Antibodies for Immunosuppression," Clin. Exp. Immunol., 133, pp. 307-309, 2003.
Rudikoff et al., "Single Amino Acid Substitution Altering Antigen-Binding Specificity," Proc. Natl. Acad. Sci., 79, pp. 1979-1983, Mar. 1982.
Wells, "GSK and Tolerx's Type I Diabetes Drug Otelixitumab has failed to Meet its Primary Endpoint in a Late-Stage Trial," InPharm, retrieved from http://www.inpharm.com/news/150858/gsk-tolerx-otelixizumab-phase-iii-failure, Mar. 14, 2011.
FDA's Oncology Tools: Dose Calculator retrieved from FDA website Dec. 2, 2009.
Naik, et al., 2009, Latent Autoimmune Diabetes in Adults, *J. Clin. Endocrinol. Metab.* 94(12): 4635-4644.
Norman et al., "Phase I Trial of HuM291, A Humanized Anti-CD3 Antibody, in Patients Receiving Renal Allograft from Living Donors," Transplantation, vol. 70, No. 12, pp. 1707-1712, Dec. 27, 2000.
Palmer et al., 2005, Is Latent Autoimmune Diabetes in Adults Distinct From Type 1 Diabetes or Just Type 1 Diabetes at an Older Age? *Diabetes,* 54(Supplement 2): S62-S67.
Stenstrom et al., "Latent Autoimmune Diabetes in Adults: Definition, Prevalence, β-Cell Function, and Treatment," Diabetes, 54(2), pp. S68-S72, 2005.
Woodle et al., "Phase I Trial of a Humanized, Fc Receptor Nonbinding OKT3 Antibody, huOKT3$\gamma_1$ (Ala-Ala) in the Treatment of Acute Renal Allograft Rejection," Transplantation, vol. 68, No. 5, pp. 608-616, Sep. 15, 1999.

* cited by examiner

```
              1         10        20        30        40        50        60
Okt3v1        QIVLTQSPAIMSASPGEKVTMTCSASS-SVSYMNWYQQKSGTSPKRWIYDTSKLASGVPA
REI           DIQMTQSPSSLSASVGDRVTITCQASQDIKYLNWYQQTPGKAPKLLIYEASNLQAGVPS
gLA           .........................SAS-SVS.M.........................DT.K.AS...
gLC           .........................SAS-SVS.M...................RW..DT.K.AS...

70        80        90       100   108
Okt3v1        HFRGSGSGTSYSLTISGMEAEDAATYYCQQWSSNPFTFGSGTKLEINR    (SEQ ID NO:1)
REI           RFSGSGSGTDYTFTISSLQPEDIATYYCQQYQSLPYTFGQGTKLQITR    (SEQ ID NO:2)
gLA           ..........................WS.N.F................   (SEQ ID NO:3)
gLC           ..........................WS.N.F................   (SEQ ID NO:4)
```

FIG. 1A

```
         1           10         20         30         40         50      a  60
Okt3vh   QVQLQQSGAELARPGASVKMSCKASGYTFTRYTMHWVKQRPGQGLEWIGYINPSRGYTNYN
KOL      QVQLVESGGGVVQPGRSLRLSCSSSGFIFSSYAMYWVRQAPGKGLEWVALIWDDGSDQHYA
gH       . . . . . . . . . . . . . . . . . . . . . . . . YI.IR.I.H . . . . . . . . . Y.NPSRGYTN.N
gHA      . . . . . Q . . . . . . . . . . . . . . . . KA.YI.IR.I.H . . . . . . . . IGY.NPSRGYTN.N
gHG      . . . . . Q . . . . . . . . . . . . . . . . KA.YI.IR.I.H . . . . . . . . IGY.NPSRGYTN.N 70          80  abc                     90         100abcdefghi        110
Okt3vh   QKFKDKAILTTDKSSSTAYMQLSSLTSEDSAVYYCARYYDDHYCL- - - - - - DYWGQGTTLTVSS      (SEQ ID NO:5)
KOL      DSVKGRFTISRDNSKNTLFLQMDSLRPEDTGVYFCARDGGHGFCSSASCFGPDYWGQGTPVTVSS    (SEQ ID NO:6)
gH       QKF.D . . . . . . . . . . . . . . . . . . . . . . . . . . . . . . . . . . . . . YDDHY.L - - - - - - - - - - . . . . . . . . . . . .   (SEQ ID NO:7)
gHA      QK..D . . . . I.K.S.A . . . . . . . . . . . A..Y . . . . . . YDDHY.L - - - - - - - - - - . . . . . . . . . . . .   (SEQ ID NO:8)
gHG      QK..D . . . . . . . . . . . . . . . . . . . A . . . . . . . . . . . . . . . . YDDHY.L - - - - - - - - - - . . . . . . . . . . . .   (SEQ ID NO:9)
```

FIG. 1B

Nucleotide Sequence of OKT3γ1 Light Chain
```
ATGGGATGGAGCTGTATCATCCTCTTCTTGGTAGCAACAGCTACAGGTGTCCACTCCGACATCCA
GATGACCCAGTCTCCTTCTTCTCTGTCTGCTTCTGTCGGAGACAGAGTCACAATCACATGTTCTG
CTTCTAGCTCTGTCTCTTACATGAACTGGTACCAGCAGACACCTGGAAAGGCTCCTAAGCGGTG
GATCTACGACACATCTAAGCTCGCTTCTGGAGTCCCTTCTAGATTCTCTGGTTCTGGCTCTGGAA
CAGACTACACATTCACAATCTCTTCTCCAACCTGAGGACATCGCTACATACTACTGCCAACAG
TGGTCTAGCAATCCTTTCACATTCGGACAGGGAACAAAGCTGCAGATCACAAGAACTGTGGCGG
CGCCGTCTGTCTTCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGGATAACGCCCTCC
AATCGGGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGTGTTAG
```

FIG. 2A

Amino-Acid Sequence of OKT3γ1 Light Chain
```
MGWSCIILFLVATATGVHSDIQMTQSPSSLSASVGDRVTITCSASSSVSYMNWYQQTP
GKAPKRWIYDTSKLASGVPSRFSGSGSGTDYTFTISSLQPEDIATYYCQQWSSNPFTF
GQGTKLQITRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRG
EC
```

FIG. 2B

Nucleotide Sequence of OKT3γ1 (ala-ala) Heavy Chain

```
ATGGGATGGAGCTGTATCATCCTCTTCTTGGTAGCAACAGCTACAGGTGTCCACTCCCAGGTTCA
GCTGGTGCAGTCTGGAGGAGGAGTCGTCCAGCCTGGAAGGTCCCTGAGACTGTCTTGTAAGGC
TTCTGGATACACCTTCACTAGATACACAATGCACTGGGTCAGACAGGCTCCTGGAAAGGGACTC
GAGTGGATTGGATACATTAATCCTAGCAGAGGTTATACTAACTACAATCAGAAGGTGAAGGACAG
ATTCACAATTTCTAGAGACAATTCTAAGAATACAGCCTTCCTGCAGATGGACTCACTCAGACCTGA
GGATACCGGAGTCTATTTTTGTGCTAGATATTACGATGACCACTACTGTCTGGACTACTGGGGCC
AAGGTACCCCGGTCACCGTGAGCTCAGCTTCCACCAAGGGCCCATCGGTCTTCCCCCTGGCAC
CCTCCTCCAAGAGCACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGTGCACACCTTCCCGG
CTGTCCTACAGTCCTCAGGACTCTACTCCCTCAGCAGCGTGGTGACCGTGCCCTCCAGCAGCTT
GGGCACCCAGACCTACATCTGCAACGTGAATCACAAGCCCAGCAACACCAAGGTGGACAAGAAA
GTTGAGCCCAAATCTTGTGACAAAACTCACACATGCCCACCGTGCCCAGCACCTGAGGCCGCGG
GAGGACCATCAGTCTTCCTCTTCCCCCCAAAACCCAAGGACACCCTCATGATCTCCCGGACCCC
TGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTGGGAGAGC
AATGGGCAGCCGGAGAACAACTACAAGACCACGCCTCCCGTGCTGGACTCCGACGGCTCCTTC
TTCCTCTACAGCAAGCTCACCGTGGACAAGAGCAGGTGGCAGCAGGGGAACGTCTTCTCATGCT
CCGTGATGCATGAGGCTCTGCACAACCACTACACGCAGAAGAGCCTCTCCCTGTCTCCGGGTAA
ATGA
```

FIG. 2C

Amino-Acid Sequence of OKT3γ1 (ala-ala) Heavy Chain

```
MGWSCIILFLVATATGVHSQVQLVQSGGGVVQPGRSLRLSCKASGYTFTRYTMHWV
RQAPGKGLEWIGYINPSRGYTNYNQKVKDRFTISRDNSKNTAFLQMDSLRPEDTGVY
FCARYYDDHYCLDYWGQGTPVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKP
SNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEAL
HNHYTQKSLSLSPGK
```

FIG. 2D

METHODS FOR THE TREATMENT OF AUTOIMMUNE DISORDERS USING IMMUNOSUPPRESSIVE MONOCLONAL ANTIBODIES WITH REDUCED TOXICITY

CROSS REFERENCE TO RELATED APPLICATIONS

This application claims benefit of U.S. Provisional Application Ser. No. 60/813,903, filed Jun. 14, 2006 and U.S. Provisional Application Ser. No. 60/871,361, filed Dec. 21, 2006, the contents of each of which are incorporated herein by reference for all purposes.

1. INTRODUCTION

The present invention provides methods of treating, preventing, slowing the progression of, or ameliorating the symptoms of T cell mediated immunological diseases, particularly autoimmune diseases (e.g., autoimmune diabetes (i.e. type 1 diabetes or insulin-dependent diabetes mellitus (IDDM)) and multiple sclerosis) through the use of anti-human CD3 antibodies. The antibodies of the invention of the invention are preferably used in low dose dosing regimens, chronic dosing regimens or regimens that involve redosing after a certain period of time. The methods of the invention provide for administration of antibodies that specifically bind the epsilon subunit within the human CD3 complex. Such antibodies modulate the T cell receptor/alloantigen interaction and, thus, regulate the T cell mediated cytotoxicity associated with autoimmune disorders. Additionally, the methods of the invention provide for use of anti-human CD3 antibodies modified such that they exhibit reduced or eliminated effector function and T cell activation as compared to non-modified anti-human CD3 antibodies.

2. BACKGROUND OF THE INVENTION

2.1 Autoimmune Diseases

Autoimmune diseases are caused when the body's immune system, which normally defends the body against bacteria, viruses and other infective agents, attacks "self" tissue, cells and organs. The mobilization of the immune system against such self targets is termed autoimmunity. Although some autoimmunity is present in every individual, rigid control systems suppress the self-recognizing cells of the immune system to an extent that the autoimmunity is normally asymptomatic. Disease states arise when there is some interruption in the control system, allowing the autoimmune cells to escape suppression, or when there is some change in a target tissue such that it is no longer recognized as self. The mechanisms underlying these changes are not well understood, but have been theorized to be the result of aberrant immune stimulation in genetically predisposed individuals.

Autoimmune diseases can be organ specific or systemic and are provoked by differing pathogenic mechanisms. Organ specific autoimmunization is characterized by tolerance and suppression within the T cell compartment, aberrant expression of major-histocompatibility complex (MHC) antigens, antigenic mimicry and allelic variations in MHC genes. Systemic autoimmune diseases usually involve polyclonal B cell activation and abnormalities of immunoregulatory T cells, T cell receptors and MHC genes. Examples of organ specific autoimmune diseases are diabetes, cutaneous psoriasis, ulcerative colitis, hyperthyroidism, autoimmune adrenal insufficiency, hemolytic anemia, multiple sclerosis and rheumatic carditis. Representative systemic autoimmune diseases include systemic lupus, erythematosus, rheumatoid arthritis, psoriatic arthritis, Sjogren's syndrome polymyositis, dermatomyositis and scleroderma.

Also, while not having an autoimmune disorder, organ transplant recipients often experience similar symptoms and require similar therapies to autoimmune patients. Immune system attacks on the transplanted organ(s) can lead to organ failure or more serious systemic complications, e.g., graft-vs.-host disease (GVHD) in bone-marrow transplant recipients.

There is a clear need for improved strategies to treat autoimmune disorders and/or to modulate immune response. Currently, immune system disorders are treated with immunosuppressive agents such as cortisone, aspirin derivatives, hydroxychloroquine, methotrexate, azathioprine, cyclophsophamide and various biologics such as anti TNF antibodies, and/or combinations of the foregoing. The treatments are varyingly successful, dependent on the individual patient and disorder. However, a dilemma in the use of such general immunosuppressive therapies arises in that the greater the immune-suppression, and thus the increased potential for successful treatment of the autoimmune disorder, the more at-risk the patient becomes for developing opportunistic infections. Further, due to the compromised nature of the patient's immune system, even a minor infection can rapidly become of serious concern.

2.1.1 Diabetes

Diabetes is typically classified as one of two types: type 1 or type 2 diabetes. Type 2 diabetes is a non-autoimmune disease that is typically diagnosed in adults. It is a progressive disease that develops when the body does not produce sufficient insulin or fails to efficiently use the insulin it produces (a phenomenon known as insulin resistance). Patients diagnosed with type 2 diabetes are typically over age 45, overweight (BMI of 25 or higher) or obese (BMI of 30 or higher), physically inactive, have hypertension (blood pressure of 140/90 mm Hg or higher in adults), and have HDL cholesterol of 35 mg/dL or lower and/or triglyceride level of 250 mg/dL.

Type 1 diabetes, also known as juvenile diabetes or insulin-dependent diabetes mellitus, is an autoimmune disease that is typically diagnosed in children (although Adult-Onset type 1 diabetes may be present in adults). Insulin-dependent diabetes mellitus (IDDM) affects 15 million people in the United States with an estimated additional 12 million people who are currently asymptomatic, and, thus, unaware that they have this disease. Risk factors for developing type 1 diabetes include presumptive genetic factors, exposure to childhood viruses or other environmental factors, and/or the presence of other autoimmune disorders. Although the genetic factors associated with type 1 diabetes are not fully understood, risks for the development of the disease have been linked to both family history and ethnicity. For example, a child that has a parent or sibling with type 1 diabetes has a higher risk of developing type 1 diabetes than a child of non-diabetic parents or with non-diabetic siblings. Further, the genetic factors associated with the risk for developing type 1 diabetes appear to be linked to a particular HLA type: HLA-DR3 and DR4 are associated with a higher risk in Caucasians; HLA-DR7 is associated with a higher risk in people of African decent; and HLA-DR9 is associated with a higher risk in people of Japanese descent.

Unknown factors, including childhood viruses or exposure to some other environmental factor (e.g., exposure to certain foods or chemicals), are also theorized to potentiate or activate an inherited genetic factor and cause the onset of type 1 diabetes. Viruses that have been associated with type 1 diabetes include coxsackie B virus, enteroviruses, adenoviruses, rubella, cytomegalovirus, and Epstein-Barr virus. Last, the presence of other autoimmune disorders, such as thyroid disease and celiac disease, raises the risk of developing type 1 diabetes.

Type 1 Diabetes is caused by an autoimmune response in which the insulin producing β-cells of the pancreas (also known as islet cells) are gradually destroyed. The early stage of the disease, termed insulitis, is characterized by infiltration of leukocytes into the pancreas and is associated with both pancreatic inflammation and the release of anti-β-cell cytotoxic antibodies. As the disease progresses, the injured tissue may also attract lymphocytes, causing yet further damage to the β-cells. Also, subsequent general activation of lymphocytes, for example in response to a viral infection, food allergy, chemical, or stress, may result in yet more islet cells being destroyed. Early stages of the disease are often overlooked or misdiagnosed as clinical symptoms of diabetes typically manifest only after about 80% of the β-cells have been destroyed. Once symptoms occur, the type-1 diabetic is normally insulin dependent for life. The dysregulation of blood-glucose levels associated with diabetes can lead to blindness, kidney failure, nerve damage and is a major contributing factor in the etiology of stroke, coronary heart disease and other blood vessel disorders.

2.1.2 Multiple Sclerosis

Multiple sclerosis (MS) is a chronic, often disabling inflammatory disease of the central nervous system (CNS). MS is typified pathologically by multiple inflammatory foci, plaques of demyelination, gliosis, and axonal pathology within the brain and spinal cord. Although the causal events that precipitate the disease are unknown, converging lines of evidence suggest that the disease is caused by a disturbance in immune function. This disturbance permits cells of the immune system to attack myelin, the insulating sheath that surrounds the axons located in the CNS (i.e., the brain and spinal cord). When observed microscopically, plaques consist of inflammatory cells, astroglial cells, edema, and destroyed myelin fragments. When myelin is damaged, electrical impulses cannot travel quickly along nerve fiber pathways in the brain and spinal cord. Disruption of electrical conductivity results in fatigue and disturbances of vision, strength, coordination, balance, sensations, and bladder and bowel function. Thus, typical symptoms include one or more of weakness or paralysis in one or more extremities, tremor in one or more extremities, muscle spasticity, muscle atrophy, dysfunctional movement, numbness or abnormal sensation in any area, tingling, facial pain, extremity pain, loss of vision in one or both eyes, double vision, eye discomfort, uncontrollable rapid eye movements, decreased coordination, loss of balance, decreased ability to control small or intricate movements, walking or gait abnormalities, muscle spasms, dizziness, vertigo, urinary hesitancy, urinary urgency, increased urinary frequency, incontinence, decreased memory, decreased spontaneity, decreased judgment, loss of ability to think abstractly, loss of ability to generalize, depression, decreased attention span, slurred speech, difficulty speaking or understanding speech, fatigue, constipation, hearing loss, and/or positive Babinski's reflex. The symptoms recur periodically, last days to months, then reduce or disappear. With each recurrence, the symptoms may vary or be completely different as new areas are affected.

Studies of the natural history of MS suggest that there are different patterns of disease activity. Some patients have rare attacks, some have frequent attacks, and others gradually but steadily worsen without experiencing attacks. Patients who have rare attacks and are minimally disabled ten years after being diagnosed with MS are said to have benign MS. This group constitutes only about 10-15% of the total MS patient population, although there is some evidence suggesting that this course may be more common than is currently appreciated. Patients who have attacks with full or partial recovery and are otherwise stable between attacks are defined as having relapsing-remitting MS. Approximately 80-90% of patients with MS initially experience a relapsing-remitting course. Of these, approximately 50% will have difficulty walking 15 years after onset and 80% will ultimately (after about 25 years) experience gradual progression of disability with or without attacks. Patients who first experience exacerbations and later experience gradual progression of disability have secondary progressive MS. Approximately 10-15% of MS patients do not experience an initial attack. Those patients who gradually worsen after the appearance of the first symptom have primary progressive MS. A few patients with primary progressive MS will later experience an exacerbation. These patients have progressive-relapsing MS.

There is as yet no cure for MS. Many patients do well with no therapy at all, especially since many medications have serious side effects and some carry significant risks. However, three forms of beta interferon (AVONEX® (interferon beta-1a), BETASERON® (interferon beta-1b), and REBIF® (interferon beta-1a)) have now been approved by the Food and Drug Administration for treatment of relapsing-remitting MS. Beta interferon has been shown to reduce the number of exacerbations and may slow the progression of physical disability. When attacks do occur, they tend to be shorter and less severe. The FDA also has approved a synthetic form of myelin basic protein copolymer I, COPAXONE® (glatiramer acetate), for the treatment of relapsing-remitting MS. Copolymer I has few side effects, and studies indicate that the agent can reduce the relapse rate by almost one third. An immunosuppressant treatment, NOVATRONE® (mitoxantrone), is also approved by the FDA for the treatment of advanced or chronic MS.

2.2 T Cell Functionality in Diabetes and Other Autoimmune Disorders

Destruction of β-cells in diabetes, of myelin in multiple sclerosis, or of the target cells of other autoimmune disorders is believed largely mediated by cytotoxic T-lymphocytes (CTLs—also known as CD8+ T cells) that specifically recognize antigenic, target cell derived peptides. CTLs, as well as other types of T cells, recognize these antigenic peptides through their specific T cell receptor (TcR). Unlike antibodies which recognize soluble whole foreign proteins as antigen, the TcR instead interacts with small peptidic antigens presented only in complex with major histocompatibility complex (MHC) proteins.

Most cells of the body express MHC molecules of various classes on their surface and, depending on the class of MHC expressed, will present either soluble antigens, those dispersed within the lymph and/or circulatory systems, or fragments of their cytoplasmic proteins. MHC molecules (called human leukocyte antigens or HLA in humans) and TcRs are extremely polymorphic, each clonal variation recognizing and binding to a single peptidic sequence, or set of similar peptidic analogs. Apart from cells specific to the immune system, i.e. B cells and T cells, cells of the body express multiple variants of the MHC molecule, each variant binding to a different peptide sequence. In contrast, during maturation, B and T cells lose the ability to express multiple variants of MHC and TcR, respectively. Mature T cells, therefore, will express only one of the possible variants of the TcR and will thus recognize/bind a single MHC/antigen complex.

Binding of a TcR to a MHC/antigen complex elicits an intracellular signal cascade within the T cell, termed activation, which results in clonal proliferation of the T cell and class-specific T cell responses. For example, in CTLs the response to activation also includes the release of cytotoxic enzymes that result in apoptosis/destruction of the target cell.

2.3 Modulation of T Cell Activation by Monoclonal Antibodies

The finding that autoimmune diseases are at least partially caused by aberrant T cell action has lead to the investigation of therapies that either eliminate problematic T cell clones (those expressing TcRs against self antigens) or selectively reduce undesired T cell activity/activation. T cell activation due to TcR binding is, however, an unexpectedly complex phenomenon due to the participation of a variety of cell surface molecules expressed on the responding T cell population (Billadeau et al., 2002, J. Clin. Invest. 109:161-168; Weiss, 1990, J. Clin. Invest. 86:1015-1022; Leo et al., 1987, PNAS 84:1374-1378; Weiss et al., 1984, PNAS 81:4169-4173; Hoffman et al., 1985, J. Immunol. 135:5-8).

Targeted therapies directed against general T cell activation were problematic in that the TcR is composed of a disulfide-linked heterodimer, containing two clonally distributed, integral membrane glycoprotein chains, $\alpha$ and $\beta$, or $\gamma$ and $\delta$. Most of the research in modulation of T cell activation was done in connection with improving immune suppression in organ transplant recipients. One of the first clinically successful methods of selectively reducing T cell activation was the use of monoclonal antibodies. U.S. Pat. No. 4,658,019, describes a novel hybridoma (designated OKT3, ATCC Accession No. CRL-8001) which produces a murine monoclonal antibody against an antigen found on essentially all normal human peripheral T cells. Binding of OKT3 to T cells in vivo produces pronounced, reversible immunosuppression. OKT3 was found to recognize an epitope on the 8-subunit within the human CD3 complex (Salmeron et al., 1991, J. Immunol. 147:3047-3052; Transy et al., 1989, Eur. J. Immunol. 19:947-950; see also, U.S. Pat. No. 4,658,019). The CD3 complex (also known as T3) is comprised of low molecular weight invariant proteins, which non-covalently associate with the TcR (Samelson et al., 1985, Cell 43:223-231). The CD3 structures are thought to represent accessory molecules that may be the transducing elements of activation signals initiated upon binding of the TcR $\alpha$-$\beta$ to its ligand.

OKT3 possesses potent T cell activating and suppressive properties (Van Seventer, 1987, J. Immunol. 139:2545-2550; Weiss, 1986, Ann. Rev. Immunol. 4:593-619). Fc receptor-mediated cross-linking of TcR-bound anti-CD3 mAb results in T cell activation marker expression, and proliferation (Weiss et al., 1986, Ann. Rev. Immunol. 4:593-619). Similarly, in vivo administration of OKT3 results in both T cell activation and suppression of immune responses (Ellenhorn et al., 1990, Transplantation 50:608-12; Chatenoud, 1990, Transplantation 49:697). Repeated daily administration of OKT3 results in profound immunosuppression, and provides effective treatment of rejection following renal transplantation (Thistlethwaite, 1984, Transplantation 38:695).

The use of therapeutic mAbs, including, for example, OKT3, is limited by problems of "first dose" side effects, ranging from mild flu-like symptoms to severe toxicity. The first dose side effects are believed to be caused by cytokine production stimulated by T cell activation. It has been shown that the activating properties of Anti CD3 monoclonal antibodies result from TcR cross-linking mediated by the antibodies bound to T cells (via its variable domain) and to Fc$\gamma$R-bearing cells via its Fc domain) (Palacios et al., 1985, Eur. J. Immunol. 15:645-651; Ceuppens et al., 1985, J. Immunol. 134:1498-1502; Kan et al., 1986, Cell Immunol. 98:181-185). For example, the use of OKT3 was found to trigger activation of mAb-bound T cells and Fc$\gamma$R-bearing cells prior to achieving immune suppression, resulting in a massive systemic release of cytokines (Abramowicz, 1989, Transplantation 47:P606; Chatenoud, 1989, N. Eng. J. Med. 25:1420-1421). Reported side effects of OKT3 therapy include flu-like symptoms, respiratory distress, neurological symptoms, and acute tubular necrosis that may follow the first and sometimes the second injection of the mAb (Abramowicz, 1989, Transplantation 47:P606; Chatenoud, 1989, N. Eng. J. Med. 25:1420-1421; Toussaint, 1989, Transplantation 48:524; Thistlethwaite, 1988, Am. J. Kid. Dis. 11:112; Goldman, 1990, Transplantation 50:148).

Data obtained using experimental models in chimpanzees and mice have suggested that preventing or neutralizing the cellular activation induced by anti-CD3 mAbs reduces the toxicity of these agents (Parleviet, 1990, Transplantation 50:889; Rao, 1991, Transplantation 52:691; Alegre, 1990, Eur. J. Immunol. 20:707; Alegre, 1990, Transplant Proc. 22:1920; Alegre, 1991, Transplantation. 52:674; Alegre, 1991, J. Immun. 146:1184-1191; Ferran, 1990, Transplantation 50:642). Previous results reported in mice using F(ab')$_2$ fragments of 145-2C11, a hamster anti-mouse CD3 that shares many properties with OKT3, have suggested that, in the absence of Fc$\gamma$R binding and cellular activation, anti-CD3 mAbs retain at least some immunosuppressive properties in vivo (Hirsch, 1991, Transplant Proc. 23:270; Hirsch, 1991, J. Immunol. 147:2088). In addition, administration of anti-CD3 antibodies with reduced binding to Fc$\gamma$R to human patients resulted in generally only mild side effects and not the severe first class effects associated with OKT3 administration (Herold et al., 2005, Diabetes 54:1763).

2.4 Immunosuppressive Monoclonal Antibodies Exhibiting Reduced T Cell Activation U.S. Pat. No. 6,491,916, U.S. Pat. Application Pub. No. 2005/0064514 and U.S. Pat. Application Pub. No. 2005/0037000 describe the modification of the Fc regions of immunoglobulins such that the variant molecules exhibit enhanced or reduced binding to various Fc receptors when compared to immunoglobulins with wild type Fc domains. In particular the patents/applications describe modifications to the Fe regions of IgG antibodies such that the affinity for the Fc$\gamma$R is selectively enhanced or reduced. By tailoring the affinity for activating or suppressive Fc receptors, the specific immune response elicited by the therapeutic mAb may be more selectively controlled. For example, mutations in the $CH_2$ portion of a humanized OKT3 IgG4 have been identified (P234A and L235A) that significantly reduced binding of the mAb to human and murine Fc$\gamma$RI and II and lead to a markedly reduced activating phenotype in vitro (Alegre et al., 1992, 8$^{th}$ International Congress of Immunology 23-28; Alegre et al., 1994, Transplantation 57: 1537-1543; Xu et al., 2000, Cell Immunol. 200:16-26). Importantly, this variant mAb retained the capacity to induce TcR modulation and immunosuppression (Xu et al., 2000, Cell Immunol. 200:16-26). Other modifications to the Fe domain of anti-CD3 antibodies, such as mutations to make the antibody aglycosylated or other mutations of the Fe domain residues, to reduce binding to Fc$\gamma$R have been found to reduce toxicity while maintaining immunosuppressive activity (see, e.g., U.S. Pat. No. 6,491,916; U.S. Pat. No. 5,834,597, Keymeulen et al., 2005, N. Eng. J. Med. 325:2598, all of which are incorporated by reference herein in their entireties).

3. SUMMARY OF THE INVENTION

The present invention provides methods of treating, preventing, slowing the progression of and ameliorating the symptoms of T cell mediated immunological diseases, particularly autoimmune diseases, in subjects diagnosed with such diseases (and/or in subjects predisposed to developing such diseases or disorders), by administering to a subject in need thereof a therapeutically or prophylactically effective amount of an anti-CD3 antibody. In particular, the methods of the invention provide for administration of antibodies that specifically bind the epsilon subunit within the human CD3 complex. For example, such antibodies may be or may be derived from (e.g., humanized or chimerized versions of) one of the antibodies Leu-4, 500A2, CLB-T3/3, M291, YTH 12.5 or BMA030, or compete with one of Leu-4, 500A2, CLB-T3/3, M291, YTH 12.5 or BMA030 for binding (e.g., in an ELISA or immunoprecipitation assay). In a preferred embodiment, the antibody has the binding specificity of the murine monoclonal antibody OKT3 (see, e.g., U.S. Pat. Nos. 4,658,019 and 6,113,901, which are incorporated by reference herein in their entireties), e.g., binds to the same epitope as OKT3 and/or competes for binding (i.e., in an ELISA or immunoprecipitation assay) with OKT3, such as a humanized version of the antibody OKT3, e.g., OKT3-7 (see the antibodies disclosed in U.S. Pat. No. 6,491,916, which is incorporated herein by reference in its entirety). In preferred embodiments, the anti-CD3 antibody of the invention has diminished (such as, but not limited to, less than 50%, less than 40%, less than 30%, less than 20%, less than 10%, less than 5% or less than 1% as compared to binding by an antibody having a wild-type, glycosylated Fc domain) or, more preferably, no detectable binding to one or more of any FcγR (e.g., FcγRI, FcγRII or FcγRIII) via its Fc domain as determined by assays routine in the art. In addition or alternatively, the anti-CD3 antibody of the invention has diminished (such as, but not limited to, less than 50%, less than 40%, less than 30%, less than 20%, less than 10%, less than 5% or less than 1% as compared to binding by an antibody having a wild-type, glycosylated Fc domain) or, more preferably, no detectable binding to any complement receptors, such as, C1q, as determined in routinely used assays. In particular embodiments, the antibody is aglycosylated. In other embodiments, the antibody lacks an Fc domain (e.g., is a Fab fragment, $F(ab')_2$ or single chain antibody). In other embodiments, the antibody has an Fc domain having one or more amino acid modifications that reduce or abolish binding of the Fc domain to one or more of an FcγR. In certain embodiments, the Fc domain has an amino acid modification (i.e., insertion, substitution, deletion) at one or more of the residues 234, 235, 236, or 237. In preferred embodiments, the Fc domain has an alanine at position 234 of the Fc region (CH2) and or an alanine at position 235 of the Fc region (CH2), in particular having alanine at 234 and 235, such as OKT3γ1 (ala-ala). In other embodiments, the Fc domain has a glutamate at position 235.

The invention particularly provides methods of treating, preventing, slowing the progression of and/or ameliorating the symptoms of autoimmune diseases such as Type I Diabetes, multiple sclerosis, psoriasis, rheumatoid arthritis, lupus (particularly, cutaneous), inflammatory bowel disease (IBD), Crohn's disease, ulcerative colitis, effects from organ transplantation, graft vs. host disease (GVHD), etc. Particularly, the methods of the invention are advantageous in subjects with early stage disease to slow or reduce the damage from the autoimmunity and maintain a high level of function and/or reduce the need for other therapy; for example, in the treatment or prophylaxis of Type I diabetes, the methods of the invention may reduce the need for exogenous insulin administration is the subject. In addition, the methods of the invention advantageously reduce the incidence of or result in no incidence of cytokine release syndrome previously associated with administration of therapeutic antibodies, and, in particular, anti-CD3 antibodies. Cytokine release syndrome is manifested by, for example, headache, nausea, vomiting, fever, myalgias, arthralgias and shaking and may be caused by increased serum levels of, for example, IL-2, IL-6, IL-10, TNFα, and IFNγ. The methods also reduce the incidence and severity of other adverse effects, such as, but not limited to, EBV activation, immunogenicity (production of anti-idiotype antibodies, particularly IgE anti-idiotype antibodies), lymphopenia, thrombocytopenia or neutropenia.

In preferred embodiments, the anti-human CD3 antibodies are administered are administered at lower dosages or over shorter periods of time than prior dosing regimens. In particular, the invention contemplates dosing regimens in which less than 9,000 µg/m$^2$, and preferably, less than 8,000 µg/m$^2$, less than 7,500 µg/m$^2$, less than 7,000 µg/m$^2$, or less than 6,000 µg/m$^2$ total anti-human CD3 antibody is administered over the duration of the dosing, particularly of OKT3γ1 (ala-ala), or of another anti-human CD3 antibody, such as ChAglyCD3 (TRX4™) or HUM291 (visilizumab; NUVION™). In certain embodiments, the antibodies of the invention are administered to the subject in need thereof using a mode other than intravenous administration that provides the pharmacological equivalent to the foregoing amounts of OKT3γ1 (ala-ala) as administered intravenously. The invention further contemplates methods in which the patient is chronically administered low doses of the anti-human CD3 antibody and methods in which the patient is administered one or more additional rounds of the anti-human CD3 antibody treatment regimen approximately 6 months, 9 months, 12 months, 18 months, 2 years, 3 years or 5 years after the initial treatment, optionally depending on clinical parameters, or is administered another round of treatment with anti-human CD3 antibody every approximately 6 months, 9 months, 12 months, 18 months, 2 years, 3 years or 5 years, optionally depending on clinical parameters.

The invention particularly provides methods of treating, preventing, slowing the progression of or ameliorating the symptoms of autoimmune diseases and disorders, e.g., type 1 diabetes, by administration of anti-human CD3 antibodies having reduced toxicity; e.g. having reduced binding to FcγRs. Particularly, the methods of the invention are advantageous in subjects with early stage disease in order to slow or reduce the damage from the autoimmunity and maintain a high level of function. In certain embodiments, the methods of the invention may also reduce the need for additional therapy for the autoimmune disease or disorder; for example, in the treatment or management of Type I diabetes, the methods of the invention may reduce or eliminate the need for administration of exogenous insulin in the subject. In addition, the methods of the invention advantageously reduce the incidence of or result in no incidence of cytokine release syndrome previously associated with administration of anti-human CD3 antibodies such as OKT3. Cytokine release syndrome is manifested by, for example, headache, nausea, vomiting, fever, myalgias, arthralgias and shaking and may be caused by increased serum levels of, for example, IL-2, IL-6, IL-10, TNFα, and IFNγ. The methods also reduce the incidence and severity of other adverse effects, such as, but not limited to, EBV activation, immunogenicity (production of anti-idiotype antibodies, particularly IgE anti-idiotype antibodies), lymphopenia, thrombocytopenia or neutropenia.

In other embodiments, the invention provides methods of preventing or delaying the onset of an autoimmune disease or disorder in a subject predisposed to developing said disease or disorder, but which subject has yet to experience symptoms of or be diagnosed with said disease or disorder according to criteria accepted in the art (e.g., in Type I diabetes, a diagnosis according to criteria established by the American Diabetes Association: see, e.g., Mayfield et al., et al., 2006, Am. Fam. Physician 58:1355-1362, hereby incorporated by reference herein in its entirety). In other embodiments, administration of an antibody of the invention prevents onset and/or development of the disorder, prevents onset of symptoms of the disorder, and/or delays the positive diagnosis of said disorder by 2 months, 4 months, 6 months, 8, months, 10 months, 12 months, 15 months, 18 months, 21 months, or 24 months relative to a subject with similar clinical parameters who did not receive treatment.

According to the invention, the anti-human CD3 antibody is administered so as to reduce adverse effects, such as the cytokine release associated with antibody administration, EBV activation (as evidenced by EBV-induced lymphoproliferative diseases, e.g., mononucleosis) or lymphopenia (defined as <1000 lymphocytes/µL serum), associated with administration of anti-human CD3 antibodies, and also reduce the number of doses and duration of the administration. As used herein, "course of treatment" or "round of treatment" means administration of anti-human CD3 antibodies every day, every other day or every 3 or 4 days for a period of time, e.g. 1 to 30 days. In particular embodiments, the invention provides a treatment regimen of administration of a dose of the anti-human CD3 antibody for 2 days, 3 days, 4 days, 5 days, 6 days, 7 days, 8 days, 9 days, 10 days, 11 days, 12 days, 13 days or 14 days. In preferred embodiments, the administration is carried out on consecutive days but may be carried out on alternate days or on a schedule that alternates a number of consecutive days in which the anti-human CD3 antibody is administered with a number of consecutive days in which there is no antibody administered. In certain embodiments, the dose administered is the same each day of the regimen. However, in preferred embodiments the dose administered escalates over the first few days of the regimen (e.g., escalates over the first four days of the regimen) to reduce or eliminate the incidence of cytokine release syndrome.

In specific embodiments, the dose administered is approximately 5-50 µg/kg/day, preferably, 20-30 µg/kg/day, more preferably, approximately 22-28 µg/kg/day or approximately 25-26 µg/kg/day. In other specific embodiments, the dose on day 1 of the regimen is 1-3 µg/kg/day, preferably approximately 1.6 µg/kg/day and escalates to the daily dose by day 3, 4, 5, 6 or 7. For example, on day 1, the subject is administered a dose of approximately 1.6 µg/kg/day, on day 2 approximately 3.2 µg/kg/day, on day 3 approximately 6.5 µg/kg/day, on day 4 approximately 13 µg/kg/day and on subsequent days of the regimen 26 µg/kg/day. In another example in accordance with this embodiment, on day 1, the subject may be administered a dose of approximately 1.42 µg/kg/day, on day 2 approximately 5.7 µg/kg/day, on day 3 approximately 11 µg/kg/day, on day 4 approximately 22.6 µg/kg/day and on subsequent days of the regimen 45.4 µg/kg/day.

In specific embodiments, the dose administered is based on surface area. For example the dose administered is 5-1200 µg/m$^2$/day, preferably, 51-826 µg/m$^2$/day. In certain embodiments, the dose on day 1 of the regimen is 5-100 µg/m$^2$/day and escalates to the daily dose that is approximately 2, 4, 5, 8, 10, 12, 15 or 20 times that of the first day dose, for example a dosage as recited immediately above, by day 3, 4, 5, 6 or 7. For the first 2, 3, 4, or 5 days, the dose may increase by 1.5-fold, 2-fold, 3-fold, or 4-fold on each subsequent day. For example, on day 1, the subject is administered a dose of approximately 51 µg/m$^2$/day, on day 2 approximately 103 µg/m$^2$/day, on day 3 approximately 207 µg/m$^2$/day, on day 4 approximately 413 µg/m$^2$/day and on subsequent days of the regimen (e.g., days 5-14) 826 µg/m$^2$/day. In another embodiment, on day 1, the subject is administered a dose of approximately 227 µg/m$^2$/day, on day 2 approximately 459 µg/m$^2$/day, on day 3 and subsequent days, approximately 919 µg/m$^2$/day. In another embodiment, on day 1, the subject is administered a dose of approximately 284 µg/m$^2$/day, on day 2 approximately 574 µg/m$^2$/day, on day 3 and subsequent days, approximately 1148 µg/m$^2$/day.

In specific embodiments, to reduce the possibility of cytokine release and other adverse effects, the first 1, 2, 3, or 4 doses or all the doses in the regimen are administered more slowly, relative to bolus injection, by intravenous administration. For example, a dose of 51 µg/m$^2$/day may be administered over about 5 minutes, about 15 minutes, about 30 minutes, about 45 minutes, about 1 hour, about 2 hours, about 4 hours, about 6 hours, about 8 hours, about 10 hours, about 12 hours, about 14 hours, about 16 hours, about 18 hours, about 20 hours, and about 22 hours. In certain embodiments, the dose is administered by slow infusion over a period of, e.g., 20 to 24 hours. In specific embodiments, the dose is infused by a pump, preferably increasing the concentration of antibody administered as the infusion progresses.

Alternatively, the total daily dose may be divided into two or more equal portions and administered as bolus infusions over the day at intervals of 6, 8, 10 or 12 hours. For example, a 13 µg/kg/day dose may be administered in four doses of 3-4 µg/kg at intervals of 6 hours to reduce the level of cytokine release caused by administration of the antibody.

In other embodiments, a set fraction of the doses for the 51 µg/m$^2$/day to 826 µg/m$^2$/day regimen described above is administered in escalating doses. In certain embodiments, the fraction is 1/10, 1/4, 1/3, 1/2, 2/3 or 3/4 of the daily doses of the regimen(s) described above. Accordingly, for example, when the fraction is 1/10, the daily doses will be 5.1 µg/m$^2$ on day 1, 10.3 µg/m$^2$ on day 2, 20.7 µg/m$^2$ on day 3, 41.3 µg/m$^2$ on day 4 and 82.6 µg/m$^2$ on days 5 to 14. When the fraction is 1/4, the doses will be 12.75 µg/m$^2$ on day 1, 25.5 µg/m$^2$ on day 2, 51 µg/m$^2$ on day 3, 103 µg/m$^2$ on day 4, and 207 µg/m$^2$ on days 5 to 14. When the fraction is 1/3, the doses will be 17 µg/m$^2$ on day 1, 34.3 µg/m$^2$ on day 2, 69 µg/m$^2$ on day 3, 137.6 µg/m$^2$ on day 4, and 275.3 µg/m$^2$ on days 5 to 14. When the fraction is 1/2, the doses will be 25.5 µg/m$^2$ on day 1, 51 µg/m$^2$ on day 2, 103 µg/m$^2$ on day 3, 207 µg/m$^2$ on day 4, and 413 µg/m$^2$ on days 5 to 14. When the fraction is 2/3, the doses will be 34 µg/m$^2$ on day 1, 69 µg/m$^2$ on day 2, 137.6 µg/m$^2$ on day 3, 275.3 µg/m$^2$ on day 4, and 550.1 µg/m$^2$ on days 5 to 14. When the fraction is 3/4, the doses will be 38.3 µg/m$^2$ on day 1, 77.3 µg/m$^2$ on day 2, 155.3 µg/m$^2$ on day 3, 309.8 µg/m$^2$ on day 4, and 620 µg/m$^2$ on days 5 to 14. In other embodiments, the regimen is identical to one of those described above but only over days 1 to 4, days 1 to 5, or days 1 to 6. For example, in a particular embodiment, the doses will be 17 µg/m$^2$ on day 1, 34.3 µg/m$^2$ on day 2, 69 µg/m$^2$ on day 3, 137.6 µg/m$^2$ on day 4, and 275.3 µg/m$^2$ on days 5 and 6.

In other embodiments, doses in the regimen are administered for a certain number of consecutive days, followed by a certain number of days without any doses administered, followed again by doses administered on a certain number of consecutive days and so on until, for example, 14 (or, e.g., 6, 7, 8, 9, 10, 11, 12, 13, 15, 16, 17, 18, 19 or 20) doses are administered in total. For example, the day 1, day 2, day 3 and day 4 doses of one of the regimens described above may be administered over four consecutive days and then three days without any doses and then the day 5, 6, 7 and 8 doses are administered, followed by another three days without doses, and then the day 9, 10, 11, 12 day doses, with three days off, and finally the day 13 and 14 doses.

In certain embodiments, the antibody administered according to these regimens is OKT3γ1 (ala-ala). In other embodiments the antibody is not OKT3γ1 (ala-ala) and is administered so as to achieve one or more pharmacokinetic parameters achieved by the administration of OKT3γ1 (ala-ala), preferably, intravenous administration of OKT3γ1 (ala-ala), such as the serum titer of the antibody administered at 1 day, 2 days, 3 days, 4 days, 5 days, 6 days, 7 days, 2 weeks, 3 weeks or 1 month after the last day of the dosing regime (i.e., is administered to achieve a "pharmacologically equivalent" dose).

In certain embodiments, the anti-human CD3 antibody is administered so as to achieve a certain level of combined coating and modulation of T cell receptor complexes on T cells, as determined by methods well known in the art, see, e.g., Example 11 of U.S. patent application publication US 2003/0108548, which is hereby incorporated by reference in its entirety. In specific embodiments, the dosing regimen achieves a combined T cell receptor coating and modulation of at least 50%, 60%, 70%, 80%, 90%, 95% or of 100% with, in specific embodiments, little to no detectable free anti-human CD3 antibody (for example, less than 200 ng/mL the drug detected in the blood of the patient by standard methods known in the art).

In specific embodiments, the anti-human CD3 antibody is not administered by daily doses over a number of days, but is rather administered by infusion in an uninterrupted manner over 4 hours, 6 hours, 8 hours, 10 hours, 12 hours, 15 hours, 18 hours, 20 hours, 24 hours, 30 hours or 36 hours. The infusion may be constant or may start out at a lower dosage for, for example, the first 1, 2, 3, 5, 6, or 8 hours of the infusion and then increase to a higher dosage thereafter. Over the course of the infusion, the patient receives a dose equal to the amount administered, for example, in the 5 to 20 day regimens set forth above. For example, a dose of approximately 150 µg/m$^2$, 200 µg/m$^2$, 250 µg/m$^2$, 500 µg/m$^2$, 750 µg/m$^2$, 1000 µg/m$^2$, 1500 µg/m 2, 2000 µg/m$^2$, 3000 µg/m$^2$, 4000 µg/m$^2$, 5000 µg/m$^2$, 6000 µg/m$^2$, 7000 µg/m$^2$, 8000 µg/m$^2$, or 9000 µg/m$^2$. In particular, the speed and duration of the infusion is designed to minimize the level of free anti-human CD3 antibody in the subject after administration. In certain embodiments, the level of free anti-human CD3 antibody should not exceed 200 ng/ml free antibody. In addition, the infusion is designed to achieve a combined T cell receptor coating and modulation of at least 50%, 60%, 70%, 80%, 90%, 95% or of 100%.

In other embodiments, the anti-human CD3 antibody is administered chronically to treat, manage, maintain, prevent, or slow the progression of or delay the onset of the autoimmune disease or disorder. For example, in certain embodiments, a low dose of the anti-human CD3 antibody is administered once a month, twice a month, three times per month, once a week or even more frequently either as an alternative to the 6 to 14 day dosage regimen discussed above or after administration of such a regimen to enhance or maintain its therapeutic effect. Such a low dose may be anywhere from 1 µg/m$^2$ to 100 µg/m$^2$, preferably, approximately 5 µg/m$^2$, 10 µg/m$^2$, 15 µg/m$^2$, 20 µg/m$^2$, 25 µg/m$^2$, 30 µg/m$^2$, 35 µg/m$^2$, 40 µg/m$^2$, 45 µg/m$^2$, or 50 µg/m$^2$. In certain embodiments, the anti-human CD3 antibody is administered chronically subsequent to administration of a 1 to 30 day dosing regimen as described above, for example, to maintain the therapeutic effect of the regimen.

In other embodiments, the subject may be re-dosed at some time subsequent to administration of the anti-human CD3 antibody dosing regimen, preferably, based upon one or more physiological parameters, but may be done as a matter of course. Such redosing may be administered and/or the need for such redosing evaluated 6 months, 9 months, 1 year, 15 months, 18 months, 2 years, 30 months or 3 years after administration of a dosing regimen and may include administering a course of treatment every 6 months, 9 months, 1 year, 15 months, 18 months, 2 years, 30 months or 3 years.

In specific embodiments, subjects are administered a subsequent round of anti-human CD3 antibody treatment based upon one or a combination of the CD4/CD8 cell ratio, CD8 cell count, CD4/CD3 inversion, CD4/CD25 cell ratio, CD4/FoxP3 cell ratio, CD4/CD40 cell ratio, CD4/IL-10 cell ratio, and/or CD4/TGF-β cell ratio. Other parameters for determining whether to administer a subsequent round of treatment include an appearance or worsening of diagnostic indicators for the autoimmune disease or disorder as described herein and/or known in the art. For example, with respect to Type I diabetes, an appearance or an increase in anti-islet cell antibodies, such as GADAs, IA-2 antibodies, ICA antibodies or anti-insulin antibodies or an appearance or increase in the levels of T cells specific for islet cell antigens. Further examples with respect to Type I diabetes include subsequent doses where the number of β-cells or β-cell activity or function decreases by 20%, 30%, 40%, 50%, 60%, 70%, 80% or 90% as compared to the β-cell number or activity or function during administration of the preceding round of treatment. β-cell function may be determined by any method know in the art, for example, the C peptide response to MMTT, OGTT, IGTT, or two-phase glucose clamp, or the First Phase Insulin Release (FPIR) test, as discussed herein or as is known in the art. Other parameters that may be used to determine whether to redose during the treatment or management of Type I diabetes include the HA1 or HA1c levels, the need for administration of exogenous insulin or increase in the dosage of exogenous insulin by more than 0.2 U/kg/day, 0.5 U/kg/day, 1 U/kg/day, 2 U/kg/day, 5 U/kg/day, or 10 U/kg/day. In other embodiments, the further doses may be administered based upon appearance of or increase in number (such as an increase by, on average, 1, 2, 3, 4, 5, 8, 10 15, or 20), duration and/or severity of hypoglycemic episodes or of ketoacidosis episodes on a daily, weekly or monthly basis.

In preferred embodiments, the anti-human CD3 antibodies are administered parenterally, for example, intravenously, intramuscularly or subcutaneously, or, alternatively, are administered orally. The anti-human CD3 antibodies may also be administered as a sustained release formulation.

Additionally, in certain embodiments, the invention provides methods and regimens of administering anti-human CD3 antibodies that reduce the severity and/or incidence of adverse effects such as, but not limited to, cytokine release, apoptosis, activation of EBV, immune reaction against the anti-human CD3 antibody, lymphopenia, anemia, neutropenia, thrombocytopenia or secondary infection.

In preferred embodiments of their invention, with respect to treating, slowing the progression of, delaying the onset of or preventing type 1 diabetes or disorder, the subject has retained at least 95%, 90%, 80%, 70%, 60%, 50%, 40%, 30% or 20% β-cell function prior to initiation of treatment and, in some embodiments, β-cell function improves over pre-treatment levels by at least 5%, 10%, 20%, 30% or 40%.

In certain embodiments, the predisposition for development of Type I diabetes manifests as an impaired fasting glucose level, i.e., at least one determination of a glucose level of 100-125 mg/dL after fasting (eight hours without food), or is an impaired glucose tolerance in response to a 75 gram oral glucose tolerance test (OGTT), i.e., at least one determination of a 2-hour glucose level of 140-199 mg/dL in response to a 75 OGTT. In other embodiments, the subjects are positive for one or more autoantibodies reactive against islet cell antigens, such as, GAD antibodies, such as GAD 65 and/or GAD 67, IA-2 or anti-insulin antibodies. In other embodiments, the predisposition for development of type 1 diabetes is having a first or second degree relative who is a diagnosed type 1 diabetic. In certain embodiments, the predisposition is positive diagnosis in the patient or in a first or second degree relative according to art accepted criteria of at least one other autoimmune disorder including, but not limited to, thyroid disease, type 1 diabetes, rheumatoid arthritis, systemic lupus erythematosus, multiple endocrine adenopathy, and celiac disease. In some embodiments, the autoimmune disorder is a MHC DR3- and/or a DR4-related autoimmune disease.

With respect to treatment of type 1 diabetes in a diagnosed patient, and the prevention/delay of symptoms thereof in a predisposed individual, the anti-human CD3 antibody with reduced toxicity is administered to achieve, or maintain a level of glycosylated hemoglobin (HA1 or HA1c) of less than 8%, less than 7.5%, less than 7%, less than 6.5%, less than 6%, less than 5.5% or 5% or less. At the initiation of treatment, patients preferably, have a HA1 or HA1c level of less than 8%, less than 7.5%, less than 7%, less than 6.5%, less than 6%, or, more preferably, from 4%-6% (preferably, measured in the absence of other treatment for diabetes, such as administration of exogenous insulin).

In certain embodiments, one or more CD3 binding molecules (e.g., one or more anti-human CD3 antibodies) are administered to prevent a reduction of β-cell mass associated with autoimmune diabetes. In some embodiments, after one or more courses of treatment with an anti-human CD3 antibody according to the invention, the level of β-cell mass of the patient decreases by less than 1%, less than 5%, less than 10%, less than 20%, less than 30%, less than 40%, less than 50%, less than 60%, or less than 70% of the pretreatment levels of at least 3 months, at least 6 months, at least 9 months, at least 1 year, at least 18 months, at least 2 years, at least 3 years, at least 5 years, at least 7 years or at least 10 years after initial treatment. In yet another embodiment of the invention, after one or more courses of treatment with an anti-CD3 antibody according to the invention, the level of β-cell mass of the patient is maintained at least 99%, at least 95%, at least 90%, at least 80%, at least 70%, at least 60%, at least 50%, at least 40%, or at least 30% of pretreatment levels for at least 4 months, at least 6 months, at least 9 months, at least 12 months, at least 18 months, at least 24 months, at least 30 months, at least 3 years, at least 5 years, or at least 10 years after the first round of treatment.

In another embodiment of the invention, with respect to the treatment of type 1 diabetes, after one or more courses of treatment with an anti-CD3 antibody according to the invention the level of β-cell function of the patient is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment or after the first round of treatment and the mean lymphocyte count of the patient is not less than 800 cells/ml, less than 750 cells/ml, less than 700 cells/ml, less than 650 cells/mil, less than 600 cells/ml, less than 550 cells/ml, less than 500 cells/ml, less than 400 cells/ml, less than 300 cells/ml or less than 200 cells/ml at the same time period. In another embodiment of the invention, after a course of treatment with an anti-CD3 antibody according to the invention, the level of β-cell function of the patient is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment and the mean platelet count of the patient is not less than 100,000,000 platelets/ml, less than 75,000,000 platelets/ml, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/ml or less than 100,000 platelets/ml.

The administration of the anti-CD3 antibodies prevents damage to islet cells, thereby delaying onset of the disease or, once diagnosable disease occurs, disease progression, reducing and/or delaying the need for insulin administration. In addition, the invention provides methods of treatment such that a single round of treatment or round of treatment every 6 months, every 9 months, every 12 months, every 15 months, every 18 months, or every 24 months with an anti-CD3 antibody (preferably, without any intervening treatment with anti-CD3 antibodies), results in a level of HA1 or HA1c that is 7% or less, 6.5% or less, 6% or less, 5.5% or less, or 5% or less 6 months, 9 months, 12 months, 15 months, 18 months, or 24 months after the previous round of treatment or the first round of treatment. Specifically, in such methods of the invention a single round of treatment or round of treatment every 6 months, every 9 months, every 12 months, every 15 months, every 18 months, or every 24 months with an anti-CD3 antibody (preferably, without any intervening treatment with anti-human CD3 antibodies), decreases the average level of HA1 or HA1c in the patient by about 5%, about 10%, about 15%, about 20%, about 25%, about 30%, about 35%, about 40%, about 45%, about 50%, about 55%, about 60%, about 65% or about 70% as compared to pre-treatment levels at 6 months, 9 months, 12 months, 15 months, 18 months, or 24 months after the previous round of treatment or first round of treatment. In addition, after treatment with a CD3 antibody according to the invention in a single round of treatment or a round of treatment repeated every 6 months, every 9 months, every 12 months, every 15 months, every 18 months, or every 24 months (preferably, without any intervening treatment with anti-human CD3 antibodies), the average level of HA1 or HA1c in the patient only increases by about 0.5%, about 1%, about 2.5%, about 5%, about 10%, about 15%, about 20%, about 25%, about 30%, about 35%, about 40%, about 45%, or about 50% as compared to pre-treatment levels at 6 months, 9 months, 12 months, 15 months, 18 months, or 24 months after the previous round of treatment or the first round of treatment. In other embodiments, after a single round of treatment or rounds of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the average level of HA1 or HA1c in the patient is greater than about 10%, about 20%, about 30%, about 40%, about 50%, about 60%, about 70% or greater than about 100% less than the levels in a patient that initiated conventional treatment with similar clinical parameters and was administered conventional treatment after the same amount of time, which levels were determined at 6 months, 9 months, 12 months, 15 months, 18 months, or 24 months after the previous round of treatment or the first round of treatment.

In another embodiment, the anti-human CD3 antibody is administered to achieve, or maintain the C-peptide response in a subject who has been diagnosed with autoimmune diabetes, or has a predisposition thereto, as determined by a mixed-meal tolerance test (MMTT), oral glucose tolerance test (OGTT), intravenous tolerance test (IGTT) or two-phase glucose clamp procedure. In preferred embodiments, the patients have a C-peptide response to MMTT, OGTT, IGTT, or two-phase glucose clamp procedure (preferably MMTT) resulting in an area under curve (AUC) of at least 80 μmol/ml/240 min., preferably, at least 90 μmol/ml/240 min., more preferably at least 100 μmol/ml/240 min., or even at least 110 μmol/ml/240 min. In addition, the invention provides methods of treatment such that after a single round of treatment or treatment every 6 months, every 9 months, every 12 months, every 15 months, every 18 months, or every 24 months with an anti-human CD3 antibody (preferably, without any intervening treatment with anti-human CD3 antibodies), the level of C-peptide response in the patient is at least 99%, at least 98%, at least 95%, at least 90%, at least 85%, at least 80%, at least 75%, at least 70%, at least 65% or at least 60% of the pre-treatment response as determined at 6 months, 9 months, 12 months, 15 months, 18 months, or 24 months after the previous round of treatment or the first round of treatment. Specifically, in such methods of the invention, after a single round of treatment or round of treatment every 6 months, every 9 months, every 12 months, every 15 months, every 18 months, or every 24 months with an anti-human CD3 antibody according to methods of the invention (preferably, without any intervening treatment with anti-human CD3 antibodies), the average level of C-peptide response to a MMTT, OGTT, IGTT, or two-phase glucose clamp procedure in the patient decreases by less than 1%, less than 5%, less than 10%, less than 20%, less than 30%, less than 40%, less than 50% of the pre-treatment levels as determined at 6 months, 9 months, 12 months, 15 months, 18 months, or 24 months after the previous round of treatment or the first round of treatment. In addition, after a single round of treatment or round of treatment every 6 months, every 9 months, every 12 months, every 15 months, every 18 months, or every 24 months with an anti-human CD3 antibody according to methods of the invention (preferably, without any intervening treatment with anti-human CD3 antibodies), the average level of C-peptide response to a MMTT, OGTT, IGTT or two-phase glucose clamp procedure in the patient is at least 10%, 20%, 30%, 40%, 50%, 70% or 100% greater than the levels in a patient who initiated conventional diabetes therapy with similar clinical parameters and was administered conventional diabetes therapy over the 6 month, 9 month, 12 month, 15 month or 18 month period or who did not receive any therapy, said peptide response being determined at 6 months, 9 months, 12 months, 15 months, 18 months, or 24 months after the previous treatment.

In specific embodiments, after a single round of treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the patients diagnosed with autoimmune diabetes, or having a predisposition thereto, have a C-peptide response to MMTT, OGTT, IGTT or two-phase glucose clamp procedure (preferably, MMTT) resulting in an AUC of at least 40 μmol/ml/240 min., 50 μmol/ml/240 min, 60 μmol/ml/240 min, 70 μmol/ml/240 min., 80 μmol/ml/240 min., preferably, at least 90 μmol/ml/240 min., more preferably at least 100 μmol/ml/240 min., or even at least 110 μmol/ml/240 min, said response determined 6 months, 9 months, 12 months, 15 months, 18 months, or 24 months after the previous round of treatment or after the previous round of treatment.

The determination of C-peptide response is a measure of β-cell function as is known to one skilled in the art. In other embodiments, β-cell function or residual β-cell function is determined by First-Phase Insulin Release (FPIR). In preferred embodiments, the patients prior to treatment with an anti-human CD3 antibody according to the invention have a FPIR of at least 300 μmol/l, at least 350 μmol/l, at least 400 μmol/l, at least 450 μmol/l, at least 500 μmol/l, preferably, at least 550 μmol/l, more preferably at least 600 μmol/l, or even at least 700 μmol/l. In addition, the invention provides methods of treatment such that after a single round of treatment or a round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the FPIR is at least 99%, at least 98%, at least 95%, at least 90%, at least 85%, at least 80%, at least 75%, at least 70%, at least 65% or at least 60% of the pre-treatment response, said FPIR determined 6 months, 9 months, 12 months, 15 months, 18 months, or 24 months after the previous treatment or initial treatment. Specifically, in such methods of the invention, after a single round of treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the average FPIR in the patient decreases by less than 1%, less than 5%, less than 10%, less than 20%, less than 30%, less than 40%, less than 50% of the pre-treatment levels, said FPIR determined 6 months, 9 months, 12 months, 15 months, 18 months, or 24 months after the previous treatment. In addition, after a single round of treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the average FPIR in the patient is at least 10%, 20%, 30%, 40%, 50%, 70% or 100% greater than the levels in a patient who initiated conventional diabetes therapy with similar clinical parameters and was administered conventional diabetes therapy over the 6 month, 9 month, 12 month, 15 month or 18 month period, said FPIR determined 6 months, 9 months, 12 months, 15 months, 18 months, or 24 months after the previous treatment or initial round of treatment. In specific embodiments, after a single round of treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the patients have a FPIR of at least 300 μmol/l, at least 400 μmol/l, preferably, at least 500 μmol/l, more preferably at least 600 μmol/l, or even at least 700 μmol/l, said FPIR determined at 6 months, 9 months, 12 months, 15 months, 18 months, or 24 months after the previous round of treatment or initial round of treatment.

In other specific embodiments of the invention with respect to the treatment of type 1 diabetes, at the initiation of treatment, the subject does not require administration of insulin or requires less than 1 U/kg/day, preferably less than 0.5 u/kg/day, even more preferably less than 0.25 U/kg/day, and even more preferably less than 0.1 U/kg/day. In certain embodiments, a single treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), prevents the requirement for administration of insulin or delays the need to administer insulin by at least 6 months, at least 1 year, at least 18 months, at least 2 years, at least 30 months, at least 3 years, at least 5 years, at least 7 years or at least 10 years (on average for a population of type 1 diabetes patients). In other embodiments, a single treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), results in either a decrease (for example, of 10%, 20%, 30%, 40%, or 50%) in the amount of insulin required on average per day, or no change in the average amount of insulin required per day, or an increase of less than 1%, less than 5%, less than 10%, less than 20% or less than 30% of insulin administered, on average, per day as compared to the pre-treatment average dose of insulin per day. In certain embodiments, a single round of treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), results in an average daily dose of insulin that is 10%, 20%, 50%, 75%, 90%, 99% less than the average daily dose of insulin required for a patient similarly situated (i.e., similar chemical parameters at the beginning of the month or year period) that had not received the anti-human CD3 antibody treatment.

In other embodiments, with respect to the treatment of a subject diagnosed with autoimmune diabetes, or has a predisposition thereto, the methods of the invention result in a reduction in hypoglycemic episodes by 1, 2, 3, 4, 5, 6 or more episodes in a one-day, two-day, 5-day, 10-day or 15-day period as compared to similarly situated patients not having been administered the anti-human CD3 antibody according to the invention.

In specific embodiments, the subject has received transplanted islet cells and is administered a prophylactically or therapeutically effective amount of the anti-CD3 antibody according to the methods of the invention. In a specific embodiment, the subject having received transplanted islet cells is an adult. In other specific embodiments, the subject having received the transplanted islet cells is younger than 21 years of age or is younger than 18 years of age.

With respect to the treatment of multiple sclerosis, the anti-CD3 antibody is administered to achieve or maintain a disability score according to the Kurtzke Expanded Disability Scale (EDSS) of 1.0, 1.5, 2.0, 2.5, 3.0, 3.5, 4.0, 4.5, 5.0, 5.5, 6.0, 6.5, 7.0, 7.5, 8.0, 8.5, or 9.0. In addition, the invention provides methods such that after a single treatment or treatment every 6 months, every 9 months, every 12 months, every 15 months, every 18 months, every 2 years, every 2.5 years or every 3 years with an anti-CD3 antibody according to the methods of the invention (preferably, without any intervening treatment with anti-CD3 antibodies), the EDSS score is the same, not more than one-half step, not more than one step, not more than one and one-half steps, not more than two steps, not more than two and one-half steps, not more than three steps, not more than three and one-half steps, not more than four steps, not more than four an one-half steps, not more than more than five steps, not more than five and one-half steps, not more than six steps, not more than six and one-half steps, not more than seven steps, not more than seven and one-half steps, not more than eight steps, or not more than eight and one-half steps greater that the pretreatment EDSS score, said score determined 6 months, 9 months, 12 months, 15 months, 18 months, or 24 months after the previous treatment. Specifically, in such methods of the invention, after a single treatment or treatment every 6 months, every 9 months, every 12 months, every 15 months, every 18 months, every 2 years, every 2.5 years or every 3 years with an anti-CD3 antibody according to the methods of the invention (preferably, without any intervening treatment with anti-CD3 antibodies), the average EDSS score of the patient increases by no more than one-half step, one step, one and one-half steps, two steps, two and one-half steps, three steps, three and one-half steps, four steps, four an one-half steps, five steps, five and one-half steps, six steps, six and one-half steps, seven steps, seven and one-half steps, eight steps, or eight and one-half steps relative to the pre-treatment score, said score determined 6 months, 9 months, 12 months, 15 months, 18 months, or 24 months after the previous treatment. In addition, after a single treatment or treatment every 6 months, every 9 months, every 12 months, every 15 months, every 18 months, every 2 years, every 2.5 years or every 3 years with an anti-CD3 antibody according to the methods of the invention (preferably, without any intervening treatment with anti-CD3 antibodies), the average EDSS score in the patient is at least one-half step, one step, one and one-half steps, two steps, two and one-half steps, three steps, three and one-half steps, four steps, four an one-half steps, five steps, five and one-half steps, six steps, six and one-half steps, seven steps, seven and one-half steps, eight steps, or eight and one-half lower than the score in a patient who initiated conventional multiple sclerosis therapy with similar clinical parameters and was administered conventional multiple sclerosis therapy over the 6 months, 9 months, 12 months, 15 months, 18 months, 2 year, 2.5 year or 3 year period, said score determined 6 months, 9 months, 12 months, 15 months, 18 months, or 24 months after the previous treatment. In specific embodiments, 6 months, 9 months, 12 months, 15 months, 18 months, 2 years, 2.5 years or 3 years after treatment (preferably, without any intervening treatment with anti-CD3 antibodies), the patients have an EDSS score of at least 1.0, 1.5, 2.0, 2.5, 3.0, 3.5, 4.0, 4.5, 5.0, 5.5, 6.0, 6.5, 7.0, 7.5, 8.0, 8.5, or 9.0.

In specific embodiments of the invention, patients diagnosed with multiple sclerosis (e.g., according to McDonald criteria), and prior to administration of the anti-CD3 antibody of the invention have an EDSS score of at least 1.0, 1.5, 2.0, 2.5, 3.0, 3.5, 4.0, 4.5, 5.0, 5.5, 6.0, 6.5, 7.0, 7.5, 8.0, 8.5, 9.0 or 9.5.

In other embodiments with respect to the treatment of multiple sclerosis, the anti-CD3 antibody is administered to achieve reduction in the frequency, duration and/or severity of the MS attacks relative to the same patient prior to therapy. In addition, the invention provides methods of treatment such that after a single treatment or treatment every 6 months, every 9 months, every 12 months, every 15 months, every 18 months, every 2 years, every 2.5 years or every 3 years with an anti-CD3 antibody according to the methods of the invention (preferably, without any intervening treatment with anti-CD3 antibodies), the frequency, duration and/or severity of the MS attacks are reduced by 5%, 10%, 20%, 30%, 40%, 50%, 60%, 70%, 80%, or 90% relative to pretreatment levels, said determinations made 6 months, 9 months, 12 months, 15 months, 18 months, or 24 months after the previous treatment. Specifically, in such methods of the invention, after a single treatment or treatment every 6 months, every 9 months, every 12 months, every 15 months, every 18 months, every 2 years, every 2.5 years or every 3 years with an anti-CD3 antibody according to the methods of the invention (preferably, without any intervening treatment with anti-CD3 antibodies), the frequency, severity and/or duration of the MS attacks of the patient increase by no more than 5%, 10%, 20%, 30%, 40%, 50%, 60%, 70%, 80%, or 90% relative to pretreatment conditions, said determinations made at 6 months, 9 months, 12 months, 15 months, 18 months, or 24 months after the previous treatment. In addition, after a single treatment or treatment every 6 months, every 9 months, every 12 months, every 15 months, every 18 months, every 2 years, every 2.5 years or every 3 years with an anti-CD3 antibody according to the methods of the invention (preferably, without any intervening treatment with anti-CD3 antibodies), the average frequency, severity and/or duration of the MS attacks is reduced relative to a patient who initiated conventional multiple sclerosis therapy with similar clinical parameters and was administered conventional multiple sclerosis therapy over the 6 months, 9 months, 12 months, 15 months, 18 months, 2 year, 2.5 year or 3 year period, said determination made at 6 months, 9 months, 12 months, 15 months, 18 months, or 24 months after the previous treatment.

In other embodiments with respect to the treatment of psoriasis, the anti-CD3 antibody is administered to achieve a reduction in the subject's Psoriasis Area and Severity Index (PASI) score by at least 20%, at least 35%, at least 30%, at least 40%, at least 45%, at least 50%, at least 55%, at least 60%, at least 65%, at least 70%, at least 75%, at least 80%, or at least 85% relative to pretreatment conditions, said determinations made at 6 months, 9 months, 12 months, 15 months, 18 months, or 24 months after the previous treatment. Alternatively, the methods of the invention improve the global assessment score of a subject by at least 25%, at least 35%, at least 30%, at least 40%, at least 45%, at least 50%, at least 55%, at least 60%, at least 65%, at least 70%, at least 75%, at least 80%, at least 85%, at least 90%, or at least 95% relative to pretreatment conditions, said determinations made at 6 months, 9 months, 12 months, 15 months, 18 months, or 24 months after the previous treatment.

In other embodiments with respect to the treatment of rheumatoid arthritis, the anti-CD3 antibody is administered to achieve an improvement in the subject's condition as assessed by any arthritis severity scale known in the art (e.g., rheumatoid arthritis severity scale (RASS)) by at least 25%, at least 35%, at least 30%, at least 40%, at least 45%, at least 50%, at least 55%, at least 60%, at least 65%, at least 70%, at least 75%, at least 80%, at least 85%, at least 90%, at least 95%, or at least 100% relative to pretreatment conditions, said determinations made at 6 months, 9 months, 12 months, 15 months, 18 months, or 24 months after the previous treatment.

In certain embodiments, diagnosis of an autoimmune disorder or manifestation of a predisposition of an autoimmune disorder is based on the detection of cytotoxic T-lymphocytes ("CTLs") that recognize donor specific antigens (i.e., autoreactive CTLs) in the peripheral blood of the subject and/or target tissue of the immune disorder. In certain embodiments, the anti-CD3 antibody of the invention is administered to achieve a reduction by at least 10%, at least 20%, at least 35%, at least 30%, at least 40%, at least 45%, at least 50%, at least 55%, at least 60%, at least 65%, at least 70%, at least 75%, at least 80%, or at least 85% in absolute number, or proportion, of the subject's autoreactive CTLs as determined by immunospot assay (e.g., ELISPOT) relative to the pretreatment condition, said determinations made at 6 months, 9 months, 12 months, 15 months, 18 months, or 24 months after the previous treatment.

In preferred embodiments, the patient is under 21 years of age, 18 years of age, under 15 years of age, under 12 years of age, under 9 years of age, or under 5 years of age or from infancy to 3 years of age, from 2 to 5 years of age, from 5 to 9 years of age, from 9 to 12 years of age, from 12 to 20 years of age. In other embodiments, the patient is an adult.

The invention also provides combination therapy methods. The methods of the invention can be carried out in combination with any standard treatment for the particular indication, such as standard immunosuppressant and/or anti-inflammatory treatments administered for the treatment or amelioration of autoimmune diseases. For example, with respect to the treatment of Type 1 diabetes, the anti-human CD3 antibody therapy of the invention may be administered along with other therapies for diabetes, such as, but not limited to, administration of insulin, exenatide, pramlintide or a combination thereof. With respect to the treatment of multiple sclerosis, the anti-human CD3 antibody therapy of the invention may be administered with other therapies known in the art for the treatment of multiple sclerosis, such as, but not limited to, administration of beta interferon (e.g., AVONEX®, BETASERON®, REBIF®), immunosuppressant (e.g., mitoxantrone), myelin basic protein copolymer 1 (e.g., COPAXONE®), or a combination thereof. The CD3 antibodies of the invention may further be administered with other therapies such as anti IL-2 antibodies, cytokine antagonists, and steroidal therapies (for example, but not limited to, glucocorticoids, dexamethasone, cortisone, hydrocortisone, prednisone, prednisolone, triamcinolone, azulfidine, etc.), non-steroidal anti-inflammatories (NSAIDS), such as, but not limited to aspirin, ibuprofen, diclofenac, etodolac, fenoprofen, indomethacin, ketolorac, oxaprozin, nabumetone, sulindac, tolmentin, naproxen, or ketoprofen, immunosuppressants, such as, methotrexate or cyclosporin, and TNF-α inhibitors such as, but not limited to, etanercept and infliximab. In certain embodiments of the invention, subjects which have become refractory to conventional treatments are treated using methods of the invention. In certain embodiments, the anti-human CD3 antibody is administered in combination with one or more islet cell antigens, such as GAD, IA-2 or other antigens which are bound by autoantigens found in patients with type 1 diabetes.

The invention, in other embodiments, provides methods of producing anti-human CD3 antibodies, particularly OKT3 derived antibodies, such as, but not limited to, humanized OKTγ1 (ala-ala), in CHO cells. In particular embodiments, the invention provides methods of producing anti-human CD3 antibodies comprising (a) culturing CHO cells that have been transfected with the expression vector pMGX1303, or progeny thereof, in media under conditions suitable for expression of said anti-human CD3 antibody; and (b) recovering said anti-human CD3 antibody from said media.

3.1 Terminology

As used herein, the term "about" or "approximately," when used in conjunction with a number, refers to any number within 1, 5 or 10% of the referenced number or within experimental error typical of methods used for measurement.

As used herein, the term "analog" in the context of polypeptides refers to a polypeptide that possesses a similar or identical function as a second polypeptide but does not necessarily comprise a similar or identical amino acid sequence of the second polypeptide, or possess a similar or identical structure of the second polypeptide. A polypeptide that has a similar amino acid sequence refers to a second polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second polypeptide; (b) a polypeptide encoded by a nucleotide sequence that hybridizes under stringent conditions to a nucleotide sequence encoding a second polypeptide of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second polypeptide. A polypeptide with similar structure to a second polypeptide refers to a polypeptide that has a similar secondary, tertiary or quaternary structure to the second polypeptide. The structure of a polypeptide can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous analog refers to a second organic or inorganic molecule which possess a similar or identical function as a first organic or inorganic molecule and is structurally similar to the first organic or inorganic molecule.

As used herein, the terms "antagonist" and "antagonists" refer to any protein, polypeptide, peptide, antibody, antibody fragment, large molecule, or small molecule (less than 10 kD) that blocks, inhibits, reduces or neutralizes the function, activity and/or expression of another molecule. In various embodiments, an antagonist reduces the function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

As used herein, the terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "C-peptide" refers to a 31-amino acid peptide cleaved from proinsulin as it is converted to insulin. Proinsulin consists of an A chain, a connecting peptide (C-peptide), and a B chain. After proinsulin is cleaved, C-peptide remains in the secretory granules of beta cells in the pancreas with insulin and is cosecreted with insulin in response to glucose stimulation. C-peptide is thus released from the pancreas in equi-molar amounts with insulin and may be used as a marker of endogenous insulin production.

As used herein, the term "derivative" in the context of polypeptides refers to a polypeptide that comprises an amino acid sequence which has been altered by the introduction of amino acid residue substitutions, deletions or additions. The term "derivative" as used herein also refers to a polypeptide that has been modified, i.e., by the covalent attachment of any type of molecule to the polypeptide. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to specific chemical cleavage, acetylation, formylation, metabolic synthesis of tunicamycin, etc. Further, a derivative polypeptide may contain one or more non-classical amino acids. A polypeptide derivative possesses a similar or identical function as the polypeptide from which it was derived.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs.

As used herein, the term "epitopes" refers to fragments of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "Fc region" is used to define a C-terminal region of an IgG heavy chain. Although the boundaries may vary slightly, the human IgG heavy chain Fc region is defined to stretch from Cys226 to the carboxy terminus. The Fc region of an IgG comprises two constant domains, CH2 and CH3. The CH2 domain of a human IgG Fc region usually extends from amino acids 231 to amino acid 341. The CH3 domain of a human IgG Fc region usually extends from amino acids 342 to 447. The Fc region of an IgG comprises two constant domains, CH2 and CH3. The CH2 domain of a human IgG Fc region (also referred to as "Cγ2" domain) usually extends from amino acid 231-340. The CH2 domain is unique in that it is not closely paired with another domain. Rather, two N-linked branched carbohydrate chains are interposed between the two CH2 domains of an intact native IgG.

Throughout the present specification, the numbering of the residues in an IgG heavy chain is that of the EU index as in Kabat et al., *Sequences of Proteins of Immunological Interest*, 5$^{th}$ Ed. Public Health Service, NH1, MD (1991), expressly incorporated herein by references. The "EU index as in Kabat" refers to the numbering of the human IgG1 EU antibody.

The "hinge region" is generally defined as stretching from Glu216 to Pro230 of human IgG1. Hinge regions of other IgG isotypes may be aligned with the IgG1 sequence by placing the first and last cysteine residues forming inter-heavy chain S—S binds in the same positions.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide.

In a specific embodiment, a fragment of a polypeptide retains at least one function of the polypeptide.

As used herein, the term "functional fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of second, different polypeptide, wherein said peptide or polypeptide retains at least one function of the second, different polypeptide.

As used herein, the term "fusion protein" refers to a polypeptide that comprises an amino acid sequence of a first protein or functional fragment, analog or derivative thereof, and an amino acid sequence of a heterologous protein (i.e., a second protein or functional fragment, analog or derivative thereof different than the first protein or functional fragment, analog or derivative thereof). In particular embodiments, a fusion protein comprises a CD3 binding molecule and a heterologous protein, polypeptide, or peptide.

As used herein, the term "host cell" refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "hybridizes under stringent conditions" describes conditions for hybridization and washing under which nucleotide sequences at least 60% (65%, 70%, preferably 75%, 80% or 85%, and more preferably, 90% or 95%) identical to each other typically remain hybridized to each other. Such stringent conditions are known to those skilled in the art and can be found in *Current Protocols in Molecular Biology*, John Wiley & Sons, N.Y. (1989), 6.3.1-6.3.6. In one, non-limiting example stringent hybridization conditions are hybridization at 6× sodium chloride/sodium citrate (SSC) at about 45° C., followed by one or more washes in 0.1×SSC, 0.2% SDS at about 68° C. In a preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides.

As used herein, the term "hypoglycemic episode" refers to a blood glucose level in a subject of less than 60 mg/dL that results in typical symptoms of hypoglycemia such as sweatiness, nausea, blurred vision (e.g., seeing spots), shakiness, numb lips and/or tongue, irritability, fainting, clammy skin, confusion, nervousness, weakness, and/or rapid heart beat.

As used herein, the term "immunomodulatory agent" and variations thereof refer to an agent that modulates a host's immune system. In certain embodiments, an immunomodulatory agent is an immunosuppressant agent. In certain other embodiments, an immunomodulatory agent is an immunostimulatory agent. Immunomodulatory agents include, but are not limited to, small molecules, peptides, polypeptides, fusion proteins, antibodies, inorganic molecules, mimetic agents, and organic molecules.

As used herein, the term "immunospecifically binds to an antigen" and analogous terms refer to peptides, polypeptides, fusion proteins and antibodies or fragments thereof that specifically bind to an antigen or a fragment and do not specifically bind to other antigens. A peptide or polypeptide that immunospecifically binds to an antigen may bind to other peptides or polypeptides with lower affinity as determined by, e.g., immunoassays, BIAcore, or other assays known in the art. Antibodies or fragments that immunospecifically bind to an antigen may cross-reactive with related antigens. Preferably, antibodies or fragments that immunospecifically bind to an antigen do not cross-react with other antigens.

As used herein, the term "immunospecifically binds to a CD3 polypeptide" and analogous terms refer to peptides, polypeptides, fusion proteins and antibodies or fragments thereof that specifically bind to a CD3 polypeptide or a fragment thereof and do not specifically bind to other polypeptides. A peptide or polypeptide that immunospecifically binds to a CD3 polypeptide may bind to other peptides or polypeptides with lower affinity as determined by, e.g., immunoassays, BIAcore, or other assays known in the art. Antibodies or fragments that immunospecifically bind to a CD3 polypeptide may be cross-reactive with related antigens. Preferably, antibodies or fragments that immunospecifically bind to a CD3 polypeptide or fragment thereof do not cross-react with other antigens. Antibodies or fragments that immunospecifically bind to a CD3 polypeptide can be identified, for example, by immunoassays, BIAcore, or other techniques known to those of skill in the art. An antibody or fragment thereof binds specifically to a CD3 polypeptide when it binds to a CD3 polypeptide with higher affinity than to any cross-reactive antigen as determined using experimental techniques, such as radioimmunoassays (RIA) and enzyme-linked immunosorbent assays (ELISAs). See, e.g., Paul, ed., 1989, *Fundamental Immunology Second Edition*, Raven Press, New York at pages 332-336 for a discussion regarding antibody specificity.

As used herein, the term "in combination" refers to the use of more than one prophylactic and/or therapeutic agent. The use of the term "in combination" does not restrict the order in which prophylactic and/or therapeutic agents are administered to a subject with a disease or disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject with a disease or disorder.

As used herein, the term "isolated" in the context of a peptide, polypeptide, fusion protein or antibody refers to a peptide, polypeptide, fusion protein or antibody which is substantially free of cellular material or contaminating proteins from the cell or tissue source from which it is derived, or substantially free of chemical precursors or other chemicals when chemically synthesized. The language "substantially free of cellular material" includes preparations of a peptide, polypeptide, fusion protein or antibody in which the peptide, polypeptide, fusion protein or antibody is separated from cellular components of the cells from which it is isolated or recombinantly produced. Thus, a peptide, polypeptide, fusion protein or antibody that is substantially free of cellular material includes preparations of a peptide, polypeptide, fusion protein or antibody having less than about 30%, 20%, 10%, or 5% (by dry weight) of heterologous protein (also referred to herein as a "contaminating protein"). When the peptide, polypeptide, fusion protein or antibody is recombinantly produced, it is also preferably substantially free of culture medium, i.e., culture medium represents less than about 20%, 10%, or 5% of the volume of the protein preparation. When the peptide, polypeptide, fusion protein or antibody is produced by chemical synthesis, it is preferably substantially free of chemical precursors or other chemicals, i.e., it is separated from chemical precursors or other chemicals which are involved in the synthesis of the peptide, polypeptide, fusion protein or antibody. Accordingly such preparations of a peptide, polypeptide, fusion protein or antibody have less than about 30%, 20%, 10%, 5% (by dry weight) of chemical precursors or compounds other than the peptide, polypeptide, fusion protein or antibody of interest. In a preferred embodiment, a CD3 binding molecule is isolated. In another preferred embodiment, an anti-human CD3 antibody is isolated.

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized and may be free of cDNA or other genomic DNA molecules, e.g., has been isolated from other clones in a nucleic acid library. In a preferred embodiment, a nucleic acid molecule encoding a CD3 binding molecule is isolated. In another preferred embodiment, a nucleic acid molecule encoding an anti-human CD3 antibody is isolated.

As used herein, the terms "non-responsive" and refractory" describe patients treated with a currently available prophylactic or therapeutic agent for an autoimmune disorder which is not clinically adequate to relieve one or more symptoms associated with the autoimmune disorder. Typically, such patients suffer from severe, persistently active disease and require additional therapy to ameliorate the symptoms associated with their autoimmune disorder.

As used herein, the term "onset" of disease with reference to Type-1 diabetes refers to a patient meeting the criteria established for diagnosis of Type-1 diabetes by the American Diabetes Association (see, Mayfield et al., 2006, Am. Fam. Physician 58:1355-1362).

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the terms "prophylactic agent" and "prophylactic agents" refer to CD3 binding molecules which can be used in the prevention, treatment, management or amelioration of one or more symptoms of an autoimmune disease. In certain embodiments, the term "prophylactic agent" refers to anti-human CD3 antibodies (e.g., OKT3 and variants and derivatives thereof).

As used herein, the term "prophylactically effective amount" refers to that amount of a CD3 binding molecule sufficient to prevent the development, recurrence or onset of one or more symptoms of a disorder. In certain embodiments, the term "prophylactically effective amount" refers to the amount of an anti-human CD3 antibody sufficient to prevent the development, recurrence or onset of one or more symptoms of a disorder.

As used herein, the terms "prevent", "preventing" and "prevention" refer to the prevention of the recurrence or onset of one or more symptoms of an autoimmune or inflammatory disorder in a subject resulting from the administration of a prophylactic or therapeutic agent.

As used herein, a "protocol" includes dosing schedules and dosing regimens. The protocols herein are methods of use and include prophylactic and therapeutic protocols. A "dosing regimen" or "course of treatment" may include administration of several doses of a therapeutic or prophylactic agent over 1 to 20 days.

As used herein, the phrase "side effects" encompasses unwanted and adverse effects of a prophylactic or therapeutic agent. Adverse effects are always unwanted, but unwanted effects are not necessarily adverse.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey or a human), and more preferably a human.

As used herein, the term "synergistic" refers to a combination of prophylactic or therapeutic agents which is more effective than the additive effects of the agents in the combination when administered individually. A synergistic effect of a combination of prophylactic or therapeutic agents may permit the use of lower dosages of one or more of the agents and/or less frequent administration of said agents to a subject with an autoimmune disorder. The ability to utilize lower dosages of prophylactic or therapeutic agents and/or to administer said agents less frequently reduces the toxicity associated with the administration of said agents to a subjected without reducing the efficacy of said agents in the prevention or treatment of autoimmune disorders. In addition, a synergistic effect can result in improved efficacy of agents in the prevention or treatment of autoimmune disorders. Finally, synergistic effect of a combination of prophylactic or therapeutic agents may avoid or reduce adverse or unwanted side effects associated single agent therapy.

As used herein, the terms "therapeutic agent" and "therapeutic agents" refer to CD3 binding molecules which can be used in the prevention, treatment, management or amelioration of one or more symptoms of an autoimmune or inflammatory disease. In certain embodiments, the term "therapeutic agent" refers to anti-human CD3 antibodies (e.g., OKT3 and variants or derivatives thereof).

As used herein, the term "therapeutically effective amount" refers to that amount of a therapeutic agent sufficient to result in amelioration of one or more symptoms of a disorder. With respect to diabetes, a therapeutically effective amount preferably refers to the amount of therapeutic agent that reduces a subject's average daily insulin requirements by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%.

As used herein, the terms "treat", "treatment" and "treating" refer to the amelioration of one or more symptoms associated with an autoimmune or inflammatory disorder that results from the administration of one or more CD3 binding molecules. In particular, such terms refer to the amelioration of one or more symptoms associated with an autoimmune disorders that results from the administration of one or more anti-human CD3 antibodies

4. DESCRIPTION OF THE FIGURES

FIGS. 1A and 1B. Sequences of humanized OKT3 variable regions. FIG. 1A and FIG. 1B show the alignments of the OKT3 light chain (FIG. 1A) (SEQ ID NO: 1) and the heavy chain (FIG. 1B) (SEQ ID NO:5) variable domain amino acid sequence (row 1), the variable domain sequence from the human antibodies chosen as light and heavy chain acceptor framework (row 2) (SEQ ID NOs:2 and 6, respectively), and the humanized OKT3 variable domain sequences (rows 3-5) (SEQ ID NO:3, SEQ ID NO:4, SEQ ID NO:7, SEQ ID NO:8 and SEQ ID NO:9). The CDR choices are singly underlined. Rows 3-5 show only differences from the human acceptor sequence, with the non-CDR differences shown double underlined. Dashes indicate gaps introduced in the sequences to maximize the alignment. Numbering is as in Kabat et al., *Sequences of Proteins of Immunological Interest*, 5$^{th}$ Ed. Public Health Service, NH1, MD (1991), which is incorporated by reference herein.

FIGS. 2A-2D. FIGS. 2A and 2B, nucleotide and amino acid sequences, respectively, of the light chain of humanized OKT3γ1 (SEQ ID NOs: 10 and 11, respectively). FIGS. 2C and 2D, nucleotide and amino acid sequences, respectively, of the heavy chain of humanized OKT3γ1 (ala-ala) (SEQ ID NOs: 12 and 13, respectively).

FIG. 3. Schematic representation of mammalian expression vector pMGX1303, containing coding regions for humanized OKT3 and capable of promoting expression of the humanized antibody in CHO cells.

5. DETAILED DESCRIPTION OF THE INVENTION

The present invention provides methods of treating, preventing, slowing the progression of and ameliorating the symptoms of autoimmune diseases or disorders using proteins, particularly, antibodies, directed against the CD3 complex associated with the human T cell receptor or TcR. In particular embodiments, the antibody binds to the epsilon subunit of the CD3 complex. The methods of the invention may be used with any anti-human CD3 antibody presented herein or known in the art, e.g. OKT3, ChAglyCD3 (TRX4™), HUM291 (visilizumab; Nuvion™), UCHT1, Leu4, 500A2, CLB-T3/3, BMA030 and YTH 12.5, and variations or derivatives thereof. In one embodiment of the invention the antibody is OKT3, preferably humanized versions of OKT3 or an antibody that competes for binding, for example, as determined by immunoprecipitation assay or ELISA, with OKT3. In another embodiment, the antibody is humanized OKT3, which has been modified at one or more amino acid residues to exhibit reduced T cell activation and/or FcR binding when compared to a non-modified humanized OKT3 antibody, such as having an alanine at, e.g., residue number 234 of the Fc domain, and an alanine at, e.g., residue number 235 of the Fc domain. Preferably, the anti-human CD3 antibodies are administered are administered at lower dosages or over shorter periods of time than prior dosing regimens. In particular, the invention contemplates dosing regimens in which less than 9,000 µg/m$^2$, preferably, less than 8,000 µg/m$^2$, less than 7,500 µg/m$^2$, less than 7,000 µg/m$^2$, or less than 6,000 µg/m$^2$ total anti-human CD3 antibody over the duration of the dosing, particularly of OKT3γ1 (ala-ala) administered intravenously, or the pharmacological equivalent amount of another anti-human CD3 antibody of this dose of OKT3γ1 (ala-ala) administered intravenously and/or any anti-human CD3 antibody administered by a route of administration other than intravenously, as well as chronic dosing methods and redosing or repeated dosing methods.

Anti-CD3 mAbs are potent immunosuppressive agents directed against an invariant protein complex associated with the human TcR (Van Wauwe, 1980, J. Immunol. 124:2708). The CD3 complexes are believed to be accessory structures that transduce the activation signals initiated upon binding of the TcR to its ligand. Binding of the anti-CD3 antibody OKT3 to the TcR mediates TcR blockade and inhibits alloantigen recognition and cell-mediated cytotoxicity (Landegren et al., 1982, J. Exp. Med. 155:1579; van Seventer et al., 1987, J. Immunol. 139:2545; Weiss et al., 1986, Ann. Rev. Immunol. 4:593). However, the administration of some immune-cell directed antibodies, including OKT3 and other anti-CD3 antibodies, may induce T cell activation, including the systematic release of several cytokines, including IL-2, IL-6, TNF-α and IFN-γ (Abramowicz, 1989, Transplantation, 47:606-608; Chatenoud, 1989, New Eng. J. Med. 320:1420-1421). This production of cytokines has been correlated with the adverse side-effects frequently observed after the first injection of mAbs (Van Wauwe, 1980, J. Immunol. 124:2708; Chatenoud, 1989, New Eng. J. Med. 320:1420-1421; Thistlethwaite, 1988, Am J Kidney Dis., 11:112-9), and may augment the production of anti-isotypic and anti-idiotypic antibodies occurring in some patents after one or two weeks of treatment. This immune response can neutralize the specific antibody, as well as other antibodies of the same class (isotype), and preclude subsequent treatments (Thistlethwaite, 1988, Am J Kidney Dis. 11:112-9).

Several pieces of evidence strongly suggest that these side-effects are a consequence of the cross-linking between T lymphocytes and Fc receptor (FcR)-bearing cells through the Fc portion of antibodies, including for example, OKT3, resulting in activation of both cell types (Debets, 1990, J. Immunol. 144:1304; Krutman, 1990, J. Immunol. 145:1337): 1) anti-CD3 mAbs did not stimulate T cell proliferation in vitro, unless the antibody was immobilized to plastic or bound to FcR+ antigen presenting cells included in the culture (van Lier, 1989, Immunol. 68:45); 2) the cross-linking of OKT3 through FcRs I and II enhanced proliferation in response to IL-2, in vitro (van Lier, 1987, J. Immunol. 139: 2873); 3) proliferation of murine T cells induced by 145-2C11, a hamster monoclonal antibody directed against the murine CD3 complex, could be blocked by the anti-FcR antibody, 2.4G2; 4) the injection into mice of F(ab')$_2$ fragments of 145-2C11 induced significant immunosuppression without triggering full T cell activation (Hirsch, 1990, Transplantation, 49:1117-23) and was less toxic in mice than the whole antibody (Alegre, 1990, Transplant Proc. 22:1920-1); and 5) the administration of an OKT3 IgA switch variant that displayed a reduced FcR-mediated T cell activation as compared with OKT3 IgG2a, resulted in fewer side effects in chimpanzees in vivo (Parleviet, 1990, Brief Communications 50:889-892).

Administration of certain anti-CD3 antibodies has also been associated with transient retrovirus activation, specifically activation of dormant Epstein-Barr Virus (EBV) infection. Anti-CD3 antibody treatment has also been found to be lytic to activated T cells and apoptotic to some T cell populations. The reasons for these effects are unclear, but they may be dose related and are probably the result of the modulation of the TcR complex resulting in suboptimal signaling.

Thus improvement of anti-CD3 mAb therapy can be obtained by molecularly modifying the antibody to reduce its affinity for FcRs. The mutated Ab obtained could lead to lower cellular activation and reduced toxicity in vivo, but retain the original immunosuppressive properties of the antibody.

5.1 Antibodies that Immunospecifically Bind to CD3 Polypeptides

It should be recognized that antibodies that immunospecifically bind to a CD3 polypeptide are known in the art. Examples of known antibodies that immunospecifically bind to a CD3 polypeptide include, but are not limited to OKT3, HuM291, ChAglyCD3, UCHT1, Leu4, 500A2, CLB-T3/3, BMA030, YTH 12.5 and rat CD3 antibody (See Herold et al., 2005, Diabetes 54:1763-1769; Carpenter et al., 2005, Biol. Blood Marrow Transplant 11:465-471; Keymeulen et al., 2005, N. Engl. J. Med. 352:26422644; Schwinzer et al., 1992, J. Immunol. 148:1322-1328; Tsoukas et al., 1985, J. Immunol. 135:1719-1723; U.S. Pat. No. 6,491,916; Brams et al., 1989, Immunol., 66:348-353; van Lier et al., 1989, Immunol. 68:45-50; Walker et al., 1987, Eur. J. Immunol. 17:1611-1618; Routledge et al., 1991, Eur. J. Immunol. 21:2717-2725, respectively).

The present invention provides methods of treating, preventing, slowing the progression of and ameliorating the symptoms of autoimmune disorders using antibodies that immunospecifically bind to a CD3 polypeptide expressed by an immune cell such as a T cell, wherein said antibodies modulate an activity or function of said T cell. In a specific embodiment, antibodies that immunospecifically bind to a CD3 polypeptide directly or indirectly modulate the activity of lymphocytes, preferably peripheral blood T cells. In particular, the present invention provides antibodies that immunospecifically bind to a CD3 polypeptide expressed by a T cell, and said antibodies modulate the activity of peripheral blood T cell.

In a specific embodiment, antibodies that immunospecifically bind to a CD3 polypeptide inhibit T cell activation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% and inhibit T cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% in an in vivo or in vitro assay described herein or well-known to one of skill in the art. In another embodiment, antibodies that immunospecifically bind to a CD3 polypeptide inhibit alloantigen recognition by T cells by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% in an in vivo or in vitro assay described herein or well-known to one of skill in the art. In another embodiment, antibodies that immunospecifically bind to a CD3 polypeptide inhibit T cell mediated cytotoxicity by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% in an in vivo or in vitro assay described herein or well-known to one of skill in the art.

In another embodiment, the methods of the invention employ antibodies that immunospecifically bind to a CD3 polypeptide and do not induce or have reduced (as compared to unmodified antibodies, e.g., the murine OKT3 monoclonal antibody) cytokine expression and/or release in an in vivo or in vitro assay described herein or well-known to one of skill in the art. In a specific embodiment, antibodies that immunospecifically bind to a CD3 polypeptide do not induce an increase in the concentration cytokines such as, e.g., IFN-γ, IL-2, IL-4, IL-6, IL-9, IL-12, and IL-15 in the serum of a subject administered such an antibody. In an alternative embodiment, antibodies that immunospecifically bind to a CD3 polypeptide induce cytokine expression and/or release in an in vitro or in vivo assay described herein or well-known to one of skill in the art but at levels less than those induced by unmodified anti-CD3 antibodies, such as, the murine OKT3 monoclonal antibody. Serum concentrations of a cytokine can be measured by any technique well-known to one of skill in the art such as, e.g., ELISA.

In another embodiment, antibodies that immunospecifically bind to a CD3 polypeptide induce T cell anergy in an in vivo or in vitro assay described herein or well-known to one of skill in the art. In an alternative embodiment, antibodies that immunospecifically bind to a CD3 polypeptide do not induce T cell anergy in an in vivo or in vitro assay described herein or well-known to one of skill in the art. In another embodiment, antibodies that immunospecifically bind to a CD3 polypeptide elicit a state of antigen-specific unresponsiveness for at least 30 minutes, at least 1 hour, at least 2 hours, at least 6 hours, at least 12 hours, at least 24 hours, at least 2 days, at least 5 days, at least 7 days, at least 10 days or more in an in vitro assay described herein or known to one of skill in the art.

In another embodiment, antibodies that immunospecifically bind to a CD3 polypeptide inhibit T cell activation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% and inhibit T cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, or at least 98% in an in vivo or in vitro assay described herein or well-known to one of skill in the art.

In yet another embodiment, antibodies that immunospecifically bind to a CD3 polypeptide achieve T cell coating or modulation by at least 50%, at least 55%, at least 60%, at least 65%, at least 70%, at least 75%, at least 80%, at least 85%, at least 90%, at least 95%, or at least 98% and inhibit T cell proliferation by at least 25%, at least 30%, at least 35%, at least 40%, at least 50%, at least 55%, at least 60%, at least 65%, at least 70%, at least 75%, at least 80%, at least 85%, at least 90%, at least 95%, at least 98%, at least 99%, and preferably by 100% in an in vivo or in vitro assay described herein or well-known to one of skill in the art.

In another embodiment, the Fc domain of an antibody that immunospecifically binds to a CD3 polypeptide does not detectably bind to one or more of the Fc receptors ("FcR") FcRI, FcRII, and/or FcRIII expressed by an immune cell such as a T cell, monocyte, and macrophage.

Antibodies that immunospecifically bind to a CD3 polypeptide include, but are not limited to, monoclonal antibodies, multispecific antibodies, human antibodies, humanized antibodies, chimeric antibodies, single-chain Fvs (scFv), single chain antibodies, Fab fragments, F(ab') fragments, F(ab')$_2$ fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies that immunospecifically bind to a CD3 polypeptide include immunoglobulin molecules and immunologically active portions of immunoglobulin molecules, i.e., molecules that contain an antigen binding site that immunospecifically binds to a CD3 polypeptide. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. In a specific embodiment, the antibodies that immunospecifically bind to a CD3 polypeptide and mediate the activity of T cells comprise an Fc domain or a fragment thereof (e.g., the CH2, CH3, and/or hinge regions of an Fc domain). In a preferred embodiment, the antibodies that immunospecifically bind to a CD3 polypeptide and mediate the activity of T cells comprise an Fc domain or fragment thereof that does not detectably bind to an FcR (e.g., one or more of an FcRI, FcRII or FcRIII) expressed by an immune cell or has reduced FcR binding as compared to an antibody with a wild type Fc domain.

The antibodies that immunospecifically bind to a CD3 polypeptide may be from any animal origin including birds and mammals (e.g., human, murine, donkey, sheep, rabbit, goat, guinea pig, camel, horse, or chicken). Preferably, the antibodies of the invention are human, humanized or chimeric monoclonal antibodies. Human antibodies that immunospecifically bind to a CD3 polypeptide include antibodies having the amino acid sequence of a human immunoglobulin and antibodies isolated from human immunoglobulin libraries or from mice that express antibodies from human genes.

The antibodies that immunospecifically bind to a CD3 polypeptide may be monospecific, bispecific, trispecific or of greater multispecificity. Multispecific antibodies may be specific for different epitopes of a CD3 polypeptide or may be specific for both a CD3 polypeptide as well as for a heterologous epitope, such as a heterologous polypeptide or solid support material. See, e.g., PCT publications WO 93/17715, WO 92/08802, WO 91/00360, and WO 92/05793; Tutt, et al., J. Immunol. 147:60-69 (1991); U.S. Pat. Nos. 4,474,893, 4,714,681, 4,925,648, 5,573,920, and 5,601,819; and Kostelny et al., J. Immunol. 148:1547-1553 (1992).

The present invention provides for antibodies that have a high binding affinity for a CD3 polypeptide. In a specific embodiment, an antibody that immunospecifically binds to a CD3 polypeptide has an association rate constant or $k_{on}$ rate (antibody (Ab)+antigen (Ag)$^{k_{on}}$→Ab-Ag) of at least $10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, or at least $10^8$ M$^{-1}$ s$^{-1}$. In a preferred embodiment, an antibody that immunospecifically binds to a CD3 polypeptide has a $k_{on}$ of at least $2\times10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, or at least $10^8$ M$^{-1}$ s$^{-1}$.

In another embodiment, an antibody that immunospecifically binds to a CD3 polypeptide has a $k_{off}$ rate (antibody (Ab)+antigen (Ag)$^{K_{off}}$→Ab-Ag) of less than $10^{-1}$ s$^{-1}$, less than $5\times10^{-1}$ s$^{-1}$, less than $10^{-2}$ s$^{-1}$, less than $5\times10^{-2}$ s$^{-1}$, less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$. In a preferred embodiment, an antibody that immunospecifically binds to a CD3 polypeptide has a $k_{on}$ of less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$.

In another embodiment, an antibody that immunospecifically binds to a CD3 polypeptide has an affinity constant or $K_a$ ($k_{on}/k_{off}$) of at least $10^2$ M$^{-1}$, at least $5 \times 10^2$ M$^{-1}$, at least $10^3$ M$^{-1}$, at least $5 \times 10^3$ M$^{-1}$, at least $10^4$ M$^{-1}$, at least $5 \times 10^4$ M$^{-1}$, at least $10^5$ M$^{-1}$, at least $5 \times 10^5$ M$^{-1}$, at least $10^6$ M$^{-1}$, at least $5 \times 10^6$ M$^{-1}$, at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$, at least $10^{14}$ M$^{-1}$, at least $5 \times 10^{14}$ M$^{-1}$, at least $10^{15}$ M$^{-1}$, or at least $5 \times 10^{15}$ M$^{-1}$. In yet another embodiment, an antibody that immunospecifically binds to a CD3 polypeptide has a dissociation constant or $K_d$ ($k_{off}/k_{on}$) of less than $10^{-2}$ M, less than $5 \times 10^{-2}$ M, less than $10^{-3}$ M, less than $5 \times 10^{-3}$ M, less than $10^{-4}$ M, less than $5 \times 10^{-4}$ M, less than $10^{-5}$ M, less than $5 \times 10^{-5}$ M, less than $10^{-6}$ M, less than $5 \times 10^{-6}$ M, less than $10^{-7}$ M, less than $5 \times 10^{-7}$ M, less than $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-1}$ M, less than $10^{-12}$ M, less than $5 \times 10^{-12}$ M, less than $10^{-13}$ M, less than $5 \times 10^{-13}$ M, less than $10^{-14}$ M, less than $5 \times 10^{-14}$ M, less than $10^{-15}$ M, or less than $5 \times 10^{-15}$ M.

In a specific embodiment, an antibody that immunospecifically binds to a CD3 polypeptide is humanized OKT3 or an antigen-binding fragment thereof e.g., (one or more complementarity determining regions (CDRs) of humanized OKT3). OKT3 has the amino acid sequence disclosed, e.g., in U.S. Pat. Nos. 4,658,019, 6,113,901 and 6,491,916 (each of which is incorporated herein by reference in its entirety), or the amino acid sequence of the monoclonal antibody produced by the cell line deposited with the American Type Culture Collection (ATCC®), 10801 University Boulevard, Manassas, Va. 20110-2209 on Jul. 28, 1993 as Accession Number CRL-8001 (which is incorporated herein by reference). Several humanized versions of OKT3 are also reported in U.S. Pat. No. 6,491,916. In an alternative embodiment, an antibody that immunospecifically binds to a CD3 polypeptide is not OKT3, a derivative of OKT3, e.g. humanized OKT3, an antigen-binding fragment of OKT3, or, more preferably, not a humanized or chimeric version thereof.

In a specific embodiment, the present invention also provides antibodies that immunospecifically bind a CD3 polypeptide, said antibodies comprising a variable heavy ("VH") domain having an amino acid sequence of the VH domain of a humanized OKT3 (for example, SEQ ID NO:5, SEQ ID NO:7, SEQ ID NO:8, or SEQ ID NO:9; FIG. 1B). In a preferred embodiment, the humanized OKT3 antibody comprises a heavy chain with the amino acid sequence of hOKT3γ1 (ala-ala) provided in FIG. 2D (SEQ ID NO: 13) or encoded by the nucleotide sequence of hOKT3γ1 (ala-ala) provided in FIG. 2C (SEQ ID NO: 12).

In a specific embodiment, the present invention also provides antibodies that immunospecifically bind to a CD3 polypeptide, said antibodies comprising a variable light ("VL") domain having an amino acid sequence of the VL domain for a humanized OKT3 (for example, SEQ ID NO: 1, SEQ ID NO:3, or SEQ ID NO:4; FIG. 1A). In a preferred embodiment, the humanized OKT3 antibody comprises a light chain with the amino acid sequence of hOKT3γ1 provided in FIG. 2B (SEQ ID NO: 11) or encoded by the nucleotide sequence of hOKT3γ1 provided in FIG. 2A (SEQ ID NO:10).

The present invention also provides antibodies that immunospecifically bind to a CD3 polypeptide, said antibodies comprising a VH domain disclosed herein, or a VH domain of an antibody disclosed herein, combined with a VL domain disclosed herein, or other VL domain. The present invention further provides antibodies that immunospecifically bind to a CD3 polypeptide, said antibodies comprising a VL domain disclosed herein, or a VL domain of an antibody disclosed herein, combined with a VH domain disclosed herein, or other VH domain.

In one embodiment, an isolated nucleic acid molecule encodes an antibody that immunospecifically binds to a CD3 polypeptide, said antibody comprising a VH domain having the amino acid sequence of the VH domain of a humanized OKT3 (for example, SEQ ID NO:5; SEQ ID NO:7, SEQ ID NO:8; SEQ ID NO:9, FIG. 1B).

In a preferred embodiment, an isolated nucleic acid molecule encodes an antibody that immunospecifically binds to a CD3 polypeptide, said antibody comprising a heavy chain having the amino acid sequence of the heavy chain of hOKT3γ-1 (ala-ala) disclosed in FIG. 2D (SEQ ID NO:13).

In one embodiment, an isolated nucleic acid molecule encodes an antibody that immunospecifically binds to a CD3 polypeptide, said antibody comprising a VL domain having the amino acid sequence of the VL domain of a humanized OKT3, for example, SEQ ID NO: 1; SEQ ID NO:3 or 4 (FIG. 1A).

In a preferred embodiment, an isolated nucleic acid molecule encodes an antibody that immunospecifically binds to a CD3 polypeptide, said antibody comprising a light chain having the amino acid sequence of the light chain of hOKT3γ-1 disclosed in FIG. 2B (SEQ ID NO:11).

In another embodiment, an isolated nucleic acid molecule encodes an antibody that immunospecifically binds to a CD3 polypeptide, said antibody comprising a VH domain having the amino acid sequence of the VH domain of a humanized OKT3, for example, SEQ ID NO:7, SEQ ID NO:8, or SEQ ID NO:9 (FIG. 1B) and a VL domain having the amino acid sequence of the VL domain of a humanized OKT3, for example, SEQ ID NO: 3 or SEQ ID NO:4 (FIG. 1A). In another embodiment, an isolated nucleic acid molecule encodes an antibody that immunospecifically binds to a CD3 polypeptide, said antibody comprising a heavy chain having the amino acid sequence of the heavy chain of a humanized OKT3, for example the amino acid sequence of hOKT3γ1 heavy chain disclosed in FIG. 2D (SEQ ID NO:13), and a light chain having the amino acid sequence of the light chain of a humanized OKT3, for example the amino acid sequence of hOKT3γ1 disclosed in FIG. 2B (SEQ ID NO: 11).

In one embodiment, antibodies that immunospecifically bind to a CD3 polypeptide comprise one or more VH CDRs disclosed in FIG. 1B. In another embodiment, antibodies that immunospecifically bind to a CD3 polypeptide comprise more than one of the VH CDRs disclosed in FIG. 1B.

In one embodiment, antibodies that immunospecifically bind to a CD3 polypeptide comprise a one or more of the VL CDRs disclosed in FIG. 1A. In another embodiment, antibodies that immunospecifically bind to a CD3 polypeptide comprise more than one of the VL CDRs disclosed in FIG. 1A.

In another embodiment, antibodies that immunospecifically bind to a CD3 polypeptide comprise one or more VH CDRs disclosed in FIG. 1B and one or more VL CDRs disclosed in FIG. 1A. In yet another embodiment, antibodies that immunospecifically bind to a CD3 polypeptide comprise more than one of the VH CDRs disclosed in FIG. 1B and more than one of the VL CDRs disclosed in FIG. 1A.

The present invention also provides antibodies that immunospecifically bind to a CD3 polypeptide, said antibodies comprising derivatives of the VH domains, VH CDRs, VL domains, or VL CDRs described herein, or available to one of ordinary skill in the art, that immunospecifically bind to a CD3 polypeptide. Standard techniques known to those of skill in the art can be used to introduce mutations in the nucleotide sequence encoding an antibody of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues (i.e., amino acid residues which are not critical for the antibody to immunospecifically bind to a CD3 polypeptide). A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody can be expressed and the activity of the antibody can be determined.

In a specific embodiment, the present invention provides for antibodies that immunospecifically bind to a CD3 polypeptide, said antibodies comprising the amino acid sequence of a humanized OKT3 with one or more amino acid residue substitutions in the variable light (VL) domain and/or variable heavy (VH) domain. The present invention also provides for antibodies that immunospecifically bind to a CD3 polypeptide, said antibodies comprising the amino acid sequence of the heavy and light chains variable domains of murine (SEQ ID NOs:5 and 1, respectively) with one or more amino acid residue substitutions in one or more VL CDRs and/or one or more VH CDRs. The antibody generated by introducing substitutions in the VH domain, VH CDRs, VL domain and/or VL CDRs of humanized OKT3 can be tested in vitro and in vivo, for example, for its ability to bind to a CD3 polypeptide, or for its ability to inhibit T cell activation, or for its ability to inhibit T cell proliferation, or for its ability to induce T cell lysis, or for its ability to prevent, treat or ameliorate one or more symptoms associated with an autoimmune disorder.

In a specific embodiment, an antibody that immunospecifically binds to a CD3 polypeptide comprises a nucleotide sequence that hybridizes to the nucleotide sequence encoding the monoclonal antibody produced by the cell line deposited with the ATCC® as Accession Number CRL-8001 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

In a specific embodiment, an antibody that immunospecifically binds to a CD3 polypeptide comprises a nucleotide sequence that hybridizes to the nucleotide sequence encoding the humanized OKT3 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. 1, Green Publishing Associates, Inc. and John Wiley & Sons, Inc., New York at pages 6.3.1-6.3.6 and 2.10.3).

In a specific embodiment, an antibody that immunospecifically binds to a CD3 polypeptide comprises an amino acid sequence of a VH domain or an amino acid sequence a VL domain encoded by a nucleotide sequence that hybridizes to the nucleotide sequence encoding the VH or VL domains of humanized OKT3 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. 1, Green Publishing Associates, Inc. and John Wiley & Sons, Inc., New York at pages 6.3.1-6.3.6 and 2.10.3).

In another embodiment, an antibody that immunospecifically binds to a CD3 polypeptide comprises an amino acid sequence of a VH CDR or an amino acid sequence of a VL CDR encoded by a nucleotide sequence that hybridizes to the nucleotide sequence encoding any one of VH CDRs or VL CDRs of the monoclonal antibody produced by the cell line deposited with the ATCC® as Accession Number CRL-8001 under stringent conditions e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art.

In another embodiment, an antibody that immunospecifically binds to a CD3 polypeptide comprises an amino acid sequence of a VH CDR and an amino acid sequence of a VL CDR encoded by nucleotide sequences that hybridizes to the nucleotide sequences encoding the monoclonal antibody produced by the cell line deposited with the ATCC® as Accession Number CRL-8001 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art.

In a specific embodiment, an antibody that immunospecifically binds to a CD3 polypeptide comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the monoclonal antibody produced by the cell line deposited with the ATCC® as Accession Number CRL-8001. In another embodiment, an antibody that immunospecifically binds to a CD3 polypeptide comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of humanized OKT3.

In another embodiment, an antibody that immunospecifically binds to a CD3 polypeptide comprises an amino acid sequence of a VH domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the VH domain of humanized OKT3.

In another embodiment, an antibody that immunospecifically binds to a CD3 polypeptide comprises an amino acid sequence of a VL domain that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the VL domain of humanized OKT3.

The present invention encompasses antibodies that compete with an antibody described herein for binding to a CD3 polypeptide. In a specific embodiment, the present invention encompasses antibodies that compete with anti-CD3 antibodies known in the art, derivatives thereof or antigen binding fragments thereof. For example, antibodies provided by the invention compete with OKT3 or a derivative thereof, e.g. humanized OKT3, or an antigen-binding fragment thereof for binding to the CD3 polypeptide. In another specific embodiment, the present invention encompasses antibodies that compete with ChAglyCD3 or a derivative thereof or an antigen-binding fragment thereof for binding to the CD3 polypeptide. In another specific embodiment, the present invention encompasses antibodies that compete with HuM291 or a derivative thereof or an antigen-binding fragment thereof for binding to the CD3 polypeptide. In another specific embodiment, the present invention encompasses antibodies that compete with UCHT1 or a derivative thereof or an antigen-binding fragment thereof for binding to the CD3 polypeptide. In another specific embodiment, the present invention encompasses antibodies that compete with Leu4 or a derivative thereof or an antigen-binding fragment thereof for binding to the CD3 polypeptide. In another specific embodiment, the present invention encompasses antibodies that compete with YTH 12.5 or a derivative thereof or an antigen-binding fragment thereof for binding to the CD3 polypeptide. In another specific embodiment, the present invention encompasses antibodies that compete with 500A2 or a derivative thereof or an antigen-binding fragment thereof for binding to the CD3 polypeptide. In another specific embodiment, the present invention encompasses antibodies that compete with CLB-T3/3 or a derivative thereof or an antigen-binding fragment thereof for binding to the CD3 polypeptide. In another specific embodiment, the present invention encompasses antibodies that compete with BMA030 or a derivative thereof or an antigen-binding fragment thereof for binding to the CD3 polypeptide.

The present invention also encompasses VH domains that compete with the VH domain of the antibodies disclosed herein, or with the VH domains of other anti-human CD3 antibodies known in the art, or derivatives or variants thereof for binding to a CD3 polypeptide. In a specific embodiment, the present invention encompasses VH domains that compete with the VH domain of OKT3 or a derivative thereof, e.g. humanized OKT3, for binding to a CD3 polypeptide. The present invention also encompasses VL domains that compete with the VL domain of the antibodies disclosed herein, or with the VL domains of other anti-human CD3 antibodies known in the art, or derivatives or variants thereof for binding to a CD3 polypeptide. In a specific embodiment, the present invention encompasses VL domains that compete with a VL domain of OKT3 or a derivative thereof, e.g. humanized OKT3, for binding to a CD3 polypeptide.

The antibodies that immunospecifically bind to a CD3 polypeptide include derivatives that are modified, i.e., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The present invention also provides antibodies that immunospecifically bind to a CD3 polypeptide, said antibodies comprising a framework region known to those of skill in the art. Preferably, the fragment region of an antibody of the invention is human.

The present invention also encompasses antibodies, and methods of use thereof, that immunospecifically bind to a CD3 polypeptide, said antibodies comprising the amino acid sequence of OKT3 or a derivative thereof, e.g. humanized OKT3, with mutations (e.g., one or more amino acid substitutions) in the framework regions. In certain embodiments, antibodies which immunospecifically bind to a CD3 polypeptide comprise the amino acid sequence of OKT3 or a derivative thereof, e.g. humanized OKT3, with one or more amino acid residue substitutions in the framework regions of the VH and/or VL domains.

The present invention also encompasses antibodies which immunospecifically bind to a CD3 polypeptide, said antibodies comprising the amino acid sequence of OKT3 or a derivative thereof, e.g. humanized OKT3, with mutations (e.g., one or more amino acid residue substitutions) in the variable and framework regions.

The present invention also provides for fusion proteins comprising an antibody that immunospecifically binds to a CD3 polypeptide and a heterologous polypeptide. Preferably, the heterologous polypeptide that the antibody is fused to is useful for targeting the antibody to T cells.

The antibodies of the invention include derivatives that are otherwise modified, i.e., by the covalent attachment of any type of molecule to the antibody such that covalent attachment does not prevent the antibody from binding antigen and/or generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

5.1.1 Polypeptides and Antibodies with Variant Fc Regions

The use of therapeutic monoclonal antibodies is limited by problems of "first dose" side effects. First dose side effects, range from mild flu-like symptoms to severe toxicity, can be mild to severe, and include symptoms, such as, high fever, chills/rigors, headache, tremor, nausea/vomiting, diarrhea, abdominal pain, malaise, muscle/joint aches and pains, and generalized weakness. The first dose side effects are believed to be caused by lymphokine production and cytokine release stimulated by the Fc region of an antibody binding to and activating an FcγR on an FcγR-containing cell.

The FcR recognizes immunoglobulins of one or more isotypes through a recognition domain on the α chain of the Fc receptor. Fc receptors are defined by their specificity for immunoglobulin subtypes. For example, Fc receptors for IgG are referred to as FcγR. Different accessory cells bear Fc receptors for antibodies of different isotype, and the isotype of the antibody determines which accessory cells will be engaged in a given response (reviewed by Ravetch J. V. et al. 1991, Annu. Rev. Immunol. 9: 457-92; Gerber J. S. et al. 2001 Microbes and Infection, 3: 131-139; Billadeau D. D. et al. 2002, The Journal of Clinical Investigation, 2(109): 161-1681; Ravetch J. V. et al., 2000, Science, 290: 84-89; Ravetch J. V. et al., 2001, Annu. Rev. Immunol. 19:275-90; Ravetch J. V. 1994, Cell 78: 553-60).

The invention thus encompasses CD3 binding molecules that reduce or eliminate at least one symptom associated with first dose side effects by reducing or eliminating binding of the Fc to one or more FcγR. Such CD3 binding proteins comprise a variant Fc region having one or more amino acid modifications, relative to a wild type Fc region. The modification decreases or eliminates binding of the Fc to one or more FcγRs, relative to a comparable wild type Fc region. The modification is typically an amino acid substitution. However, the modification can be an amino acid insertion and/or deletion. Typically, the modification occurs in the $CH_2$ and/or hinge region. Alternatively, binding of Fc to one or more FcγRs can be reduced or eliminated by altering or eliminating one or more glycosyl groups on the Fc domain. Fc glycosylation can be altered or eliminated by methods well know in the art. For example, Fc glycosylation can be altered by producing the Fc in a cell that is deficient in fucosylation (e.g., fuc6 null cells), or eliminated by deglycosylation enzymes or an amino acid modification that alters or eliminates a glycosylation site (e.g., the N-X-S/T glycosylation site at positions 297-299 in the CH2 domain). FcγR binding can be measured using standard methods known in the art and exemplified herein. The antibodies of the invention are thus particularly useful because they have reduced or no in vivo toxicity caused by lymphokine production or cytokine release. The affinities and binding properties of the molecules of the invention for an FcR are initially determined using in vitro assays (biochemical or immunological based assays) known in the art for determining Fc-FcR interactions, i.e., specific binding of an Fc region to an FcR including but not limited to ELISA assay, surface plasmon resonance assay, immunoprecipitation assays (See Section 5.4). Preferably, the binding properties of the molecules of the invention are also characterized by in vitro functional assays for determining one or more FcγR mediator effector cell functions (See Section 5.4). In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

5.1.1.1 Fcγ Receptors

Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI (CD64), FcγRII (CD32), and FcγRIII (CD16), which exhibit extensive homology but are encoded by distinct genes. Both activating and inhibitory signals are transduced through the FcγRs following ligation. These diametrically opposing functions result from structural differences among the different receptor isoforms. In general, the binding of a complimentary Fc domain to FcγRI, FcγRIIA and FcγRIIIA results in activation of downstream substrates (e.g., $PI_3K$) and leading to the release of proinflammatory mediators. In contrast, the binding of a complimentary Fc domain to FcγRIIB results in phosphorylation of FcγRIIB and association with the SH2 domain of the inositol polyphosphate 5'-phosphatase (SHIP). SHIP hydrolyzes phosphoinositol messengers released as a consequence of FcγRI mediated tyrosine kinase activation, consequently preventing the influx of intracellular $Ca^{++}$. Thus crosslinking of FcγRIIB dampens the activating response to FcγR ligation and inhibits cellular responsiveness.

Methods of measuring lymphokine production and cytokine release are known and routine in the art and encompassed herein. For example, cytokine release may be measured by measuring secretion of cytokines including but not limited to TNF-α, GM-CSF, IFN-γ. See, e.g., U.S. Pat. No. 6,491,916; Isaacs et al., 2001, Rheumatology, 40: 724-738; each of which is incorporated herein by reference in its entirety. Lymphokine production may be measured by measuring secretion of lymphokines including but not limited to Interleukin-2 (IL-2), Interleukin-4 (IL-4), Interleukin-6 (IL-6), Interleukin-12 (IL-12), Interleukin-16 (IL-16), PDGF, TGF-α, TGF-β, TNF-α, TNF-13, GCSF, GM-CSF, MCSF, IFN-α, IFN-β, IFN-γ, IGF-I, IGF-II. For example, see, Isaacs et al., 2001, Rheumatology, 40: 724-738; Soubrane et al., 1993, Blood, 81(1): 15-19; each of which is incorporated herein by reference in its entirety.

As used herein, the term "Fc region" is used to define a C-terminal region of an IgG heavy chain. Although the boundaries may vary slightly, the human IgG heavy chain Fc region is defined to stretch from Cys226 to the carboxy terminus. The Fc region of an IgG comprises two constant domains, CH2 and CH3. The CH2 domain of a human IgG Fc region usually extends from amino acids 231 to amino acid 341. The CH3 domain of a human IgG Fc region usually extends from amino acids 342 to 447. The CH2 domain of a human IgG Fc region (also referred to as "Cγ2" domain) usually extends from amino acid 231-340. The CH2 domain is unique in that it is not closely paired with another domain. Rather, two N-linked branched carbohydrate chains are interposed between the two CH2 domains of an intact native IgG.

In preferred embodiments, the invention encompasses molecules comprising a variant Fc region, wherein said variant Fc region comprises at least one amino acid modification relative to a wild-type Fc region, which variant Fc region does not bind any FcγR, as determined by standard assays known in the art and disclosed herein, relative to a comparable molecule comprising the wild type Fc region. In a specific embodiment, the one or more amino acid modifications which abolish binding to all FcγRs comprise Fc regions which have a phenylalanine at position 233; or an arginine at position 238; or an alanine at position 265; or a glutamic acid at position 265; or an alanine at position 270; or an asparagine at position 270; or an alanine at position 297; or a glutamine at position 297; or a phenylalanine at position 298; or an asparagine at position 298; or a any amino acid at position 299 other than serine or threonine; or an alanine at position 265 and at position 297; or an alanine at position 265 and a glutamine at position 297; or a glutamic acid at position 265 and an alanine at position 297; or a glutamic acid at position 265 and a glutamine at position 297; or an alanine at position 234 and an alanine at position 235. In another embodiment, the one or more amino acid modifications which abolish binding to all FcγRs comprise combinations of the modifications listed herein or combinations of the modifications listed herein with any that may confer null binding to FcγRIIIA, FcγRIIIB, and FcγRIIA as determined by the methods disclosed herein or known to one skilled in the art.

The invention encompasses methods for reducing or eliminating at least one symptom associated with first dose side effect in a patient comprising administering an effective amount of one or more antibodies of the invention. The methods of the invention reduce at least one symptom associated with cytokine release syndrome including but not limited to high fever, chills/rigors, headache, tremor, nausea/vomiting, diarrhea, abdominal pain, malaise, muscle/joint aches and pains, and generalized weakness.

The present invention provides for antibodies that immunospecifically bind to a CD3 polypeptide which have a extended half-life in vivo. In particular, the present invention provides antibodies that immunospecifically bind to a CD3 polypeptide which have a half-life in an animal, preferably a mammal and most preferably a human, of greater than 3 days, greater than 7 days, greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of antibodies (e.g., monoclonal antibodies, single chain antibodies and Fab fragments) in vivo, for example, inert polymer molecules such as high molecular weight polyethyleneglycol (PEG) can be attached to the antibodies with or without a multifunctional linker either through site-specific conjugation of the PEG to the N-terminus or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein.

Antibodies having an increased half-life in vivo can also be generated introducing one or more amino acid modifications (i.e., substitutions, insertions or deletions) into an IgG constant domain, or FcRn binding fragment thereof (preferably a Fc or hinge-Fc domain fragment). See, e.g., International Publication No. WO 98/23289; International Publication No. WO 97/34631; and U.S. Pat. No. 6,277,375, each of which is incorporated herein by reference in its entirety.

5.1.2 Antibody Conjugates

The present invention encompasses antibodies or antigen-binding fragments thereof that immunospecifically bind to a CD3 polypeptide recombinantly fused or chemically conjugated (including both covalently and non-covalently conjugations) to a heterologous polypeptide (or a fragment thereof, preferably at least 5, at least 10, at least 20, at least 30, at least 40, at least 50, at least 60, at least 70, at least 80, at least 90 or at least 100 contiguous amino acids of the polypeptide) to generate fusion proteins. The fusion does not necessarily need to be direct, but may occur through linker sequences. For example, antibodies may be used to target heterologous polypeptides to particular cell types (e.g., T cells), either in vitro or in vivo, by fusing or conjugating the antibodies to antibodies specific for particular cell surface receptors such as, e.g., CD4 and CD8.

The present invention also encompasses antibodies or antigen-binding fragments thereof that immunospecifically bind to a CD3 polypeptide fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

The present invention further encompasses antibodies or antigen-binding fragments thereof that immunospecifically bind to a CD3 polypeptide conjugated to an agent which has a potential therapeutic benefit. An antibody or an antigen-binding fragment thereof that immunospecifically binds to a CD3 polypeptide may be conjugated to a therapeutic moiety such as a cytotoxin, e.g., a cytostatic or cytocidal agent, an agent which has a potential therapeutic benefit, or a radioactive metal ion, e.g., alpha-emitters. A cytotoxin or cytotoxic agent includes any agent that is detrimental to cells. Examples of a cytotoxin or cytotoxic agent include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Agents which have a potential therapeutic benefit include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, an antibody or an antigen-binding fragment thereof that immunospecifically binds to a CD3 polypeptide may be conjugated to a therapeutic agent or drug moiety that modifies a given biological response. Agents which have a potential therapeutic benefit or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon-α ("IFN-α"), interferon-β ("IFN-β"), nerve growth factor ("NGF"), platelet derived growth factor ("PDGF"), tissue plasminogen activator ("TPA"), an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), IL-2, IL-6, IL-10, granulocyte macrophage colony stimulating factor ("GM-CSF"), and granulocyte colony stimulating factor ("G-CSF")), or a growth factor (e.g., growth hormone ("GH")).

Techniques for conjugating such therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985); and Thorpe et al., 1982, Immunol. Rev. 62:119-58.

An antibody or an antigen-binding fragment thereof that immunospecifically binds to a CD3 polypeptide can be conjugated to a second antibody to form an antibody heteroconjugate as described by Segal in U.S. Pat. No. 4,676,980, which is incorporated herein by reference in its entirety.

Antibodies or antigen-binding fragments thereof that immunospecifically bind to a CD3 polypeptide may be attached to solid supports, which are particularly useful for the purification of CD3+ immune cells such as T cells. Such solid supports include, but are not limited to, glass, cellulose, polyacrylamide, nylon, polystyrene, polyvinyl chloride or polypropylene.

5.2 Prophylactic and Therapeutic Methods

The present invention is directed to therapies which involve administering CD3 binding molecules, particularly anti-human CD3 antibodies, to a subject, preferably a human subject, for preventing, treating, delaying the onset of, slowing the progression of or ameliorating one or more symptoms of an autoimmune disorder. In particular, the present invention is directed to therapies which involve administering CD3 binding molecules, particularly anti-human CD3 antibodies, more particularly human or humanized forms of anti-human CD3 antibodies, such as OKT3γ1 (ala-ala), ChAglyCD3, and visilizumab that have Fc domains that do not bind or have significantly reduced binding to Fc receptors, to a subject, preferably a human subject, for preventing, treating, delaying the onset of, slowing the progression of or ameliorating one or more symptoms of an autoimmune disorder, e.g., type 1 diabetes. The methods disclosed herein are generally improved methods of administration that permit administration of lower dosages and/or over shorter periods of time that still achieve clinical efficacy and avoid toxicity. In particular, the invention contemplates dosing regimens in which less than 9,000 μg/m$^2$, preferably, less than 8,000 μg/m$^2$, less than 7,500 μg/m$^2$, less than 7,000 μg/m$^2$, or less than 6,000 μg/m$^2$ total anti-human CD3 antibody over the duration of the dosing, particularly of OKT3γ1 (ala-ala), or the pharmacological equivalent amount of another anti-human CD3 antibody, such as ChAglyCD3 (TRX4™) or HUM291 (visilizumab; NUVION™), or OKT3γ1 (ala-ala) administered intravenously. The invention further contemplates methods in which the patient is chronically administered low doses of the anti-human CD3 antibody and in which the patient is administered one or more additional rounds of the anti-human CD3 antibody treatment regimen approximately 6 months, 9 months, 12 months, 18 months, 2 years, 3 years or 5 years after the initial treatment, depending or not on certain clinical parameters, or is administered another round of treatment with anti-human CD3 antibody every approximately 6 months, 9 months, 12 months, 18 months, 2 years, 3 years or 5 years, depending or not on certain clinical parameters.

Examples of autoimmune disorders that may be treated by administering the molecules of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), irritable bowel disease (IBD), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatics, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, SjSgren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Some autoimmune disorders are also associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, pulmonary fibrosis, undifferentiated spondyloarthropathy, undifferentiated arthropathy, arthritis, inflammatory osteolysis, and chronic inflammation resulting from chronic viral or bacteria infections. Examples of the types of psoriasis which can be treated in accordance with the compositions and methods of the invention include, but are not limited to, plaque psoriasis, pustular psoriasis, erythrodermic psoriasis, guttate psoriasis and inverse psoriasis.

5.2.1 Diabetes

Immune-mediated diabetes mellitus or type 1 diabetes is caused by an autoimmune response in which the insulin producing β-cells of the pancreas are gradually destroyed. Destruction of the β-cells is believed largely mediated by CTLs (CD8+ T cells). The early stage of the disease, termed insulitis, is characterized by infiltration of leukocytes into the pancreas and is associated with both pancreatic inflammation and the release of anti-β-cell cytotoxic antibodies. Early stages of the disease are often overlooked or misdiagnosed as clinical symptoms of diabetes typically manifest only after about 80% of the β-cells have been destroyed. Even with immunosuppressive therapy, α-cell populations do not recover to a significant extent; therefore, once clinical symptoms occur, the type-1 diabetic is normally insulin dependent for life. Insulin is currently the only standard therapy for treating symptoms of type 1 diabetes. Although immunosuppressive drugs such as methotrexate and cyclosporin showed early clinical promise in the treatment of type 1 diabetes, e.g., maintenance of α-cell function, as with all general immunosuppressants, their prolonged use was associated with a number of severe side effects. Use of the invention in the context of diabetes therefore encompasses methods to sustain/protect the levels and functionality of β-cells which exist at the time of treatment.

In a specific embodiment, anti-human CD3 antibody therapy is not used for the treatment of acute diabetes but rather to prevent progression of the disease in recently diagnosed individuals, including children diagnosed with juvenile diabetes (see Herold et al., 2005, Diabetes 54:1763-1769). In a specific embodiment, anti-human CD3 therapy is used only in patients that have residual β-cell function as determined by methods described herein or known to one of ordinary skill in the art. In another embodiment, anti-human CD3 antibody therapy is used to maintain transplanted β-cell function in pancreatic transplant recipients.

In alternate embodiments, the invention encompasses administration of anti-human CD3 antibodies to individuals predisposed to develop type 1 diabetes, but do not meet the diagnosis criteria as established by the American Diabetes Association or the Immunology of Diabetes Society to prevent or delay the onset of type 1 diabetes and/or to prevent or delay the need for administration of insulin to such patients. In certain embodiments, high-risk factors for identification of predisposed subjects in accordance with this embodiment are having first or second degree relatives with diagnosed type-1 diabetes, an impaired fasting glucose level (i.e., at least one determination of a glucose level of 100-125 mg/dl after fasting (8 hour with no food)), an impaired glucose tolerance in response to a 75 g OGTT (i.e., at least one determination of a 2-hr glucose level of 140-199 mg/dl in response to a 75 g OGTT), an HLA type of DR7 in a Caucasian, an HLA type of DR4 in a person of African descent, an HLA type of DR9 in a person of Japanese descent, exposure to childhood viruses (e.g., coxsackie B virus, enteroviruses, adenoviruses, rubella, cytomegalovirus, Epstein-Barr virus), a positive diagnosis according to art accepted criteria of at least one other autoimmune disorder (e.g., thyroid disease, celiac disease), and/or the detection of autoantibodies, particularly ICAs, in the serum or other tissues. In certain embodiments, the subject identified as predisposed to developing type 1 diabetes according the methods of the invention has at least one of the risk factors described herein and/or as known in the art. The invention also encompasses identification of subjects predisposed to development of type 1 diabetes, wherein said subject presents a combination of two or more, three or more, four or more, or more than five of the risk factors disclosed herein or known in the art.

Serum autoantibodies associated with type 1 diabetes or with a predisposition for the development of type 1 diabetes are islet-cell autoantibodies (e.g., anti-ICA512 autoantibodies), glutamic acid decarbamylase autoantibodies (e.g., anti-GAD65 autoantibodies), and/or anti-insulin autoantibodies. Accordingly, in a specific example in accordance with this embodiment, the invention encompasses the treatment of an individual with detectable autoantibodies associated with a predisposition to the development of type 1 diabetes or associated with early stage type 1 diabetes (e.g., anti-IA2, anti-ICA512, anti-GAD or anti-insulin autoantibodies), wherein said individual has not been diagnosed with type 1 diabetes and/or is a first or second degree relative of a type-1 diabetic. In certain embodiments, the presence of the autoantibodies is detected by ELISA, radioassay (see, e.g., Yu et al., 1996, J. Clin. Endocrinol. Metab. 81:4264-4267), or by any other method for immunospecific detection of antibodies described herein or as known to one of ordinary skill in the art.

β-cell function prior to, during, and after therapy may be assessed by methods described herein or by any method known to one of ordinary skill in the art. For example, the Diabetes Control and Complications Trial (DCCT) research group has established the monitoring of percentage glycosylated hemoglobin (HA1 and HA1c) as the standard for evaluation of blood glucose control (DCCT, 1993, N. Engl. J. Med. 329:977-986). Alternatively, characterization of daily insulin needs, C-peptide levels/response, hypoglycemic episodes, and/or FPIR may be used as markers of β-cell function or to establish a therapeutic index (See Keymeulen et al., 2005, N. Engl. J. Med. 352:2598-2608; Herold et al., 2005, Diabetes 54:1763-1769; U.S. Pat. Appl. Pub. No. 2004/0038867 A1; and Greenbaum et al., 2001, Diabetes 50:470-476, respectively). For example, FPIR is calculated as the sum of insulin values at 1 and 3 minutes post IGTT, which are performed according to Islet Cell Antibody Register User's Study protocols (see, e.g., Bingley et al., 1996, Diabetes 45:1720-1728 and McCulloch et al., 1993, Diabetes Care 16:911-915).

5.2.2 Multiple Sclerosis

Diagnosis of MS typically requires multiple neurological evaluations in order to exclude other more common causes of the symptoms presented. As of 2001, the International Panel on MS Diagnosis has recommended revised diagnostic criteria for a determination of multiple sclerosis that include advances in MRI technology (e.g., improved imaging of lesions) and other paraclinical diagnostic methods. The updated criteria have been called the McDonald criteria after the lead author of the report, and represent improvements over previous diagnostic criteria, i.e. the Poser and Schumacher criteria (see, McDonald et al., 2001, Ann. Neurol. 50:121-127).

Studies of the natural history of MS suggest that there are different patterns of disease activity although four main varieties are recognized: Relapsing/Remitting MS (RRMS), Secondary Progressive MS (SPMS), Progressive Relapsing MS (PRMS), and Primary Progressive MS (PPMS) (see, e.g., Lublin et al., 1996, Neurology 46:907-911. The distinction between the varieties depend on the frequency and severity of the attacks, and the progression thereof. RRMS is characterized by full or partial recovery between attacks, with a general stability of baseline condition are defined as having relapsing-remitting MS. In some instances, RRMS includes "benign" MS, characterized by rare attacks and minimum disability ten years post MS diagnosis. Patients experiencing RRMS constitute approximately 80-90% of MS sufferers. Of these, approximately 50% will have difficulty walking 15 years after onset and 80% will ultimately (after 25 years) experience gradual progression of disability with or without attacks. Patients who first experience exacerbations and later experience gradual progression of disability have SPMS. Approximately 10-15% of MS patients do not experience an initial attack. Those patients who gradually worsen after the appearance of the first symptom have PPMS. A few patients with primary progressive MS will later experience an exacerbation; these patients have PRMS.

Clinical tests for diagnosing and/or monitoring MS progression include, for example, magnetic resonance imaging (MRI) scan to detect lesions or monitor lesion size, lumbar puncture to detect evidence of inflammation, an evoked potential test (eye, ear, or skin) to measure the speed at which messages from the brain pass along nerves in response to stimuli (visual, auditory, or pain, respectively), use of the Kurtzke expanded disability status scale (EDSS) to rate the severity of the symptoms, urinalysis to measure the level of myelin basic protein-like material present in a urine sample, measuring atrophy in the brain or spinal cord, and detecting black holes (areas in the brain that emit very low signals on an MRI scan). Accordingly, the invention encompasses the use of an anti-CD3 antibody of the invention for the treatment of multiple sclerosis in patients exhibiting one or more indications of having the disease, or wherein a diagnosis according to McDonald criteria has been established.

While not being bound by a particular mechanism of action, administration of anti-CD3 antibody, and in particular, hOKT3 ala-ala, leads to treatment of autoimmune disorders, including, for example, type-1 diabetes and MS, by induction of immunologic tolerance. Multiple studies have identified several possible mechanisms by which hOKT3-yl ala-ala may induce tolerance including induction of T cell anergy, a process whereby T cells become quiescent and fail to react to self antigens; activation of $T_{Reg}$ populations, recently identified sub-populations of T cells which are expanded by hOKT3y1-ala-ala in vivo and exert dominant inhibitory effects on autoreactive T cells; and enhanced production of immunoregulatory Th2-type cytokines such as IL-10 and TGF3, which contribute to $T_{reg}$-mediated suppression in vivo (see, e.g., Kohm et al., 2005, Int. Rev. Immunol. 24:361-392, Filippi et al., 2005, Int. Rev. Immunol. 24:341-360, and Chen et al., 2004, Cell. Mol. Immunol. 1:328-335).

5.2.3 Psoriasis

Psoriasis is a chronic, inflammatory, hyperproliferative skin disease that affects approximately 1-2% of the general population with men and women affected in equal numbers. (Nevitt, G. J. et al., 1996, British J. of Dermatology 135:533-537). Approximately 150,000 new cases of psoriasis and approximately 400 deaths from psoriasis are reported each year (Stem, R. S., 1995, Dermatol. Clin. 13:717-722). The most common type of psoriasis is chronic plaque syndrome. The condition is chronic for many sufferers and consists of periods of remission and relapse during the course of the disease (Ashcroft, D. M., et al., 2000, J. of Clin. Pharm. And Therap. 25: 1-10).

Psoriasis is characterized by indurated, erythematous scaling plaques most commonly located on the scalp or the extensor aspects of the elbows and knees, but may occur at any skin site. Present treatment options currently available for psoriasis include topical agents, phototherapy and systemic agents. Topical treatments are first-line therapy for patients with mild to moderate plaque psoriasis. Systemic treatment is generally prescribed for severe cases of psoriasis where topical therapy is either impractical or ineffective. Phototherapy can be administered either alone or in combination with either topical or systemic agents. Unfortunately, each of these treatment options is associated with severe side effects. Most of the topical agents available for the treatment of psoriasis are associated with skin irritation, toxicity and possible carcinogenicity (Ashcroft, D. M., et al., 2000, J. of Clin. Pharm, and Therap. 25:1-10). Phototherapy, either broadband (UVB) or long wave (UVA), is associated with short term risks such as vesiculation, nausea, erythema, headache and skin pain as well as long-term risks of actinic keratoses, premature ageing of the skin, irregular pigmentation and squamous cell carcinoma which is reported in a quarter of patients (Stern, R. S., 1994, Cancer 73:2759-2764). Systemic agents are also associated with adverse side effects, and most are unavailable to pregnant patients. In particular, methotrexate, which is considered to be the 'gold standard' for treatment of severe psoriasis, carries a risk of hepatotoxicity with long-term use. In addition, it is recommended that patients have a liner biopsy performed at or near the start of each treatment and after each cumulative dose of 1.0-1.5 mg MTX (Roenigk, H. H. et al., 1988, J. of the Am. Acad. Of Dermatology).

When patients are provided with information regarding the possible adverse effects of the currently available therapies for psoriasis, many often choose to live with the condition rather than undergo treatment (Greaves M. W., 1995, New England J. of Medicine 332:581-588). Thus, there remains a need for better methods of treating psoriasis than currently available therapies.

Use of the invention in the context of psoriasis therefore encompasses methods to treat the acute phases of the disease as well as to prevent recurrence of symptoms of psoriasis. The response to anti-CD3 therapy in the context of psoriasis may be assessed by methods described herein or by any method known to one of ordinary skill in the art. Common methods used to monitor the symptoms of psoriasis include, but are not limited to, the Psoriasis Area and Severity Index (PAST), Physician Global Assessment (PGA) and NPF Psoriasis Score (NPF-PS) (See Ashcroft et al., 1999, Br. J. Dermatol. 141:185-191; van der Kerkhof et al., 1997, Br. J. Dermatol. 137:661-662 and Krueger et al., 1999, National Psoriasis Foundation Psoriasis Forum 5:1-5, respectively).

5.2.4 Rheumatoid Arthritis

Rheumatoid arthritis (RA) is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing. Besides rheumatoid arthritis, other types of arthritis associated with autoimmune inflammation include the following: psoriatic arthritis, Reiter's syndrome and ankylosing spondylitis arthritis. Rheumatoid arthritis occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. However, only about 50% of the patients treated with a combination of methotrexate and anti-TNF-a agents such as recombinant soluble receptors for TNF-a show clinically significant improvement. Many patients remain refractory despite treatment. Difficult treatment issues still remain for patients with rheumatoid arthritis. Many current treatments have a high incidence of side effects or cannot completely prevent disease progression.

Use of the invention in the context of RA therefore encompasses methods to treat the acute phases of the disease as well as to prevent recurrence of symptoms of RA. The response to the therapeutic methods of the invention in the context of RA may be assessed by methods described herein or by any method known to one of ordinary skill in the art. For example, many, but not all, people with rheumatoid arthritis have rheumatoid-factor antibody in their blood; however, the presence of rheumatoid factor is not in itself definitive for a positive diagnosis of RA as other conditions are know which cause the rheumatoid factor to be produced. Therefore, the diagnosis and assessment of rheumatoid arthritis is most commonly based on a combination of factors, including, but not limited to: the specific location and symmetry of painful joints, the presence of joint stiffness in the morning, the presence of bumps and nodules under the skin (rheumatoid nodules), results of X-ray tests that suggest rheumatoid arthritis. The invention encompasses any method of assessing the severity of the condition accepted in the art. Common assessment methods are based on the subjective responses of the subject to pain questionnaires (e.g., the Health Assessment Questionnaire (HAQ) with Disability, Pain Severity, and Health State Subscales); however, such subjective assessments are often confounded by the psychological functioning of the subject. Accordingly, objective scales have been developed that allow quantitative assessment of rheumatoid arthritis severity by the treating physician, e.g., the Rheumatoid Arthritis Severity Scale ("RASS;" see, e.g., Bardwell et al., 2002, Rheumatology 41:38-45, hereby incorporated by reference herein in its entirety.) The RASS is a brief, physician-completed scale that takes into account three of the more commonly mentioned severity dimensions: disease activity, functional impairment and physical damage.

5.2.5 Tissue Transplantation

Tissue transplantation between genetically nonidentical individuals results in immunological rejection of the tissue through T cell-dependent mechanisms. To prevent allograft rejection, immunosuppression is achieved with agents that generally interfere with T cell function by modulating TcR signal transduction (see, e.g., Borel, J. F., 1989, Pharmacol. Rev. 42:260-372; Morns, P. J., 1991, Curr. Opin. Immunol. 3:748-751; Sigal et al., 1992, Ann. Rev. Immunol. 10:519-560; and L'Azou et al., 1999, Arch. Toxicol. 73:337-345). Further, since the effect of the immunosuppressive agents is short-lasting, transplant recipients normally require life-long treatment of immunosuppressive agents to prevent transplant rejection. Transplant recipients receiving long-term immunosuppressive treatment have a high risk of developing infections and tumors. For example, patients receiving immunotherapy are at higher risk of developing lymphomas, skin tumors and brain tumors (see, e.g., Fellstrom et al., 1993, Immunol. Rev. 134:83-98). As an alternative to the general immunosuppressive agents currently used for the prevention of allograft rejection, monoclonal antibodies, including OKT3, have been successfully used to specifically block receptors involved in T cell stimulation activation.

Use of the invention in the context of tissue transplantation therefore encompasses methods to treat the acute phases of the rejection as well as to prevent recurrence of symptoms of rejection. The response to the therapeutic methods of the invention in the context of tissue may be assessed by methods described herein or by any method known to one of ordinary skill in the art; however, no general methods, other than detecting an increasing frequency of CTL that recognize donor antigens (described infra), presently exist to monitor whether a transplant is being rejected by a recipient. Although the function of some transplants may be directly monitored (i.e. kidney or liver), often the first overt sign of rejection is a complete physiologic failure of the tissue, at which point the tissue is normally beyond rescue.

5.2.6 Diagnosis, Prediction and Assessment of Autoimmune Disorders

Patients with autoimmune disorders generally have an increasing frequency of CTL that recognize autoantigens. In the context of tissue transplantation, the patients will exhibit an increasing frequency of CTL that recognize donor-specific antigens. Such autoreactive or donor-reactive CTL may be detected in peripheral blood or target tissues. For example, in the diabetic patient, autoreactive CTL may be detected in pancreatic islet cell tissues; in the psoriatic patient, autoreactive CTL may be detected in epidermal or dermal tissues; in the arthritic patient, autoreactive CTL may be detected in synovial cell tissues and in the organ transplant recipient, donor-reactive CTL may be detected in the transplant graft. Since the generation of autoreactive or donor-reactive CTL is thought to precede the development of auto/donor antibodies and other indicia of the clinical symptoms of immune disorders, detection of specific CTL may in some cases enable more sensitive and specific diagnosis of the disorder.

The assays can also be used to quantify both the absolute number and the proportion of autoreactive CTL present in a sample, such as a peripheral blood sample, in both pre-clinical subjects and patients that have received therapy. In some embodiments, both the severity and course of the autoimmune or allograft disorder may be predicted and followed using such assays. For example, the human MHC class I molecule HLA-A 0201 can be used in combination with the a diabetic autoantigen, for example IA-2, to detect autoreactive CTL present in a peripheral blood sample of a pre-diabetic subject or diabetic patient currently undergoing therapy using the methods of the invention.

The compounds of the invention can also be used in vivo in combination with, for example, imaging techniques or other in vivo detection methods for detecting CTLs labeled by binding with compounds or formulations of the invention.

Antigen-specific CTLs can be detected using a wide variety of assays, including immunospot (e.g., ELISPOT) assays, MHC class I tetramer assays, or other assays, as described herein or as known to a person skilled in the art.

The time period over which any biomarker of disorder progression or therapeutic effectiveness may be evaluated may be the time period of a single dose or an extended treatment time period, e.g. hours, days, weeks or months.

5.2.7 Therapeutic and Prophylactic Methods

The compositions and methods of the invention are particularly useful for the prevention, treatment or amelioration of T cell mediated diseases such as autoimmune disorders characterized by increased T cell infiltration of lymphocytes into affected tissues, or autoimmune disorders characterized by increased T cell activation and/or abnormal antigen presentation and/or recognition. The compositions and methods are also useful for the prevention, treatment or amelioration of inflammatory disorders characterized by increased T cell activation and/or abnormal antigen presentation. In specific embodiments, the invention provides methods of treating, preventing, managing or ameliorating the symptoms of an autoimmune disease, particularly, Type I Diabetes, multiple sclerosis, ulcerative colitis, psoriasis, rheumatoid arthritis, lupus (particularly, cutaneous), psoriatic arthritis, inflammatory bowel disease (IBD), effects from organ transplantation, and graft vs. host disease (GVHD). Preferably, the treatment regimens described herein are administered to patients in early stages of the autoimmune disease, exhibiting mild tissue damage resulting from the immune reaction and requiring minimal medical intervention, e.g., low doses of standard therapy, to manage the disease. The treatment regimens described herein maintain high level functioning and prevent, slow or reduce additional tissue damage. Thus, the methods of the invention may reduce the need for additional therapy to treat, manage or ameliorate the disease or disorder, and/or symptoms thereof.

In a certain embodiments, pharmaceutical compositions comprising one or more CD3 binding molecules (e.g., one or more anti-human CD3 antibodies) are administered one or more times, preferably in a dosing regimen administered in multiple doses over a period of 2 to 20 days, to treat, manage or ameliorate the symptoms of an autoimmune diabetes disorder, to prevent or slow the decrease in β-cell function associated with autoimmune diabetes, or to delay or prevent the onset of an autoimmune diabetes disorder. in a subject with a predisposition for development of Type-1 diabetes as described herein. In yet another embodiment, one or more pharmaceutical compositions comprising one or more CD3 binding molecules (e.g., one or more anti-CD3 antibodies) are administered one or ore times to prevent decrease in β-cell function associated with diabetes in a subject that has had an allograft comprising pancreatic islet cell tissue. In accordance with these embodiments, changes in a subject's β-cell function may be assessed by characterization of daily insulin requirements, HA1c levels, C-peptide function/levels, frequency of hypoglycemic episodes or FPIR as known in the art.

In certain embodiments, the course of treatment with an anti-CD3 antibody according to the methods of the invention is repeated at 2 month, 4 month, 6 month, 8 month, 9 month, 10 month, 12 month, 15 month, 18 month, 24 month, 30 month, or 36 month intervals. In specific embodiments efficacy of the treatment with an anti-CD3 antibody of the invention is determined as described herein or as is known in the art at 2 months, 4 months, 6 months, 9 months, 12 months, 15 months, 18 months, 24 months, 30 months, or 36 months subsequent to the previous treatment.

In another embodiment, a subject is administered one or more unit doses of approximately 0.5-50 μg/kg, approximately 0.5-40 μg/kg, approximately 0.5-30 μg/kg, approximately 0.5-20 μg/kg, approximately 0.5-15 μg/kg, approximately 0.5-10 μg/kg, approximately 0.5-5 μg/kg, approximately 1-5 μg/kg, approximately 1-10 μg/kg, approximately 20-40 μg/kg, approximately 20-30 μg/kg, approximately 22-28 μg/kg or approximately 25-26 μg/kg of one or more anti-CD3 antibody to prevent, treat or ameliorate one or more symptoms of an autoimmune disorder, particularly diabetes. In another embodiment, a subject is administered one or more unit doses of 200 μg/kg, 178 μg/kg, 180 μg/kg, 128 μg/kg, 100 μg/kg, 95 μg/kg, 90 μg/kg, 85 μg/kg, 80 μg/kg, 75 μg/kg, 70 μg/kg, 65 μg/kg, 60 μg/kg, 55 μg/kg, 50 μg/kg, 45 μg/kg, 40 μg/kg, 35 μg/kg, 30 μg/kg, 26 μg/kg, 25 μg/kg, 20 μg/kg, 15 μg/kg, 13 μg/kg, 10 μg/kg, 6.5 μg/kg, 5 μg/kg, 3.2 μg/kg, 3 μg/kg, 2.5 μg/kg, 2 μg/kg, 1.6 μg/kg, 1.5 μg/kg, 1 μg/kg, 0.5 μg/kg, 0.25 μg/kg, 0.1 μg/kg, or 0.05 μg/kg of one or more anti-CD3 antibodies to prevent, treat or ameliorate one or more symptoms of an autoimmune disorder, particularly diabetes.

In a one embodiment, a subject is administered one or more doses of 200 μg/kg or less, 175 μg/kg or less, 150 μg/kg or less, 128 μg/kg or less, 100 μg/kg or less, 95 μg/kg or less, 90 μg/kg or less, 85 μg/kg or less, 80 μg/kg or less, 75 μg/kg or less, 70 μg/kg or less, 65 μg/kg or less, 60 μg/kg or less, 55 μg/kg or less, 50 μg/kg or less, 45 μg/kg or less, 40 μg/kg or less, 35 μg/kg or less, 30 μg/kg or less, 25 μg/kg or less, 20 μg/kg or less, 15 μg/kg or less, 10 μg/kg or less, 5 μg/kg or less, 2.5 μg/kg or less, 2 μg/kg or less, 1.5 μg/kg or less, 1 μg/kg or less, 0.5 μg/kg or less, 0.25 μg/kg or less, 0.1 μg/kg or less, or 0.05 μg/kg or less of one or more anti-CD3 antibody of the invention to prevent, treat or ameliorate one or more symptoms of an autoimmune disorder, such as but not limited to diabetes.

In particular embodiments, a subject is administered one or more doses of about 5-1200 μg/m$^2$, preferably, 51-826 μg/m$^2$. In another embodiment, a subject is administered one or more unit doses of 1200 μg/m$^2$, 1150 μg/m$^2$, 1100 μg/m$^2$, 1050 μg/m$^2$, 1000 μg/m$^2$, 950 μg/m$^2$, 900 μg/m$^2$, 850 μg/m$^2$, 800 μg/m$^2$, 750 μg/m$^2$, 700 μg/m$^2$, 650 μg/m$^2$, 600 μg/m$^2$, 550 μg/m$^2$, 500 μg/m$^2$, 450 μg/m$^2$, 400 μg/m$^2$, 350 μg/m$^2$, 300 μg/m$^2$, 250 μg/m$^2$, 200 μg/m$^2$, 150 μg/m$^2$, 100 μg/m$^2$, 50 μg/m$^2$, 40 μg/m$^2$, 30 μg/m$^2$, 20 μg/m$^2$, 15 μg/m$^2$, 10 μg/m$^2$, or 5 μg/m$^2$ of one or more anti-human CD3 antibodies to prevent, treat, slow the progression of, delay the onset of or ameliorate one or more symptoms of an autoimmune disorder or disease.

In another embodiment, the subject is administered a treatment regimen comprising one or more doses of a prophylactically or therapeutically effective amount of one or more anti-human CD3 antibodies, wherein the course of treatment is administered over 2 days, 3 days, 4 days, 5 days, 6 days, 7 days, 8 days, 9 days, 10 days, 11 days, 12 days, 13 days or 14 days. In one embodiment, the treatment regimen comprises administering doses of the prophylactically or therapeutically effective amount of one or more anti-human CD3 antibodies every day, every 2$^{nd}$ day, every 3$^{rd}$ day or every 4$^{th}$ day. In certain embodiments, the treatment regimen comprises administering doses of the prophylactically or therapeutically effective amount of one or more anti-human CD3 antibodies on Monday, Tuesday, Wednesday, Thursday of a given week and not administering doses of the prophylactically or therapeutically effective amount of one or more anti-human CD3 antibodies on Friday, Saturday, and Sunday of the same week until 14 doses, 13, doses, 13 doses, 12 doses, 11 doses, 10 doses, 9 doses, or 8 doses have been administered. In certain embodiments the dose administered is the same each day of the regimen. In certain embodiments, a subject is administered a treatment regimen comprising one or more doses of a prophylactically or therapeutically effective amount of one or more anti-human CD3 antibodies, wherein the prophylactically or therapeutically effective amount is 200 µg/kg/day, 175 µg/kg/day, 150 µg/kg/day, 125 µg/kg/day, 100 µg/kg/day, 95 µg/kg/day, 90 µg/kg/day, 85 µg/kg/day, 80 µg/kg/day, 75 µg/kg/day, 70 µg/kg/day, 65 µg/kg/day, 60 µg/kg/day, 55 µg/kg/day, 50 µg/kg/day, 45 µg/kg/day, 40 µg/kg/day, 35 µg/kg/day, 30 µg/kg/day, 26 µg/kg/day, 25 µg/kg/day, 20 µg/kg/day, 15 µg/kg/day, 13 µg/kg/day, 10 µg/kg/day, 6.5 µg/kg/day, 5 µg/kg/day, 3.2 µg/kg/day, 3 µg/kg/day, 2.5 µg/kg/day, 2 µg/kg/day, 1.6 µg/kg/day, 1.5 µg/kg/day, 1 µg/kg/day, 0.5 µg/kg/day, 0.25 µg/kg/day, 0.1 µg/kg/day, or 0.05 µg/kg/day; and/or wherein the prophylactically or therapeutically effective amount is 1200 µg/m$^2$/day, 1150 µg/m$^2$/day, 1100 µg/m$^2$/day, 1050 µg/m$^2$/day, 1000 µg/m$^2$/day, 950 µg/m$^2$/day, 900 µg/m$^2$/day, 850 µg/m$^2$/day, 800 µg/m$^2$/day, 750 µg/m$^2$/day, 700 µg/m$^2$/day, 650 µg/m$^2$/day, 600 µg/m$^2$/day, 550 µg/m$^2$/day, 500 µg/m$^2$/day, 450 µg/m$^2$/day, 400 µg/m$^2$/day, 350 µg/m$^2$/day, 300 µg/m$^2$/day, 250 µg/m$^2$ day, 200 µg/m$^2$/day, 150 µg/m$^2$/day, 100 µg/m$^2$/day, 50 µg/m$^2$/day, 40 µg/m$^2$ day, 30 µg/m$^2$/day, 20 µg/m$^2$/day, 15 µg/m$^2$/day, 10 µg/m$^2$/day, or 5 µg/m$^2$/day. In another embodiment, the intravenous dose of 1200 µg/m$^2$ or less, 1150 µg/m$^2$ or less, 1100 µg/m$^2$ or less, 1050 µg/m$^2$ or less, 1000 µg/m$^2$ or less, 950 µg/m$^2$ or less, 900 µg/m$^2$ or less, 850 µg/m$^2$ or less, 800 µg/m$^2$ or less, 750 µg/m$^2$ or less, 700 µg/m$^2$ or less, 650 µg/m$^2$ or less, 600 µg/m$^2$ or less, 550 µg/m$^2$ or less, 500 µg/m$^2$ or less, 450 µg/m$^2$ or less, 400 µg/m$^2$ or less, 350 µg/m$^2$ or less, 300 µg/m$^2$ or less, 250 µg/m$^2$ or less, 200 µg/m$^2$ or less, 150 µg/m$^2$ or less, 100 µg/m$^2$ or less, 50 µg/m$^2$ or less, 40 µg/m$^2$ or less, 30 µg/m$^2$ or less, 20 µg/m$^2$ or less, 15 µg/m$^2$ or less, 10 µg/m$^2$ or less, or 5 µg/m$^2$ or less of one or more anti CD3 antibodies is administered over about 24 hours, about 22 hours, about 20 hours, about 18 hours, about 16 hours, about 14 hours, about 12 hours, about 10 hours, about 8 hours, about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of type 1 diabetes. The total dosage over the duration of the regimen is preferably a total of less than 9000 µg/m$^2$, 8000 µg/m$^2$, 7000 µg/m$^2$, 6000 µg/m$^2$, and may be less than 5000 µg/m$^2$, 4000 µg/m$^2$, 3000 µg/m$^2$, 2000 µg/m$^2$, or 1000 µg/m$^2$. In specific embodiments, the total dosage administered in the regimen is 100 µg/m$^2$ to 200 µg/m$^2$, 100 µg/m$^2$ to 500 µg/m$^2$, 100 µg/m$^2$ to 1000 µg/m$^2$, or 500 µg/m$^2$ to 1000 µg/m$^2$.

In preferred embodiments, the dose escalates over the first fourth, first half or first ⅔ of the doses (e.g., over the first 2, 3, 4, 5, or 6 days of a 10, 12, 14, 16, 18 or 20 day regimen of one dose per day) of the treatment regimen until the daily prophylactically or therapeutically effective amount of one or more anti-human CD3 antibodies is achieved. In certain embodiments, a subject is administered a treatment regimen comprising one or more doses of a prophylactically or therapeutically effective amount of one or more anti-human CD3 antibodies, wherein the prophylactically or therapeutically effective amount is increased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 Ξg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, or 125 µg/kg each day; or increased by, e.g., 1 µg/m$^2$, 5 µg/m$^2$, 10 µg/m$^2$, 15 µg/m$^2$, 20 µg/m$^2$, 30 µg/m$^2$, 40 µg/m$^2$, 50 µg/m$^2$, 60 µg/m$^2$, 70 µg/m$^2$, 80 µg/m$^2$, 90 µg/m$^2$, 100 µg/m$^2$, 150 µg/m$^2$, 200 µg/m$^2$, 250 µg/m$^2$, 300 µg/m$^2$, 350 µg/m$^2$, 400 µg/m$^2$, 450 µg/m$^2$, 500 µg/m$^2$, 550 µg/m$^2$, 600 µg/m$^2$, or 650 µg/m$^2$, each day as treatment progresses. In certain embodiments, a subject is administered a treatment regimen comprising one or more doses of a prophylactically or therapeutically effective amount of one or more anti-human CD3 antibodies, wherein the prophylactically or therapeutically effective amount is increased by a factor of 1.25, a factor of 1.5, a factor of 2, a factor of 2.25, a factor of 2.5, or a factor of 5 until the daily prophylactically or therapeutically effective amount of one or more anti-human CD3 antibodies is achieved.

In a specific embodiment, a subject is intramuscularly administered one or more doses of a 200 µg/kg or less, preferably 175 µg/kg or less, 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti-CD3 antibodies to prevent, treat or ameliorate one or more symptoms of an autoimmune disorder.

In another embodiment, a subject is subcutaneously administered one or more doses of a 200 µg/kg or less, preferably 175 µg/kg or less, 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti-CD3 antibodies to prevent, treat or ameliorate one or more symptoms of an autoimmune disorder.

In another embodiment, a subject is intravenously administered one or more doses of a 100 µg/kg or less, preferably 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti CD3 antibodies to prevent, treat or ameliorate one or more symptoms of an autoimmune disorder. In another embodiment, the intravenous dose of 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti CD3 antibodies is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of an autoimmune disorder.

In specific embodiments in which escalating doses are administered for the first days of the dosing regimen, the dose on day 1 of the regimen is 5-100 µg/m²/day, preferably 51 µg/m²/day and escalates to the daily dose as recited immediately above by day 3, 4, 5, 6 or 7. For example, on day 1, the subject is administered a dose of approximately 51 µg/m²/day, on day 2 approximately 103 µg/m²/day, on day 3 approximately 207 µg/m²/day, on day 4 approximately 413 µg/m²/day and on subsequent days of the regimen (e.g., days 5-14) 826 µg/m²/day. In another embodiment, on day 1, the subject is administered a dose of approximately 227 µg/m² day, on day 2 approximately 459 µg/m²/day, on day 3 and subsequent days, approximately 919 µg/m²/day. In another embodiment, on day 1, the subject is administered a dose of approximately 284 µg/m² day, on day 2 approximately 574 µg/m²/day, on day 3 and subsequent days, approximately 1148 µg/m²/day.

In other embodiments, the initial dose is ¼, to ½, to equal to the daily dose at the end of the regimen but is administered in portions at intervals of 6, 8, 10 on 12 hours. For example, a 13 µg/kg/day dose is administered in four doses of 3-4 µg/kg at intervals of 6 hours to reduce the level of cytokine release caused by administration of the antibody.

In specific embodiments, to reduce the possibility of cytokine release and other adverse effects, the first 1, 2, 3, or 4 doses or all the doses in the regimen are administered more slowly by intravenous administration. For example, a dose of 51 µg/m²/day may be administered over about 5 minutes, about 15 minutes, about 30 minutes, about 45 minutes, about 1 hour, about 2 hours, about 4 hours, about 6 hours, about 8 hours, about 10 hours, about 12 hours, about 14 hours, about 16 hours, about 18 hours, about 20 hours, and about 22 hours. In certain embodiments, the dose is administered by slow infusion over a period of, e.g., 20 to 24 hours. In specific embodiments, the dose is infused in a pump, preferably increasing the concentration of antibody administered as the infusion progresses.

In other embodiments, a set fraction of the doses for the 51 µg/m²/day to 826 µg/m²/day regimen described above is administered in escalating doses. In certain embodiments, the fraction is ⅒, ¼, ⅓, ½, ⅔ or ¾ of the daily doses of the regimens described above. Accordingly, when the fraction is ⅒, the daily doses will be 5.1 µg/m² on day 1, 10.3 µg/m² on day 2, 20.7 g/m² on day 3, 41.3 µg/m² on day 4 and 82.6 µg/m² on days 5 to 14. When the fraction is ¼, the doses will be 12.75 µg/m² on day 1, 25.5 µg/m² on day 2, 51 µg/m² on day 3, 103 µg/m² on day 4, and 207 µg/m² on days 5 to 14. When the fraction is ⅓, the doses will be 17 µg/m² on day 1, 34.3 µg/m² on day 2, 69 µg/m² on day 3, 137.6 µg/m² on day 4, and 275.3 µg/m² on days 5 to 14. When the fraction is ½, the doses will be 25.5 µg/m² on day 1, 51 µg/m² on day 2, 103 µg/m² on day 3, 207 µg/m² on day 4, and 413 µg/m² on days 5 to 14. When the fraction is ⅔, the doses will be 34 µg/m² on day 1, 69 µg/m² on day 2, 137.6 µg/m² on day 3, 275.3 µg/m² on day 4, and 550.1 µg/m² on days 5 to 14. When the fraction is ¾, the doses will be 38.3 µg/m² on day 1, 77.3 µg/m² on day 2, 155.3 µg/m² on day 3, 309.8 µg/m² on day 4, and 620 µg/m² on days 5 to 14. In other embodiments, the regimen is identical to one of those described above but only over days 1 to 4, days 1 to 5, or days 1 to 6. For example, in a particular embodiment, the doses will be 17 µg/m² on day 1, 34.3 µg/m² on day 2, 69 µg/m² on day 3, 137.6 µg/m² on day 4, and 275.3 µg/m² on days 5 and 6.

In specific embodiments, the anti-human CD3 antibody is not administered by daily doses over a number of days, but is rather administered by infusion in an uninterrupted manner over 4 hours, 6 hours, 8 hours, 10 hours, 12 hours, 15 hours, 18 hours, 20 hours, 24 hours, 30 hours or 36 hours. The infusion may be constant or may start out at a lower dosage for, for example, the first 1, 2, 3, 5, 6, or 8 hours of the infusion and then increase to a higher dosage thereafter. Over the course of the infusion, the patient receives a dose equal to the amount administered in the 5 to 20 day regimens set forth above. For example, a dose of approximately 150 µg/m², 200 µg/m², 250 µg/m², 500 µg/m², 750 µg/m², 1000 µg/m², 1500 µg/m², 2000 µg/m², 3000 µg/m², 4000 µg/m², 5000 µg/m², 6000 µg/m², 7000 µg/m², 8000 µg/m², or 9000 µm². In particular, the speed and duration of the infusion is designed to minimize the level of free anti-human CD3 antibody in the subject after administration. In certain embodiments, the level of free anti-human CD3 antibody should not exceed 200 ng/ml free antibody. In addition, the infusion is designed to achieve a combined T cell receptor coating and modulation of at least 50%, 60%, 70%, 80%, 90%, 95% or of 100%.

In certain embodiments, the antibody administered according to these regimens is OKT3γ1 (ala-ala). In other embodiments the antibody is not OKT3γ1 (ala-ala) and is administered so as to achieve one or more pharmacokinetic parameters achieved by the administration of OKT3γ1 (ala-ala), e.g., by intravenous administration, such as the serum titer of the antibody administered at 1 day, 2 days, 3 days, 4 days, 5 days, 6 days, 7 days, 2 weeks, 3 weeks or 1 month after the last day of the dosing regime.

In certain embodiments, the anti-human CD3 antibody is administered so as to achieve a certain level of combined coating and modulation of T cell receptor complexes on T cells, as determined by methods well known in the art, see, e.g., Example 11 of U.S. patent application publication US 2003/0108548, which is hereby incorporated by reference in its entirety. In specific embodiments, the dosing regimen achieves a combined T cell receptor coating and modulation of at least 50%, 60%, 70%, 80%, 90%, 95% or of 100% with, in specific embodiments, little to no free anti-human CD3 antibody detected (for example, less than 200 ng/mL of the drug is detected in the blood of the patient.)

In other embodiments, the anti-human CD3 antibody is administered chronically to treat, prevent, or slow or delay the onset or progression, or ameliorate one or more symptoms of type 1 diabetes. For example, in certain embodiments, a low dose of the anti-human CD3 antibody is administered once a month, twice a month, three times per month, once a week or even more frequently either as an alternative to the 6 to 14 day dosage regimen discussed above or after administration of such a regimen to enhance or maintain its therapeutic effect. Such a low dose may be anywhere from 1 µg/m² to 100 µg/m², preferably, approximately 5 µg/m², 10 µg/m², 15 µg/m², 20 µg/m², 25 µg/m², 30 µg/m², 35 µg/m², 40 µg/m², 45 µg/m², or 50 µg/m².

In other embodiments, the subject may be re-dosed at some time subsequent to administration of the anti-human CD3 antibody dosing regimen, preferably, based upon one or more physiological parameters or may be done as a matter of course. Such redosing may be administered and/or the need for such redosing evaluated 2 months, 4 months, 6 months, 8 months, 9 months, 1 year, 15 months, 18 months, 2 years, 30 months or 3 years after administration of a dosing regimen and may include administering a course of treatment every 6 months, 9 months, 1 year, 15 months, 18 months, 2 years, 30 months or 3 years indefinitely.

In specific embodiments, subjects are administered a subsequent round of anti-human CD3 antibody treatment based upon measurements of one or a combination of the following: the CD4/CD8 cell ratio, CD8 cell count, CD4/CD3 inversion, CD4/CD25 cell ratio, CD4/FoxP3 cell ratio, CD4/CD40 cell ratio, CD4/IL-10 cell ratio, and/or a CD4/TGF-β cell ratio.

With respect to the treatment of management of Type 1 diabetes, other parameters for determining whether to administer a subsequent round of treatment include an appearance or an increase in anti-islet cell antibodies, such as GADAs, IA-2 antibodies or anti-insulin antibodies or an appearance or increase in the levels of T cells specific for islet cell antigens. Subsequent doses may be administered if the number of β-cells or β-cell activity or function decreases by 20%, 30%, 40%, 50%, 60%, 70%, 80% or 90% as compared to the α-cell number or activity or function during administration of the preceding round of treatment. α-cell function may be determined by any method know in the art, for example, the C peptide response to MMTT, OGTT, IGTT, or two-phase glucose clamp, or the First Phase Insulin Release (FPIR) test, as discussed above. Other parameters that may be used to determine whether to redose include the HA1 or HA1c levels, the need for administration of exogenous insulin or increase in the dosage of exogenous insulin by more than 0.1 U/kg/day, 0.2 U/kg/day, 0.5 U/kg/day, 0.6 U/kg/day, 1 U/kg/day, or 2 U/kg/day. For example, a subject may be administered a subsequent round of treatment when the C-peptide response or FPIR of the patient to MMTT, OGTT, IGTT or two phase glucose clamp procedure decreases by more than 1%, more than 5%, more than 10%, more than 20%, more than 30%, more than 40% or more than 50% of pretreatment levels. In particular embodiments, subjects are redosed if they have a C-peptide response to MMTT, OGTT, IGTT or two-phase glucose clamp procedure (preferably, MMTT) resulting in an AUC of less than 40 µmol/ml/240 min., less than 50 µmol/ml/240 min, less than 60 µmol/ml/240 min, less than 70 µmol/ml/240 min., less than 80 µmol/ml/240 min., or less than at least 90 µmol/ml/240 min. In specific embodiments, subjects may be redosed they have a FPIR of less than 300 µmol/l, less than 400 µmol/l, less than 500 µmol/l, less than 600 µmol/l, or less than 700 µmol/l, Also for example, a subject may be redosed when the subject's HA1 or HA1C levels increase by at least 5%, at least 10%, at least 20%, at least 30%, at least 40%, at least 50%, at least 60%, at least 70%, at least 80% or at least 90% compared to pre-treatment levels or the absolute levels are greater than 8%, greater than 7.5%, or greater than 7%. In other embodiments, the further doses may be administered based upon appearance of or increase in number (such as an increase by, on average, 1, 2, 3, 4, 5, 8, 10 15, or 20), duration and/or severity of hypoglycemic episodes or of ketoacidosis episodes on a daily, weekly or monthly basis.

In a specific embodiment, anti-human CD3 therapy is used in type 1 diabetes patients that have at least 99%, at least 95%, at least 90%, at least 85%, at least 80%, at least 75%, at least 70%, at least 75%, at least 60%, at least 50% residual β-cell function as compared to an individual with no indicators of diabetes or predisposition to diabetes in the same population (i.e., age, sex, race, and general health) and determined by methods described herein or known to one of ordinary skill in the art. In another embodiment, after a course of treatment with an anti-human CD3 antibody according to the invention, the level of β-cell function of the patient decreases by less than 1%, less than 5%, less than 10%, less than 20%, less than 30%, less than 40% or less than 50% of the pretreatment levels. In yet another embodiment of the invention, after a course of treatment with an anti-human CD3 antibody according to the invention, the level of β-cell function of the patient is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment. In another embodiment of the invention, after a course of treatment with an anti-human CD3 antibody according to the invention, the level of β-cell function of the patient is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment and the mean lymphocyte count of the patient is not less than 800 cells/ml, less than 750 cells/ml, less than 700 cells/ml, less than 650 cells/ml, less than 600 cells/ml, less than 550 cells/ml, less than 500 cells/ml, less than 400 cells/ml, less than 300 cells/ml or less than 200 cells/ml at the same time period. In another embodiment of the invention, after a course of treatment with an anti-human CD3 antibody according to the invention, the level of β-cell function of the patient is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment and the patient's mean platelet count is not less than 100,000,000 platelets/ml, less than 75,000,000 platelets/ml, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/ml or less than 100,000 platelets/ml.

In certain embodiments, one or more pharmaceutical compositions comprising one or more CD3 binding molecules (e.g., one or more anti-human CD3 antibodies) are administered to a subject having type 1 diabetes, to prevent or slow the reduction β-cell mass associated with autoimmune diabetes. In some embodiments, after a course of treatment with an anti-human CD3 antibody according to the invention, the level of β-cell mass of the patient decreases by less than 1%, less than 5%, less than 10%, less than 20%, less than 30%, less than 40%, less than 50%, less than 60%, or less than 70% of the pretreatment levels. In yet another embodiment of the invention, after a course of treatment with an anti-human CD3 antibody according to the invention, the level of β-cell function of the patient is maintained at least 99%, at least 95%, at least 90%, at least 80%, at least 70%, at least 60%, at least 50%, at least 40%, or at least 30% of pretreatment levels for at least 4 months, at least 6 months, at least 9 months, at least 12 months, at least 18 months, at least 24 months, or at least 30 months after the end of treatment. In another embodiment of the invention, after a course of treatment with an anti-human CD3 antibody according to the invention, the level of β cell function of the patient is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment and the mean lymphocyte count of the patient is not less than 800 cells/ml, less than 750 cells/ml, less than 700 cells/ml, less than 650 cells/ml, less than 600 cells/ml, less than 550 cells/ml, less than 500 cells/ml, less than 400 cells/ml, less than 300 cells/ml or less than 200 cells/ml over the same time period. In another embodiment of the invention, after a course of treatment with an anti-human CD3 antibody according to the invention the level of β-cell function of the patient is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment and the mean platelet count of the patient is not less than 100,000,000 platelets/ml, less than 75,000,000 platelets/ml, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/ml or less than 100,000 platelets/ml.

In the methods of the invention, the anti-human CD3 therapy is administered in patients that do not require daily insulin, or that have average insulin requirements of less than 0.05 U/kg/day, less than 0.1 U/kg/day, less than 0.2 U/kg/day, less than 0.4 U/kg/day, less than 0.6 U/kg/day, less than 0.8 U/kg/day, less than 1 U/kg/day, less than 2 U/kg/day, less than 5 U/kg/day, less than 10 U/kg/day or less than 50 U/kg/day. In another embodiment, a patient with an autoimmune diabetes disorder is administered a regimen of doses of a prophylactically or therapeutically effective amount of one or more anti-human CD3 antibodies to avoid or delay the need to administer insulin, or increase the dose of insulin administered for more than 6 months, 1 year, 18 months, 24 months, 30 months, 36 months, 5 years, 7 years or 10. In other embodiments, in patients who do require exogenous insulin, methods of the invention achieve a reduction in daily insulin requirement by at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, or at least 90% of pretreatment levels. In yet another embodiment of the invention in patients who require exogenous insulin, after a course of treatment with an anti-human CD3 antibody according to the invention, the reduction of a patient's daily insulin requirements by at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, or at least 90% of pretreatment levels is maintained for at least 4 months, at least 6 months, at least 9 months, at least 12 months, at least 18 months, at least 24 months, or at least 30 months after the course of treatment. In yet another embodiment of the invention, after a course of treatment with an anti-human CD3 antibody according to the invention, the reduction of a patient's daily insulin requirements by at least 10%, at least 15%, at least 20%, at least 25%, at least 30%, at least 40%, at least 45%, at least 50%, at least 55%, at least 60%, at least 65%, at least 70%, at least 75%, at least 80%, or at least 85% of pretreatment levels is maintained for at least 4 months, at least 6 months, at least 9 months, at least 12 months, at least 18 months, at least 24 months, or at least 30 months after the course of treatment and the mean lymphocyte count of the patient is not less than 800 cells/ml, less than 750 cells/ml, less than 700 cells/ml, less than 650 cells/ml, less than 600 cells/ml, less than 550 cells/ml, less than 500 cells/ml, less than 400 cells/ml, less than 300 cells/ml or less than 200 cells/ml over the same time period.

In other embodiments, in patients who do require exogenous insulin, methods of the invention result in an increase in the daily insulin requirement by no more than 1%, no more than 5%, no more than 10%, no more than 15%, no more than 20%, no more than 25%, no more than 30%, no more than 40%, no more than 45%, no more than 50%, no more than 55%, no more than 60%, no more than 65%, no more than 70%, or no more than 75% as compared to pretreatment levels. In yet another embodiment of the invention in patients who require exogenous insulin, after a course of treatment with an anti-human CD3 antibody according to the invention, the increase in a patient's daily insulin requirements by no more than 1%, no more than 5%, no more than 10%, no more than 15%, no more than 20%, no more than 25%, no more than 30%, no more than 40%, no more than 45%, no more than 50%, no more than 55%, no more than 60%, no more than 65%, no more than 70%, or no more than 75% of pretreatment levels is maintained for at least 4 months, at least 6 months, at least 9 months, at least 12 months, at least 18 months, at least 24 months, or at least 30 months after the course of treatment. In yet another embodiment of the invention, after a course of treatment with an anti-human CD3 antibody according to the invention, the increase in a patient's daily insulin requirements by no more than 1%, no more than 5%, no more than 10%, no more than 15%, no more than 20%, no more than 25%, no more than 30%, no more than 40%, no more than 45%, no more than 50%, no more than 55%, no more than 60%, no more than 65%, no more than 70%, or no more than 75% of pretreatment levels is maintained for at least 4 months, at least 6 months, at least 9 months, at least 12 months, at least 18 months, at least 24 months, or at least 30 months after the course of treatment and the mean lymphocyte count of the patient is not less than 800 cells/ml, less than 750 cells/ml, less than 700 cells/ml, less than 650 cells/ml, less than 600 cells/ml, less than 550 cells/ml, less than 500 cells/ml, less than 400 cells/ml, less than 300 cells/mil or less than 200 cells/mil over the same time period.

In yet another embodiment, a human subject having type 1 diabetes, or a human identified as having a predisposition to developing type 1 diabetes is administered a course of a prophylactically or therapeutically effective amount of one or more anti-human CD3 antibodies to preserve the subject's C-peptide response or FPIR to MMTT, OGTT, IGTT or two phase glucose clamp procedure over about 2 weeks, about 1 month, about 2 months, about 4 months, about 5 months, about 6 months, about 7 months, about 8 months, about 9 months, about 10 months, about 11 months, about 12 months, about 15 months, about 18 months, about 21 months or about 24 months after treatment. In preferred embodiments, the patients initially have a C-peptide response to MMTT, OGTT, IGTT, or two-phase glucose clamp procedure (preferably MMTT) resulting in an area under curve (AUC) of at least 80 pmol/ml/240 min., preferably, at least 90 pmol/ml/240 min., more preferably at least 100 pmol/ml/240 min., or even at least 110 pmol/ml/240 min. In preferred embodiments, the patients prior to treatment with an anti-human CD3 antibody according to the invention have a FPIR of at least 300 pmol/l, at least 350 pmol/l, at least 400 pmol/l, at least 450 pmol/l, at least 500 pmol/l, preferably, at least 550 pmol/l, more preferably at least 600 pmol/l, or even at least 700 pmol/l. In another embodiment of the invention, after a course of treatment with an anti-human CD3 antibody according to the invention, the C-peptide response or FPIR of the patient to MMTT, OGTT, IGTT, or two-phase glucose clamp procedure decreases by less than 1%, less than 5%, less than 10%, less than 20%, less than 30%, less than 40% or less than 50% of the pretreatment levels. In yet another embodiment of the invention, after a course of treatment with an anti-human CD3 antibody according to the invention, the C-peptide response or FPIR of the patient to MMTT, OGTT, IGTT or two phase glucose clamp procedure is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the course of treatment. In another embodiment of the invention, after a course of treatment with an anti-human CD3 antibody according to the invention, the C-peptide response or FPIR of the patient to MMTT, OGTT, IGTT or two phase glucose clamp procedure is maintained at least 99%, at least 95%, at least 90%, at least 80%, at least 70%, at least 60%, or at least 50% of pretreatment levels for at least 4 months, at least 6 months, at least 9 months, at least 12 months, at least 18 months, at least 24 months, or at least 30 months after the end of treatment and the mean lymphocyte count of the patient is not less than 800 cells/ml, less than 750 cells/ml, less than 700 cells/ml, less than 650 cells/ml, less than 600 cells/ml, less than 550 cells/ml, less than 500 cells/ml, less than 400 cells/ml, less than 300 cells/ml or less than 200 cells/ml over the same time period.

In particular embodiments, the invention provides methods of treatment such that a single round of treatment or round of treatment every 6 months, every 9 months, every 12 months, every 15 months, every 18 months, or every 24 months with an anti-human CD3 antibody (preferably, without any intervening treatment with anti-human CD3 antibodies), results in a level of HA1 or HA1c that is 7% or less, 6.5% or less, 6% or less, 5.5% or less, or 5% or less 6 months, 9 months, 12 months, 15 months, 18 months, or 24 months after the previous round of treatment or the first round of treatment. In specific embodiments, after a single round of treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the patients have a C-peptide response to MMTT, OGTT, IGTT or two-phase glucose clamp procedure (preferably, MMTT) resulting in an AUC of at least 40 pmol/ml/240 min., 50 pmol/ml/240 min, 60 pmol/ml/240 min, 70 pmol/ml/240 min., 80 pmol/ml/240 min., preferably, at least 90 pmol/ml/240 min., more preferably at least 100 pmol/ml/240 min., or even at least 110 pmol/mV/240 min, said response determined 6 months, 9 months, 12 months, 15 months, 18 months, or 24 months after the previous round of treatment or after the previous round of treatment. In specific embodiments, after a single round of treatment or round of treatment every 6 months, every 9 months, every 12 months, every 15 months, every 18 months, or every 24 months with an anti-human CD3 antibody according to the methods of the invention (preferably, without any intervening treatment with anti-human CD3 antibodies), the patients have a FPIR of at least 300 pmol/l, at least 400 pmol/l, preferably, at least 500 pmol/l, more preferably at least 600 pmol/l, or even at least 700 pmol/l, said FPIR determined at 6 months, 9 months, 12 months, 15 months, 18 months, or 24 months after the previous round of treatment or initial round of treatment.

In another embodiment, with respect to the treatment of MS, pharmaceutical compositions comprising one or more CD3 binding molecules (e.g., one or more anti-CD3 antibodies) are administered one or more times to prevent or reduce an increase, or slow or reduce an increase in EDSS score associated with MS in a subject. In yet another embodiment, one or more pharmaceutical compositions comprising one or more CD3 binding molecules (e.g., one or more anti-CD3 antibodies) are administered one or more times to prevent an increase in the frequency, severity and/or duration of attacks associated with MS in a subject. In still other embodiments, one or more pharmaceutical compositions comprising one or more CD3 binding molecules (e.g., one or more anti-CD3 antibodies) are administered one or ore times to prevent an increase in number and/or total volume of lesions, as detected by, e.g., MRI, associated with MS in a subject. In accordance with these embodiments, the subject's EDSS score and/or a determination of the frequency, duration and/or severity of attacks maybe assessed by a qualified medical practitioner according to methods commonly accepted and well known in the art. In certain embodiments, the subject has benign MS. In other embodiments, the subject has RRMS, SPMS, PRMS, or PPMS. In certain embodiments, one or more pharmaceutical compositions comprising one or more CD3 binding molecules (e.g., one or more anti-CD3 antibodies) are administered one or more times to reduce the incidence, severity and/or duration of a symptom associated with MS in a subject, wherein said symptoms are described herein or are known in the art. In certain embodiments, symptoms associated with MS include, but are not limited to fatigue, disturbances of vision, disturbances of strength, disturbances of coordination, disturbances of balance, disturbances of bladder/bowel function, weakness or paralysis in one or more extremities, tremor in one or more extremities, muscle spasticity, muscle atropy, dysfunctional movement, numbness or abnormal sensation in any area, tingling, facial pain, extremity pain, loss of vision in one or both eyes, double vision, eye discomfort, uncontrollable rapid eye movements, decreased coordination, loss of balance, decreased ability to control small or intricate movements, walking or gait abnormalities, muscle spasms, dizziness, vertigo, urinary hesitancy, urinary urgency, increased urinary frequency, incontinence, decreased memory, decreased spontaneity, decreased judgment, loss of ability to think abstractly, loss of ability to generalize, depression, decreased attention span, slurred speech, difficulty speaking or understanding speech, fatigue, constipation, hearing loss, and/or positive Babinski's reflex.

In a specific embodiment anti-CD3 therapy is used for the treatment of MS in patients that have a disability score according to the Kurtzke Expanded Disability Scale (EDSS) of 1.0, 1.5, 2.0, 2.5, 3.0, 3.5, 4.0, 4.5, 5.0, 5.5, 6.0, 6.5, 7.0, 7.5, 8.0, 8.5, 9.0 or 9.5 as determined by methods described herein or known to one of ordinary skill in the art. In another embodiment, after one or more courses of treatment with an anti-CD3 antibody according to the invention the EDSS score of the patient increases by not more than one-half step, not more than one step, not more than one and one-half steps, not more than two steps, not more than two and one-half steps, not more than three steps, not more than three and one-half steps, not more than four steps, not more than four an one-half steps, not more than more than five steps, not more than five and one-half steps, not more than six steps, not more than six and one-half steps, not more than seven steps, not more than seven and one-half steps, not more than eight steps, or not more than eight and one-half steps relative to the pretreatment score.

In yet another embodiment of the invention, after one or more courses of treatment with an anti-CD3. antibody according to the invention the EDSS score of the patient is maintained or increases by not more than one-half step, not more than one step, not more than one and one-half steps, not more than two steps, not more than two and one-half steps, not more than three steps, not more than three and one-half steps, not more than four steps, not more than four an one-half steps, not more than more than five steps, not more than five and one-half steps, not more than six steps, not more than six and one-half steps, not more than seven steps, not more than seven and one-half steps, not more than eight steps, or not more than eight and one-half steps relative to the pretreatment score for at least 4 months, at least 6 months, at least 9 months, at least 12 months, at least 15 months, at least 18 months, at least 24 months, at least 2.5 years or at least 3 years after the end of treatment.

In another embodiment of the invention, after one or more courses of treatment with an anti-CD3 antibody according to the invention the EDSS score of the patient is maintained or increases by not more than one-half step, not more than one step, not more than one and one-half steps, not more than two steps, not more than two and one-half steps, not more than three steps, not more than three and one-half steps, not more than four steps, not more than four an one-half steps, not more than more than five steps, not more than five and one-half steps, not more than six steps, not more than six and one-half steps, not more than seven steps, not more than seven and one-half steps, not more than eight steps, or not more than eight and one-half steps relative to the pretreatment score for at least 4 months, at least 6 months, at least 9 months, at least 12 months, at least 15 months, at least 18 months, at least 24 months, at least 2.5 years or at least 3 years after the end of treatment and does not reduce the mean lymphocyte count of the patient to less than 800 cells/ml, less than 750 cells/mil, less than 700 cells/ml, less than 650 cells/ml, less than 600 cells/ml, less than 550 cells/ml, less than 500 cells/ml, less than 400 cells/ml, less than 300 cells/ml or 200 cells/ml or less.

In another embodiment of the invention, after one or more courses of treatment with an anti-CD3 antibody according to the invention the EDSS score of the patient is maintained or increases by not more than one-half step, not more than one step, not more than one and one-half steps, not more than two steps, not more than two and one-half steps, not more than three steps, not more than three and one-half steps, not more than four steps, not more than four an one-half steps, not more than more than five steps, not more than five and one-half steps, not more than six steps, not more than six and one-half steps, not more than seven steps, not more than seven and one-half steps, not more than eight steps, or not more than eight and one-half steps relative to the pretreatment score for at least 4 months, at least 6 months, at least 9 months, at least 12 months, at least 15 months, at least 18 months, at least 24 months, at least 2.5 years or at least 3 years after the end of treatment and does not reduce the mean platelet count of the patient to less than 100,000,000 platelets/ml, less than 75,000,000 platelets/ml, less than 50,000,000 platelets/ml, less than 25,000,000 platelets/ml, less than 1,000,000 platelets/ml, less than 750,000 platelets/mil, less than 500,000 platelets/ml, less than 250,000 platelets/mil, less than 150,000 platelets/ml or 100,000 platelets/ml or less.

In other embodiments, after one or more courses of treatment with an anti-CD3 antibody according to the invention the average incidence, frequency, severity or duration of symptoms and/or attacks associated with MS in a patient increases by not more than 2%, 5%, 10%, 15%, 20%, 25%, 30%, 35%, 40%, 45%, 50%, 55%, 60%, b5%, 70% or 75% relative to the pretreatment condition. In yet another embodiment of the invention, after one or more courses of treatment with an anti-CD3 antibody according to the invention the average incidence, frequency, severity or duration of symptoms and/or attacks associated with MS in a patient increases by not more than 2%, 5%, 10%, 15%, 20%, 25%, 30%, 35%, 40%, 45%, 50%, 55%, 60%, 65%, 70% or 75% relative to the pretreatment condition for at least 4 months, at least 6 months, at least 9 months, at least 12 months, at least 15 months, at least 18 months, at least 24 months, at least 2.5 years or at least 3 years after the end of treatment.

In another embodiment of the invention, after one or more courses of treatment with an anti-CD3 antibody according to the invention the average frequency, severity or duration of symptoms and/or attacks associated with MS in a patient increases by not more than 2%, 5%, 10%, 15%, 20%, 25%, 30%, 35%, 40%, 45%, 50%, 55%, 60%, 65%, 70% or 75% relative to the pretreatment condition for at least 4 months, at least 6 months, at least 9 months, at least 12 months, at least 15 months, at least 18 months, at least 24 months, at least 2.5 years or at least 3 years after the end of treatment and does not reduce the mean lymphocyte count of the patient to less than 800 cells/ml, less than 750 cells/ml, less than 700 cells/ml, less than 650 cells/ml, less than 600 cells/ml, less than 550 cells/ml, less than 500 cells/ml, less than 400 cells/ml, less than 300 cells/ml or 200 cells/ml or less.

In another embodiment of the invention, after one or more courses of treatment with an anti-CD3 antibody according to the invention the average frequency, severity or duration of symptoms and/or attacks associated with MS in a patient increases by not more than 2%, 5%, 10%, 15%, 20%, 25%, 30%, 35%, 40%, 45%, 50%, 55%, 60%, 65%, 70% or 75% relative to the pretreatment condition for at least 4 months, at least 6 months, at least 9 months, at least 12 months, at least 15 months, at least 18 months, at least 24 months, at least 2.5 years or at least 3 years after the end of treatment and does not reduce the mean platelet count of the patient to less than 100,000,000 platelets/ml, less than 75,000,000 platelets/mil, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/ml or 100,000 platelets/ml or less.

In another specific embodiment, after one or more courses of treatment with an anti-CD3 antibody according to the invention the number and/or total volume of lesions associated with MS as determined by MRI in a patient increases by not more than 2%, 5%, 10%, 15%, 20%, 25%, 30%, 35%, 40%, 45%, 50%, 55%, 60%, 65%, 70% or 75% of the pretreatment condition. In yet another embodiment of the invention, after one or more courses of treatment with an anti-CD3 antibody according to the invention the number and/or total volume of lesions associated with MS as determined by MRI in a patient increases by not more than 2%, 5%, 10%, 15%, 20%, 25%, 30%, 35%, 40%, 45%, 50%, 55%, 60%, 65%, 70% or 75% relative to the pretreatment condition for at least 4 months, at least 6 months, at least 9 months, at least 12 months, at least 15 months, at least 18 months, at least 24 months, at least 2.5 years or at least 3 years after the end of treatment.

In another embodiment of the invention, after one or more courses of treatment with an anti-CD3 antibody according to the invention the number and/or total volume of lesions associated with MS as determined by MRI in a patient increases by not more than 2%, 5%, 10%, 15%, 20%, 25%, 30%, 35%, 40%, 45%, 50%, 55%, 60%, 65%, 70% or 75% relative to the pretreatment condition for at least 4 months, at least 6 months, at least 9 months, at least 12 months, at least 15 months, at least 18 months, at least 24 months, at least 2.5 years or at least 3 years after the end of treatment and does not reduce the mean lymphocyte count of the patient to less than 800 cells/ml, less than 750 cells/ml, less than 700 cells/ml, less than 650 cells/ml, less than 600 cells/ml, less than 550 cells/ml, less than 800 cells/ml, less than 400 cells/ml, less than 300 cells/ml or 200 cells/ml or less.

In another embodiment of the invention, after one or more courses of treatment with an anti-CD3 antibody according to the invention the number and/or total volume of lesions associated with MS as determined by MRI in a patient increases by not more than 2%, S %, 10%, 1S %, 20%, 2S %, 30%, 3S %, 40%, 4S %, SO %, SS %, 60%, 6S %, 70% or 7S % relative to the pretreatment condition for at least 4 months, at least 6 months, at least 9 months, at least 12 months, at least 15 months, at least 18 months, at least 24 months, at least 2.5 years or at least 3 years after the end of treatment and does not reduce the mean platelet count of the patient to less than 100,000,000 platelets/ml, less than 75,000,000 platelets/ml, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/mil or 100,000 platelets/ml or less.

In another specific embodiment, after one or more courses of treatment with an anti-CD3 antibody according to the invention the Psoriasis Area and Severity Index (PASI) score of a patient having psoriasis decreases by at least 20%, at least 35%, at least 30%, at least 40%, at least 45%, at least 50%, at least 55%, at least 60%, at least 65%, at least 70%, at least 75%, at least 80%, or at least 85% relative to the pretreatment condition. In yet another embodiment of the invention, after one or more courses of treatment with an anti-CD3 antibody according to the invention the Psoriasis Area and Severity Index (PASI) score of a patient having psoriasis decreases by at least 20%, at least 35%, at least 30%, at least 40%, at least 45%, at least 50%, at least 55%, at least 60%, at least 65%, at least 70%, at least 75%, at least 80%, or at least 85% relative to the pretreatment condition for at least 4 months, at least 6 months, at least 9 months, at least 12 months, at least 15 months, at least 18 months, at least 24 months, at least 2.5 years or at least 3 years after the end of treatment.

In another embodiment of the invention, after one or more courses of treatment with an anti-CD3 antibody according to the invention the Psoriasis Area and Severity Index (PASI) score of a patient diagnosed with psoriasis decreases by at least 20%, at least 35%, at least 30%, at least 40%, at least 45%, at least 50%, at least 55%, at least 60%, at least 65%, at least 70%, at least 75%, at least 80%, or at least 85% relative to the pretreatment condition for at least 4 months, at least 6 months, at least 9 months, at least 12 months, at least 15 months, at least 18 months, at least 24 months, at least 2.5 years or at least 3 years after the end of treatment and does not reduce the mean lymphocyte count of the patient to less than 800 cells/ml, less than 750 cells/ml, less than 700 cells/ml, less than 650 cells/ml, less than 600 cells/ml, less than 550 cells/ml, less than 800 cells/ml, less than 400 cells/ml, less than 300 cells/mil or 200 cells/ml or less.

In another embodiment of the invention, after one or more courses of treatment with an anti-CD3 antibody according to the invention the Psoriasis Area and Severity Index (PASI) score of a patient diagnosed with psoriasis decreases by at least 20%, at least 35%, at least 30%, at least 40%, at least 45%, at least 50%, at least 55%, at least 60%, at least 65%, at least 70%, at least 75%, at least 80%, or at least 85% relative to the pretreatment condition for at least 4 months, at least 6 months, at least 9 months, at least 12 months, at least 15 months, at least 18 months, at least 24 months, at least 2.5 years or at least 3 years after the end of treatment and does not reduce the mean platelet count of the patient to less than 100,000,000 platelets/ml, less than 75,000,000 platelets/ml, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/ml or 100,000 platelets/ml or less.

In another specific embodiment, after one or more courses of treatment with an anti-CD3 antibody according to the invention the global assessment score of a patient diagnosed with psoriasis improves by at least by at least 25%, at least 35%, at least 30%, at least 40%, at least 45%, at least 50%, at least 55%, at least 60%, at least 65%, at least 70%, at least 75%, at least 80%, at least 85%, at least 90%, or at least 95% relative to pretreatment condition. In yet another embodiment of the invention, after one or more courses of treatment with an anti-CD3 antibody according to the invention the global assessment score of a patient diagnosed with psoriasis improves by at least by at least 25%, at least 35%, at least 30%, at least 40%, at least 45%, at least 50%, at least 55%, at least 60%, at least 65%, at least 70%, at least 75%, at least 80%, at least 85%, at least 90%, or at least 95% relative to pretreatment condition for at least 4 months, at least 6 months, at least 9 months, at least 12 months, at least 15 months, at least 18 months, at least 24 months, at least 2.5 years or at least 3 years after the end of treatment.

In another embodiment of the invention, after one or more courses of treatment with an anti-CD3 antibody according to the invention the global assessment score of a patient diagnosed with psoriasis improves by at least by at least 25%, at least 35%, at least 30%, at least 40%, at least 45%, at least 50%, at least 55%, at least 60%, at least 65%, at least 70%, at least 75%, at least 80%, at least 85%, at least 90%, or at least 95% relative to pretreatment condition for at least 4 months, at least 6 months, at least 9 months, at least 12 months, at least 15 months, at least 18 months, at least 24 months, at least 2.5 years or at least 3 years after the end of treatment and does not reduce the mean lymphocyte count of the patient to less than 800 cells/ml, less than 750 cells/ml, less than 700 cells/ml, less than 650 cells/ml, less than 600 cells/ml, less than 550 cells/ml, less than 800 cells/ml, less than 400 cells/mil, less than 300 cells/ml or 200 cells/ml or less.

In another embodiment of the invention, after one or more courses of treatment with an anti-CD3 antibody according to the invention the global assessment score of a patient diagnosed with psoriasis improves by at least by at least 25%, at least 35%, at least 30%, at least 40%, at least 45%, at least 50%, at least 55%, at least 60%, at least 65%, at least 70%, at least 75%, at least 80%, at least 85%, at least 90%, or at least 95% relative to pretreatment condition for at least 4 months, at least 6 months, at least 9 months, at least 12 months, at least 15 months, at least 18 months, at least 24 months, at least 2.5 years or at least 3 years after the end of treatment and does not reduce the mean platelet count of the patient to less than 100,000,000 platelets/ml, less than 75,000,000 platelets/ml, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/ml or 100,000 platelets/ml or less.

In another specific embodiment, after one or more courses of treatment with an anti-CD3 antibody according to the invention the subject's condition as assessed by any arthritis severity scale known in the art (e.g., RASS) improves by at least 25%, at least 35%, at least 30%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition. In yet another embodiment of the invention, after one or more courses of treatment with an anti-CD3 antibody according to the invention the subject's condition as assessed by any arthritis severity scale known in the art (e.g., RASS) improves by at least 25%, at least 35%, at least 30%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition for at least 4 months, at least 6 months, at least 9 months, at least 12 months, at least 15 months, at least 18 months, at least 24 months, at least 2.5 years or at least 3 years after the end of treatment.

In another embodiment of the invention, after one or more courses of treatment with an anti-CD3 antibody according to the invention the subject's condition as assessed by any arthritis severity scale known in the art (e.g., RASS) improves by at least 25%, at least 35%, at least 30%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition for at least 4 months, at least 6 months, at least 9 months, at least 12 months, at least 15 months, at least 18 months, at least 24 months, at least 2.5 years or at least 3 years after the end of treatment and does not reduce the mean lymphocyte count of the patient to less than 800 cells/ml, less than 750 cells/ml, less than 700 cells/ml, less than 650 cells/ml, less than 600 cells/ml, less than 550 cells/ml, less than 800 cells/mil, less than 400 cells/ml, less than 300 cells/ml or 200 cells/ml or less.

In another embodiment of the invention, after one or more courses of treatment with an anti-CD3 antibody according to the invention the subject's condition as assessed by any arthritis severity scale known in the art (e.g., RASS) improves by at least 25%, at least 35%, at least 30%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition for at least 4 months, at least 6 months, at least 9 months, at least 12 months, at least 15 months, at least 18 months, at least 24 months, at least 2.5 years or at least 3 years after the end of treatment and does not reduce the mean platelet count of the patient to less than 100,000,000 platelets/ml, less than 75,000,000 platelets/mil, less than 50,000,000 platelets/ml, less than 25,000,000 platelets/ml, less than 1,000,000 platelets/ml, less than 750,000 platelets/ml, less than 500,000 platelets/ml, less than 250,000 platelets/ml, less than 150,000 platelets/ml or 100,000 platelets/ml or less.

In another specific embodiment, after one or more courses of treatment with an anti-CD3 antibody according to the invention the absolute number, or proportion, of the subject's autoreactive CTLs as determined by immunospot assay (e.g., ELISPOT) decreases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition. In yet another embodiment of the invention, after one or more courses of treatment with an anti-CD3 antibody according to the invention the absolute number, or proportion, of the subject's autoreactive CTLs as determined by immunospot assay (e.g., ELISPOT) decreases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition for at least 4 months, at least 6 months, at least 9 months, at least 12 months, at least 15 months, at least 18 months, at least 24 months, at least 2.5 years or at least 3 years after the end of treatment.

In another embodiment of the invention, after one or more courses of treatment with an anti-CD3 antibody according to the invention the absolute number, or proportion, of the subject's autoreactive CTLs as determined by immunospot assay (e.g., ELISPOT) decreases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition for at least 4 months, at least 6 months, at least 9 months, at least 12 months, at least 15 months, at least 18 months, at least 24 months, at least 2.5 years or at least 3 years after the end of treatment and does not reduce the mean lymphocyte count of the patient to less than 800 cells/ml, less than 750 cells/ml, less than 700 cells/ml, less than 650 cells/ml, less than 600 cells/ml, less than 550 cells/ml, less than 800 cells/ml, less than 400 cells/ml, less than 300 cells/ml or 200 cells/ml or less.

In another embodiment of the invention, after one or more courses of treatment with an anti-CD3 antibody according to the invention the absolute number, or proportion, of the subject's autoreactive CTLs as determined by immunospot assay (e.g., ELISPOT) decreases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to pretreatment condition for at least 4 months, at least 6 months, at least 9 months, at least 12 months, at least 15 months, at least 18 months, at least 24 months, at least 2.5 years or at least 3 years after the end of treatment and does not reduce the mean platelet count of the patient to less than 100,000,000 platelets/ml, less than 75,000,000 platelets/ml, less than 50,000,000 platelets/mil, less than 25,000,000 platelets/ml, less than 1,000,000 platelets/ml, less than 750,000 platelets/ml, less than 500,000 platelets/ml, less than 250,000 platelets/ml, less than 150,000 platelets/ml or 100,000 platelets/ml or less.

In preferred embodiments, the anti-human CD3 antibodies are administered parenterally, for example, intravenously, intramuscularly or subcutaneously, or, alternatively, are administered orally. The anti-human CD3 antibodies may also be administered as a sustained release formulation.

In a specific embodiment, the mean absolute lymphocyte count in a subject with an autoimmune disorder is assessed before and/or after the administration of one or more doses of a prophylactically or therapeutically effective amount of one or more anti-human CD3 antibodies to determine whether one or more subsequent doses of a prophylactically or therapeutically effective amount of one or more anti-human CD3 antibodies should be administered to said subject. In another embodiment, the mean absolute lymphocyte count in a subject with an autoimmune disorder is assessed before and/or after the administration of one or more doses of a prophylactically or therapeutically effective amount of one or more anti-human CD3 antibodies to determine whether one or more subsequent doses of a prophylactically or therapeutically effective amount of one or more anti-human CD3 antibodies should be administered to said subject. Preferably, a subsequent dose of a prophylactically or therapeutically effective amount of one or more anti-human CD3 antibodies is not administered to said subject if the lymphocyte count is less than 800 cells/mm$^3$, less than 750 cells/mm$^3$, less than 700 cells/mm$^3$, less than 650 cells/mm$^3$, less than 600 cells/mm$^3$, less than 500 cells/mm$^3$, less than 400 cells/mm$^3$ or less than 300 cells/mm$^3$.

In another embodiment, the mean absolute lymphocyte count in a subject with an autoimmune disorder is determined prior to the administration of a first dose of a prophylactically or therapeutically effective amount of one or more anti-human CD3 antibodies and the mean absolute lymphocyte count is monitored prior to the administration of one or more subsequent doses of a prophylactically or therapeutically effective amount of one or more anti-human CD3 antibodies. Preferably, the mean absolute lymphocyte count in the subject is at least 900 cells/mm$^3$, preferably at least 950 cells/mm$^3$, at least 1000 cells/mm$^3$, at least 1050 cells/mm$^3$, at least 1100 cells/mm$^3$, at least 1200 cells/mm$^3$, or at least 1250 cells/mm$^3$ prior to the administration of a first dose of one or more anti-human CD3 antibodies.

In another embodiment, a mean absolute lymphocyte count of approximately 700 cells/ml to approximately 1200 cells/ ml, approximately 700 cells/ml to approximately 1100 cells/ml, approximately 700 cells/ml to approximately 1000 cells/ml, approximately 700 to approximately 900 cells/ml, approximately 750 cells/ml to approximately 1200 cells/ml, approximately 750 cells/ml to approximately 1100 cells/ml, approximately 750 cells/ml to approximately 1000 cells/ml, approximately 750 cells/ml to approximately 900 cells/ml, approximately 800 cells/ml to approximately 1200 cells/ml, approximately 800 cells/ml to approximately 1100 cells/ml, approximately 800 cells/ml to approximately 1000 cells/ml, approximately 900 cells/ml to approximately 1200 cells/ml, approximately 900 cells/mil to approximately 1100 cells/ml, approximately 900 cells/ml to approximately 1000 cells/ml, or approximately 1000 cells to approximately 1200 cells/ml is maintained in a subject having type 1 diabetes disorder by administering one or more doses of a prophylactic ally or therapeutically effective amount of one or more anti-human CD3 antibodies. In another embodiment, a mean absolute lymphocyte count of approximately 700 cells/ml to below 1000 cells/m$^1$ is maintained in a subject having an autoimmune disorder by administering one or more doses of a prophylactic ally or therapeutically effective amount of one or more anti-human CD3 antibodies.

In a specific embodiment, the administration of one or more doses or a dosage regimen of a prophylactically or therapeutically effective amount of one or more anti-human CD3 antibodies does not induce or reduces relative to other immunosuppressive agents one or more of the following unwanted or adverse effects: vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, vasodilatation, an increased risk of opportunistic infection, activation of Epstein Barr Virus, apoptosis of T cells and an increased risk of developing certain types of cancer. In another specific embodiment, the administration of one or more doses of a prophylactically or therapeutically effective amount of one or more anti-human CD3 antibodies does not induce or reduces relative to other immunosuppressive agents one or more of the following unwanted or adverse effects: vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, vasodilatation, an increased risk of opportunistic infection, Epstein Barr Virus activation, apoptosis of T cells, and an increased risk of developing certain types of cancer.

In accordance with the invention, the dose or dosage regimen comprising a prophylactically or therapeutically effective amount of one or more anti-CD3 antibodies for the treatment of an autoimmune disorder may be repeated at 1 month, 2 months, 4 months, 6 months, 8 months, 12 months, 15 months, 18 months or 24 months or longer after the initial or previous dose or dosage regimen comprising a prophylactically or therapeutically effective amount of one or more anti-CD3 antibodies. The repeat dose or dosage regimen may be administered as a matter of course, when symptoms associated with said autoimmune disorder recur after an improvement following the initial or previous dose or dosage regimen, or when symptoms associated with said autoimmune disorder do not improve after the initial dose or dosage regimen of anti-CD3 antibodies according to methods of the invention.

With respect to diabetes, a repeat dose or dosage regimen comprising a prophylactically or therapeutically effective amount of one or more anti-CD3 antibodies may be administered to a subject when, for example, the subject's average daily insulin use at 1 month, 2 months, 4 months, 6 months, 8 months, 12 months, 15 months, 18 months or 24 months or longer after initial or previous treatment with anti-CD3 antibodies does not decrease by at least 5%, at least 10%, at least 20%, at least 30%, at least 40%, at least 50%, at least 60%, at least 70%, at least 80% or at least 90% compared to pre-treatment levels. Alternatively, with respect to diabetes, a repeat dose or dosage regimen comprising a prophylactically or therapeutically effective amount of one or more anti-CD3 antibodies may be administered to a subject when, for example, the subject's HA 1 or HA 1 C levels at 1 month, 2 months, 4 months, 6 months, 8 months, 12 months, 15 months, 18 months or 24 months or longer after initial or previous treatment with anti-CD3 antibodies do not decrease by at least 5%, at least 10%, at least 20%, at least 30%, at least 40%, at least 50%, at least 60%, at least 70%, at least 80% or at least 90% compared to pre-treatment levels. In another embodiment, with respect to diabetes, a repeat dose or dosage regimen comprising a prophylactically or therapeutically effective amount of one or more anti-CD3 antibodies may be administered to a subject when, for example, the subject's C-peptide response at 1 month, 2 months, 4 months, 6 months, 8 months, 12 months, 15 months, 18 months or 24 months or longer after initial or previous treatment with anti-CD3 antibodies decreases by more than 5%, more than 10%, more than 20%, more than 30%, more than 40%, more than 50%, more than 60%, more than 70%, more than 80% or more than 90% compared to pre-treatment levels.

5.2.8 Combinatorial Therapy

The present invention provides compositions comprising one or more anti-human CD3 antibody and one or more prophylactic or therapeutic agents other than anti-human CD3 antibodies, and methods for preventing, treating, delaying the onset of, slowing the progression of or ameliorating one or more symptoms associated with an autoimmune disorder, e.g., an inflammatory autoimmune disorder, in a subject in need thereof comprising administering to said subject one or more of said compositions. Therapeutic or prophylactic agents include, but are not limited to, peptides, polypeptides, fusion proteins, nucleic acid molecules, small molecules, mimetic agents, synthetic drugs, inorganic molecules, and organic molecules. Any agent which is known to be useful, or which has been used or is currently being used for the prevention, treatment or amelioration of one or more symptoms associated with an autoimmune disorder, particularly type 1 diabetes, can be used in combination with an anti-human CD3 antibody in accordance with the invention described herein. Examples of such agents include, but are not limited to antibody fragments, GLP-1 analogs or derivatives, GLP-1 agonists (e.g. exendin-4; exentatide), amylin analogs or derivatives, insulin, dermatological agents for rashes and swellings (e.g., phototherapy (i.e., ultraviolet B radiation), photochemotherapy (e.g., PUVA) and topical agents such as emollients, salicylic acid, coal tar, topical steroids, topical corticosteroids, topical vitamin D3 analogs (e.g., calcipotriene), tazarotene, and topical retinoids), anti-inflammatory agents (e.g., corticosteroids (e.g., prednisone and hydrocortisone), glucocorticoids, steroids, non-steroidal anti-inflammatory drugs (e.g., aspirin, ibuprofen, diclofenac, and COX-2 inhibitors), beta-agonists, anticholinergic agents and methyl xanthines), immunomodulatory agents (e.g., small organic molecules, a T cell receptor modulators, cytokine receptor modulators, T cell depleting agents, cytokine antagonists, monokine antagonists, lymphocyte inhibitors, or anti-cancer agents), gold injections, sulphasalazine, penicillamine, anti-angiogenic agents (e.g., angiostatin, TNF-α antagonists (e.g., anti-TNFα antibodies), and endostatin), dapsone, psoralens (e.g., methoxalen and trioxsalen), anti-malarial agents (e.g., hydroxychloroquine), anti-viral agents, and antibiotics (e.g., erythomycin and penicillin). Any immunomodulatory agent well-known to one of skill in the art may also be used in the methods and compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments of the invention, an immunomodulatory agent modulates one aspect of the immune response. In other embodiments, an immunomodulatory agent modulates more than one aspect of the immune response. In a preferred embodiment of the invention, the administration of an immunomodulatory agent to a subject inhibits or reduces one or more aspects of the subject's immune response capabilities. In a specific embodiment of the invention, the immunomodulatory agent inhibits or suppresses the immune response in a subject. In accordance with the invention, an immunomodulatory agent is not an anti-human CD3 antibody. In certain embodiments, an immunomodulatory agent is not an anti-inflammatory agent. In other embodiments, an immunomodulatory agent is not a CD3 binding molecule. In yet other embodiments, an immunomodulatory agent is not OKT3 or a derivative thereof.

An immunomodulatory agent may be selected to interfere with the interactions between the T helper subsets (TH1 or TH2) and B cells to inhibit neutralizing antibody formation. An immunomodulatory agent may be selected to inhibit the interaction between TH11 cells and CTLs to reduce the occurrence of CTL-mediated killing. An immunomodulatory agent may be selected to alter (e.g., inhibit or suppress) the proliferation, differentiation, activity and/or function of the $CD4^+$ and/or $CD8^+$ T cells. For example, antibodies specific for T cells can be used as immunomodulatory agents to deplete, or alter the proliferation, differentiation, activity and/or function of $CD4^+$ and/or $CD8^+$ T cells.

In specific embodiments, the anti-human CD3 binding molecule is co-administered with a cytokine antagonist. In other embodiments, the anti-human CD3 binding molecule is co-administered with an anti-IL-2 antibody, such as, for example, daclizumab, basiliximab or MT204 (Micromet) or other IL-2 inhibitor, such as but not limited to rapamycin, cyclosporine, or tacrolimus.

In other embodiments, the anti-human CD3 binding molecule is administered in conjunction with an antigen targeted by anti-islet cell antibodies such as, but not limited to GAD (such as GAD 65), insulin, IA-2, ICA512 or other antigen against which autoantibodies are found in type 1 diabetes patients. Such co-administration may lead to tolerance to the islet cell antigens.

In a preferred embodiment, proteins, polypeptides or peptides (including antibodies) that are utilized as prophylactic, therapeutic or immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

In accordance with the invention, one or more prophylactic, therapeutic or immunomodulatory agents are administered to a subject with an inflammatory or autoimmune disease prior to, subsequent to, or concomitantly with the therapeutic and/or prophylactic agents of the invention. Preferably, one or more prophylactic, therapeutic or immunomodulatory agents are administered to a subject with an inflammatory or autoimmune disease to reduce or inhibit one or more symptoms of the disease or aspects of the immune response as necessary. Any technique well-known to one skilled in the art can be used to measure one or more aspects of the immune response in a particular subject, and thereby determine when it is necessary to administer an immunomodulatory agent to said subject. In a preferred embodiment, an absolute lymphocyte count of approximately 500 cells/$mm^3$, preferably 600 cells/$mm^3$, more 700 cells/$mm^3$, and most preferably 800 cells/$mm^3$ is maintained in a subject. In another preferred embodiment, a subject with an autoimmune or inflammatory disorder is not administered an immunomodulatory agent if their absolute lymphocyte count is 500 cells/$mm^3$ or less, S50 cells/$mm^3$ or less, 600 cells/$mm^3$ or less, 650 cells/$mm^3$ or less, 700 cells/$mm^3$ or less, 750 cells/$mm^3$ or less, or 800 cells/$mm^3$ or less.

In a preferred embodiment, one or more prophylactic, therapeutic or immunomodulatory agents are administered to a subject with an inflammatory or autoimmune disease so as to transiently reduce or inhibit one or more aspects of the disease or of the immune response. Such a transient inhibition or reduction of one or more aspects of the disease or of the immune system can last for hours, days, weeks, or months. Preferably, the transient inhibition or reduction in one or more aspects of the disease or of the immune response last for a few hours (e.g., 2 hours, 4 hours, 6 hours, 8 hours, 12 hours, 14 hours, 16 hours, 18 hours, 24 hours, 36 hours, or 48 hours), a few days (e.g., 3 days, 4 days, 5 days, 6 days, 7 days, or 14 days), or a few weeks (e.g., 3 weeks, 4 weeks, 5 weeks or 6 weeks). The transient reduction or inhibition of one or more aspects of the disease or of the immune response enhances the prophylactic and/or therapeutic capabilities of an anti-CD3 antibody.

In accordance with the invention, one or more prophylactic, therapeutic or immunomodulatory agents are administered to a subject with type 1 diabetes, or a predisposition thereto, prior to, subsequent to, or concomitantly with the therapeutic and/or prophylactic agents of the invention. Such methods may be employed to treat, prevent, delay the onset of, slow the progression of or ameliorate one or more symptoms of type 1 diabetes.

In specific embodiments, the present invention provides a method for preventing, treating, managing, delaying the onset of, slowing the progression of, or ameliorating one or more symptoms of type 1 diabetes, said method comprising administering to said subject a prophylactically or therapeutically effective amount of one or more anti-human CD3 antibodies and a prophylactically or therapeutically effective amount of insulin. In one embodiment, the present invention provides a method for preventing, treating, managing, delaying the onset of, slowing the progression of, or ameliorating one or more symptoms of type 1 diabetes, said method comprising administering to said subject a prophylactically or therapeutically effective amount of one or more anti-human CD3 antibodies and a prophylactically or therapeutically effective amount of GLP1 or GLP1 analog. In one embodiment, the present invention provides a method for preventing, treating, managing, delaying the onset of, slowing the progression of, or ameliorating one or more symptoms of type 1 diabetes, said method comprising administering to said subject a prophylactically or therapeutically effective amount of one or more anti-human CD3 antibodies and a prophylactically or therapeutically effective amount of exendin-4 or analog thereof. In one embodiment, the present invention provides a method for preventing, treating, managing, delaying the onset of, slowing the progression of, or ameliorating one or more symptoms of type 1 diabetes, said method comprising administering to said subject a prophylactically or therapeutically effective amount of one or more anti-human CD3 antibodies and a prophylactically or therapeutically effective amount of amylin or an analog thereof. In another embodiment, the present invention provides a method for preventing, treating, managing, delaying the onset of, slowing the progression of, or ameliorating one or more symptoms of type 1 diabetes, said method comprising administering to said subject a prophylactically or therapeutically effective amount of the humanized anti-human CD3 antibody OKT3 and a prophylactically or therapeutically effective amount of insulin.

Nucleic acid molecules encoding proteins, polypeptides, or peptides with prophylactic, therapeutic or immunomodulatory activity or proteins, polypeptides, or peptides with prophylactic, therapeutic or immunomodulatory activity can be administered to a subject with an autoimmune disorder in accordance with the methods of the invention. Further, nucleic acid molecules encoding derivatives, analogs, fragments or variants of proteins, polypeptides, or peptides with prophylactic, therapeutic or immunomodulatory activity, or derivatives, analogs, fragments or variants of proteins, polypeptides, or peptides with prophylactic, therapeutic or immunomodulatory activity can be administered to a subject in accordance with the methods of the invention. Preferably, such derivatives, analogs, variants and fragments retain the prophylactic, therapeutic or immunomodulatory activity of the full-length wild-type protein, polypeptide, or peptide.

Proteins, polypeptides, or peptides that can be used as prophylactic, therapeutic or immunomodulatory agents can be produced by any technique well-known in the art or described herein. See, e.g., Chapter 16 Ausubel et al. (eds.), 1999, Short Protocols in Molecular Biology, Fourth Edition, John Wiley & Sons, NY, which describes methods of producing proteins, polypeptides, or peptides, and which is incorporated herein by reference in its entirety. Antibodies which can be used as prophylactic, therapeutic or immunomodulatory agents can be produced by, e.g., methods described in U.S. Pat. No. 6,245,527 and in Harlow and Lane Antibodies: A Laboratory Manual, Cold Spring Harbor Laboratory Press, Cold Spring Harbor, N.Y., 1988, which are incorporated herein by reference in their entirety. Preferably, agents that are commercially available and known to function as prophylactic, therapeutic or immunomodulatory agents are used in the compositions and methods of the invention. The prophylactic, therapeutic or immunomodulatory activity of an agent can be determined in vitro and/or in vivo by any technique well-known to one skilled in the art, including, e.g., by CTL assays, proliferation assays, and immunoassays (e.g. ELISAs) for the expression of particular proteins such as co-stimulatory molecules and cytokines.

The combination of one or more anti-human CD3 antibodies and one or more prophylactic or therapeutic agents other than anti-human CD3 antibodies produces a better prophylactic or therapeutic effect in a subject than either treatment alone. In certain embodiments, the combination of an anti-human CD3 antibody and a prophylactic or therapeutic agent other than an anti-human CD3 antibody achieves a 20%, 25%, 30%, 35%, 40%, 45%, 50%, 55%, 60%, 65%, 70%, 75%, 80%, 85%, 90%, 95% or 98% better prophylactic or therapeutic effect in a subject with the autoimmune disorder, or predisposition thereto, than either treatment alone. In particular embodiments, the combination of one or more anti-CD3 antibodies and a prophylactic or therapeutic agent other than an anti-CD3 antibody achieves a 20%, preferably a 25%, 30%, 35%, 40%, 45%, 50%, 55%, 60%, 65%, 70%, 75%, 80%, 85%, 90%, 95% or 98% greater reduction in the inflammation of a particular organ, tissue or joint in a subject with an inflammatory disorder or an autoimmune disorder which is associated with inflammation than either treatment alone. In other embodiments, the combination of one or more anti-CD3 antibodies and one or more prophylactic or therapeutic agents other than anti-CD3 antibodies has an a more than additive effect or synergistic effect in a subject with an autoimmune or inflammatory disorder.

The combination therapies of the invention enable lower dosages of anti-human CD3 antibodies and/or less frequent administration of anti-human CD3 antibodies to a subject with an autoimmune disorder to achieve a prophylactic or therapeutic effect. The combination therapies of the invention enable lower dosages of the prophylactic or therapeutic agents utilized in conjunction with anti-human CD3 antibodies and/or less frequent administration of such prophylactic or therapeutic agents to achieve a prophylactic or therapeutic effect.

The prophylactic or therapeutic agents of the combination therapies of the present invention can be administered concomitantly, concurrently or sequentially. The prophylactic or therapeutic agents of the combination therapies of the present invention can also be cyclically administered. Cycling therapy involves the administration of a first prophylactic or therapeutic agent for a period of time, followed by the administration of a second prophylactic or therapeutic agent for a period of time and repeating this sequential administration, i.e., the cycle, in order to reduce the development of resistance to one of the agents, to avoid or reduce the side effects of one of the agents, and/or to improve the efficacy of the treatment.

5.2.8.1 Methods of Use of Combination Therapy

In a specific embodiment, the present invention provides a method for preventing, treating, managing, or ameliorating one or more symptoms associated with an autoimmune or inflammatory disorder in a subject, said method comprising administering to said subject one or more anti-CD3 antibodies and one or more prophylactic or therapeutic agents other than anti-CD3 antibodies. In a preferred embodiment, the present invention provides a method for preventing, treating, managing, or ameliorating one or more symptoms associated with an autoimmune or inflammatory disorder in a subject, said method comprising administering to said subject one or more anti-CD3 antibodies and one or more prophylactic or therapeutic agents other than anti-CD3 antibodies, wherein at least one of the anti-CD3 antibodies is a humanized OKT3.

The present invention provides methods of preventing, treating, managing or ameliorating one or more symptoms associated with an autoimmune or inflammatory disorder in a subject, said methods comprising administering to said subject one or more anti-CD3 antibodies and one or more prophylactic, therapeutic or immunomodulatory agents. Preferably, the immunomodulatory agents are not administered to a subject with an autoimmune or inflammatory disorder whose absolute lymphocyte count is less than 500 cells/mm$^3$, less than 550 cells/mm$^3$, less than 600 cells/mm$^3$, less than 650 cells/mm$^3$, less than 700 cells/mm$^3$, less than 750 cells/mm$^3$, less than 800 cells/mm$^3$, less than 850 cells/mm$^3$ or less than 900 cells/mm$^3$. Thus, in a preferred embodiment, prior to or subsequent to the administration of one or more dosages of one or more immunomodulatory agents to a subject with an autoimmune or inflammatory disorder, the absolute lymphocyte count of said subject is determined by techniques well-known to one of skill in the art, including, e.g., flow cytometry or trypan blue counts.

In one embodiment, the present invention provides a method for preventing, treating, managing or ameliorating one or more symptoms associated with diabetes, said method comprising administering to said subject a prophylactically or therapeutically effective amount of one or more anti-CD3 antibodies and a prophylactically or therapeutically effective amount of insulin. In one embodiment, the present invention provides a method for preventing, treating, managing or ameliorating one or more symptoms associated with diabetes, said method comprising administering to said subject a prophylactically or therapeutically effective amount of one or more anti-CD3 antibodies and a prophylactically or therapeutically effective amount of GLP 1 or GLP 1 analog. In one embodiment, the present invention provides a method for preventing, treating, managing or ameliorating one or more symptoms associated with diabetes, said method comprising administering to said subject a prophylactically or therapeutically effective amount of one or more anti-CD3 antibodies and a prophylactically or therapeutically effective amount of exendin-4 or analog thereof. In one embodiment, the present invention provides a method for preventing, treating, managing or ameliorating one or more symptoms associated with diabetes, said method comprising administering to said subject a prophylactically or therapeutically effective amount of one or more anti-CD3 antibodies and a prophylactically or therapeutically effective amount of amylin or an analog thereof. In another embodiment, the present invention provides a method for preventing, treating, managing or ameliorating one or more symptoms associated with diabetes, said method comprising administering to said subject a prophylactically or therapeutically effective amount of the humanized anti-CD3 antibody OKT3 and a prophylactically or therapeutically effective amount of insulin. In another embodiment, the present invention provides a method for preventing, treating, managing or ameliorating one or more symptoms associated with psoriasis, said method comprising administering to said subject a prophylactically or therapeutically effective amount of one or more anti-CD3 antibodies and a prophylactically or therapeutically effective amount of methotrexate. In another embodiment, the present invention provides a method for preventing, treating, managing or ameliorating one or more symptoms associated with psoriasis in a subject, said method comprising administering to said subject a prophylactically or therapeutically effective amount of the humanized anti-CD3 antibody OKT3 and a prophylactically or therapeutically effective amount of methotrexate.

5.3 Pharmaceutical Compositions

The present invention provides compositions for the treatment, prophylaxis, and amelioration of one or more symptoms associated with an autoimmune disorder. In a specific embodiment, a composition comprises one or more anti-human CD3 antibodies. In another embodiment, a composition comprises one or more nucleic acid molecules encoding the heavy and light chains of one or more anti-human CD3 antibodies.

In a specific embodiment, a composition comprises an anti-human CD3 antibody, wherein said anti-human CD3 antibody is a human or humanized monoclonal antibody, preferably modified to reduce binding of the Fc domain to Fc receptors and, thereby, reduce toxicity of the antibody. In yet another preferred embodiment, a composition comprises humanized OKT3, an analog, derivative, fragment thereof that immunospecifically binds to CD3 polypeptides, preferably OKT3γ1 (ala-ala), but may also include ChAglyCD3 (TRX4™), or HUM291 (visilizumab; NUVION™).

In a preferred embodiment, a composition of the invention is a pharmaceutical composition. Such compositions comprise a prophylactically or therapeutically effective amount of one or more anti-human CD3 antibodies, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like (See, for example, *Handbook of Pharmaceutical Excipients*, Arthur H. Kibbe (ed., 2000, which is incorporated by reference herein in its entirety), Am. Pharmaceutical Association, Washington, D.C. The composition, if desired, can also contain minor amounts of wetting or emulsifying agents, or pH buffering agents. These compositions can take the form of solutions, suspensions, emulsion, tablets, pills, capsules, powders, sustained release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the pharmaceutical compositions are sterile and in suitable form for administration to a subject, preferably an animal subject, more preferably a mammalian subject, and most preferably a human subject.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an anti-human CD3 antibody, care must be taken to use materials to which the anti-human CD3 antibody does not absorb.

In another embodiment, the composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the composition can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the lungs, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention or fragments thereof. See, e.g., U.S. Pat. No. 4,526,938; PCT publication WO 91/05548; PCT publication WO 96/20698; Ning et al., 1996, Radiotherapy & Oncology 39:179-189; Song et al., 1995, PDA Journal of Pharmaceutical Science & Technology 50:372-397; Cleek et al., 1997, Pro. Int'l. Symp. Control. Rel. Bioact. Mater. 24:853-854; and Lam et al., 1997, Proc. Int'l. Symp. Control Rel. Bioact. Mater. 24:759-760, each of which is incorporated herein by reference in its entirety.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of, e.g., an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, $4^{th}$ ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well-known in the art.

If the compositions of the invention are to be administered intranasally, the compositions can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

If the compositions of the invention are to be administered orally, the compositions can be formulated orally in the form of, e.g., tablets, capsules, cachets, gelcaps, solutions, suspensions and the like. Tablets or capsules can be prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated for slow release, controlled release or sustained release of a prophylactic or therapeutic agent(s).

The compositions of the invention may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In specific embodiments, the invention provides dosage forms that permit administration of the anti-human CD3 antibodies continuously over a period of hours or days (e.g., associated with a pump or other device for such delivery), for example, over a period of 1 hour, 2 hours, 3 hours, 4 hours, 6 hours, 8 hours, 10 hours, 12 hours. 16 hours, 20 hours, 24 hours, 30 hours, 36 hours, 4 days, 5 days, 7 days, 10 days or 14 days. In other specific embodiments, the invention provides dosage forms that permit administration of a continuously increasing dose, for example, increasing from 51 µg/m²/day to 826 µg/m²/day over a period of 24 hours, 30 hours, 36 hours, 4 days, 5 days, 7 days, 10 days or 14 days.

The compositions of the invention may also be formulated in rectal compositions such as suppositories or retention enemas, e.g., containing conventional suppository bases such as cocoa butter or other glycerides.

In addition to the formulations described previously, the compositions of the invention may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In particular, the invention provides that one or more anti-human CD3 antibodies, or pharmaceutical compositions of the invention is packaged in a hermetically sealed container such as an ampoule or sachette indicating the quantity of the agent. In one embodiment, one or more of the anti-human CD3 antibodies, or pharmaceutical compositions of the invention is supplied as a dry sterilized lyophilized powder or water free concentrate in a hermetically sealed container and can be reconstituted, e.g., with water or saline to the appropriate concentration for administration to a subject. Preferably, one or more of the anti-human CD3 antibodies, or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents, or pharmaceutical compositions of the invention should be stored at between 2 and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the anti-human CD3 antibodies, or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

In a preferred embodiment, the invention provides that the composition of the invention is packaged in a hermetically sealed container such as an ampoule or sachette indicating the quantity of anti-human CD3 antibody.

The compositions may, if desired, be presented in a pack or dispenser device that may contain one or more unit dosage forms containing the active ingredient. The pack may for example comprise metal or plastic foil, such as a blister pack.

Generally, the ingredients of the compositions of the invention are derived from a subject that is the same species origin or species reactivity as recipient of such compositions. Thus, in a preferred embodiment, human or humanized antibodies are administered to a human patient for therapy or prophylaxis.

The amount of the composition of the invention which will be effective in the treatment, prevention or amelioration of one or more symptoms associated with an autoimmune diabetes disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

5.4 Characterization of Anti-CD3 Therapeutic or Prophylactic Utility

CD3 binding molecules may be characterized in a variety of ways. In particular, CD3 binding molecules may be assayed for the ability to immunospecifically bind to a CD3 polypeptide. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223, 409), on plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310) (each of these references is incorporated herein in its entirety by reference). CD3 binding molecules that have been identified to immunospecifically bind to a CD3 polypeptide can then be assayed for their specificity and affinity for a CD3 polypeptide.

CD3 binding molecules may be assayed for immunospecific binding to a CD3 polypeptide and cross-reactivity with other polypeptides by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the CD3 binding molecule of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the CD3 binding molecule of interest to immunoprecipitate a particular antigen can be assessed by, e.g., western blot analysis. One of skill in the art would be knowledgeable as to the parameters that can be modified to increase the binding of the CD3 binding molecule to a CD3 polypeptide and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with CD3 binding molecule of interest (e.g., an antibody of interest) diluted in blocking buffer, washing the membrane in washing buffer, blocking the membrane with an antibody (which recognizes the CD3 binding molecule) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the CD3 polypeptide. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing CD3 polypeptide, coating the well of a 96 well microtiter plate with the CD3 polypeptide, adding the CD3 binding molecule of interest conjugated to a detectable compound such as an enzymatic substrate (e.g., horseradish peroxidase or alkaline phosphatase) to the well and incubating for a period of time, and detecting the presence of the CD3 polypeptide. In ELISAs the CD3 binding molecule of interest does not have to be conjugated to a detectable compound; instead, an antibody (which recognizes the CD3 binding molecule of interest) conjugated to a detectable compound may be added to the well. Further, instead of coating the well with the CD3 polypeptide, the CD3 binding molecule may be coated to the well. In this case, an antibody conjugated to a detectable compound may be added following the addition of the CD3 polypeptide to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of a CD3 binding molecule to a CD3 polypeptide and the off-rate of an CD3 binding molecule-CD3 polypeptide interaction can be determined by competitive binding assays. One example of a competitive binding assay is a radioimmunoassay comprising the incubation of labeled CD3 polypeptide (e.g., $^{3}$H or $^{125}$I) with the CD3 binding molecule of interest in the presence of increasing amounts of unlabeled CD3 polypeptide, and the detection of the CD3 binding molecule bound to the labeled CD3 polypeptide. The affinity of a CD3 binding molecule for a CD3 polypeptide and the binding off-rates can be determined from the data by scatchard plot analysis. Competition with a second CD3 binding molecule can also be determined using radioimmunoassays. In this case, a CD3 polypeptide is incubated with a CD3 binding molecule conjugated to a labeled compound (e.g., $^{3}$H or $^{125}$I) in the presence of increasing amounts of a second unlabeled CD3 binding molecule.

In a preferred embodiment, BIAcore kinetic analysis is used to determine the binding on and off rates of CD3 binding molecules to a CD3 polypeptide. BIAcore kinetic analysis comprises analyzing the binding and dissociation of a CD3 polypeptide from chips with immobilized CD3 binding molecules on their surface.

The CD3 binding molecules, in particular anti-human CD3 antibodies, and compositions of the invention can also be assayed for their ability to modulate T cell activation. T cell activation can be determined by measuring, e.g., changes in the level of expression of cytokines and/or T cell activation markers. Techniques known to those of skill in the art, including, but not limited to, immunoprecipitation followed by western blot analysis, ELISAs, flow cytometry, Northern blot analysis, and RT-PCR can be used to measure the expression cytokines and T cell activation markers. In a preferred embodiment, a CD3 binding molecule or composition of the invention is tested for its ability to induce the expression of IFN-γ and/or IL-2.

The anti-CD3 antibodies, and compositions of the invention can also be assayed for their ability to induce T cell signaling. The ability of an anti-CD3 antibody or a composition of the invention induce T cell signaling can be assayed, e.g., by kinase assays and electrophoretic shift assays (EMSAs).

The anti-CD3 antibodies, and compositions of the invention can be tested in vitro or in vivo for their ability to modulate T cell proliferation. For example, the ability of an anti-CD3 antibody or a composition of the invention to modulate T cell proliferation can be assessed by, e.g., $^{3}$H-thymidine incorporation, trypan blue cell counts, and fluorescence activated cell sorting (FACS).

The anti-human CD3 antibodies, and compositions of the invention can be tested in vitro or in vivo for their ability to induce cytolysis. For example, the ability of an anti-CD3 antibody or a composition of the invention to induce cytolysis can be assessed by, e.g., $^{51}$Cr-release assays.

The anti-CD3 antibodies, and compositions of the invention can be tested in vitro or in vivo for their ability to mediate the depletion of peripheral blood T cells. For example, the ability of an anti-CD3 antibody or a composition of the invention to mediate the depletion of peripheral blood T cells can be assessed by, e.g., measuring T cell counts using flow cytometry analysis.

The anti-CD3 antibodies, and compositions of the invention can be tested in vivo for their ability to mediate peripheral blood lymphocyte counts. For example, the ability of an anti-CD3 antibody or a composition of the invention to mediate peripheral blood lymphocyte counts can be assessed by, e.g., obtaining a sample of peripheral blood from a subject, separating the lymphocytes from other components of peripheral blood such as plasma using, e.g., a Ficoll gradient, and counting the lymphocytes using trypan blue.

5.4.1 Characterization of Immunoglobulin Molecules with Variant Fc Regions

In preferred embodiments, characterization of molecules comprising variant Fc regions with altered FcγR affinities (e.g., null FcγR binding) are done with one or more biochemical based assays, preferably in a high throughput manner. The one or more biochemical assays can be any assay known in the art for identifying Fc-FcγR interaction, i.e., specific binding of an Fc region to an FcγR, including, but not limited to, an ELISA assay, surface plasmon resonance assays, immunoprecipitation assay, affinity chromatography, and equilibrium dialysis. The functional based assays can be any assay known in the art for characterizing one or more FcγR mediated effector cell functions. Comparison of antibodies with altered Fc regions of the invention to control antibodies provides a measure of the extent of decrease or elimination of Fc-FcγR interaction. Non-limiting examples of effector cell functions that can be used in accordance with the methods of the invention, include but are not limited to, antibody-dependent cell mediated cytotoxicity (ADCC), antibody-dependent phagocytosis, phagocytosis, opsonization, opsonophagocytosis, cell binding, rosetting, C1q binding, and complement dependent cell mediated cytotoxicity. In preferred embodiments, characterization of molecules comprising variant Fc regions with altered FcγR affinities (e.g., null FcR binding) are done with one or more biochemical based assays in combination or in parallel with one or more functional based assays, preferably in a high throughput manner.

In some embodiments, characterization of molecules comprising variant Fc regions with altered FcγR affinities (e.g., null FcγR binding) comprise: characterizing the binding of the molecule comprising the variant Fc region to a FcγR (one or more), using a biochemical assay for determining Fc-FcγR interaction, preferably, an ELISA based assay followed by comparison of the results to the results of the same assay obtained with a control, i.e. non-modified, antibody. Once the molecule comprising a variant Fc region has been characterized for its interaction with one or more FcγRs and determined to have null binding to one or more FcγRs, by at least one biochemical based assay, e.g., an ELISA assay, the molecule maybe engineered into a complete immunoglobulin, using standard recombinant DNA technology methods known in the art, and the immunoglobulin comprising the variant Fc region expressed in mammalian cells for further biochemical characterization. The immunoglobulin into which a variant Fc region of the invention is introduced (e.g., replacing the Fc region of the immunoglobulin) can be any immunoglobulin including, but not limited to, polyclonal antibodies, monoclonal antibodies, bispecific antibodies, multi-specific antibodies, humanized antibodies, and chimeric antibodies. In preferred embodiments, a variant Fc region is introduced into an immunoglobulin specific for the CD3 complex associated with the human TCR.

The variant Fc regions, preferably in the context of an immunoglobulin, can be further characterized using one or more biochemical assays and/or one or more functional assays, preferably in a high throughput manner. In some alternate embodiments, the variant Fc regions are not introduced into an immunoglobulin and are further characterized using one or more biochemical based assays and/or one or more functional assays, preferably in a high throughput manner. The one or more biochemical assays can be any assay known in the art for identifying Fc-FcγR interactions, including, but not limited to, an ELISA assay, and surface plasmon resonance-based assay for determining the kinetic parameters of Fc-FcγR interaction, e.g., BIAcore assay. The one or more functional assays can be any assay known in the art for characterizing one or more FcγR mediated effector cell function as known to one skilled in the art or described herein. In specific embodiments, the immunoglobulins comprising the variant Fc regions are assayed in an ELISA assay for binding to one or more FcγRs, e.g., FcγRIIIA, FcγRIIA, FcγRIIA; followed by one or more ADCC assays. In some embodiments, the immunoglobulins comprising the variant Fc regions are assayed further using a surface plasmon resonance-based assay, e.g., BIAcore. For further a detailed discussion of characterization of immunoglobulins comprising variant Fc regions see U.S. Pat. Appl. Pub. No. 2005/0064514 A1 and U.S. Pat. Appl. Pub. No. 20050037000 A1.

The immunoglobulin comprising the variant Fc regions may be analyzed at any point using a surface plasmon based resonance based assay, e.g., BIAcore, for defining the kinetic parameters of the Fc-FcγR interaction, using methods known to those of skill in the art.

In most preferred embodiments, the immunoglobulin comprising the variant Fc regions is further characterized in an animal model for interaction with an FcγR. Preferred animal models for use in the methods of the invention are, for example, transgenic mice expressing human FcγRs, e.g., any mouse model described in U.S. Pat. No. 5,877,397, which is incorporated herein by reference in its entirety. Transgenic mice for use in the methods of the invention include, but are not limited to, nude knockout FcγRIIIA mice carrying human FcγRIIIA; nude knockout FcγRIIIA mice carrying human FcγRIIA; nude knockout FcγRIIIA mice carrying human FcγRIIB and human FcγRIIIA; nude knockout FcγRIIIA mice carrying human FcγRIIB and human FcγRITA.

5.4.2 In Vitro and In Vivo Characterization

Several aspects of the pharmaceutical compositions or the anti-CD3 antibodies of the invention are preferably tested in vitro, in a cell culture system, and in an animal model organism, such as a rodent animal model system, for the desired therapeutic activity prior to use in humans. For example, assays which can be used to determine whether administration of a specific pharmaceutical composition is indicated, include cell culture assays in which a patient tissue sample is grown in culture, and exposed to or otherwise contacted with a pharmaceutical composition, and the effect of such composition upon the tissue sample is observed. The tissue sample can be obtained by biopsy from the patient. This test allows the identification of the therapeutically most effective tumor-targeted bacteria and the therapeutically most effective therapeutic molecules) for each individual patient. In various specific embodiments, in vitro assays can be carried out with representative cells of cell types involved in an autoimmune or inflammatory disorder (e.g., T cells), to determine if a pharmaceutical composition of the invention has a desired effect upon such cell types.

In accordance with the invention, clinical trials with human subjects need not be performed in order to demonstrate the prophylactic and/or therapeutic efficacy of anti-CD3 antibodies. In vitro and animal model studies using anti-CD3 antibodies can be extrapolated to humans and are sufficient for demonstrating the prophylactic and/or therapeutic utility of said anti-CD3 antibodies.

Anti-CD3 antibodies can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, CD3 binding molecules are tested in a mouse model system. Such model systems are widely used and well-known to the skilled artisan. CD3 binding molecules can be administered repeatedly. Several aspects of the procedure may vary. Said aspects include the temporal regime of administering CD3 binding molecules, and whether such agents are administered separately or as an admixture.

The anti-inflammatory activity of anti-CD3 antibodies or pharmaceutical compositions of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of anti-CD3 antibodies or pharmaceutical compositions of invention. The following are some assays provided as examples and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety. A collagen-induced arthritis (CIA) is an animal model for the human autoimmune disease rheumatoid arthritis (RA) (Trenthorn et al., 1977, J. Exp. Med. 146:857). This disease can be induced in many "species by the administration of heterologous type II collagen (Courtenay et al., 1980, Nature 283:665; and Cathcart et at, 1986, Lab. Invest. 54:26). With respect to animal models of arthritis see, in addition, e.g., Holmdahl, R., 1999, Curr. Biol. 15:R528-530.

Additionally, animal models for inflammatory bowel disease can also be used to assess the efficacy of the anti-CD3 antibodies or pharmaceutical compositions of invention (Kim et al., 1992, Scand. J. Gastroentrol. 27:529-537; Strober, 1985, Dig. Dis. Sci. 30(12 Suppl):3S-1OS). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for asthma can also be used to assess the efficacy of anti-CD3 antibodies or pharmaceutical compositions of invention. An example of one such model is the marine adoptive transfer model in which aeroallergen provocation of TH 1 or TH2 recipient mice results in TH effector cell migration to the airways and is associated with an intense neutrophilic (TH 1) and eosinophilic (TH2) lung mucosal inflammatory response (Cohn et al., 1997, J. Exp. Med. 1861737-1747).

Animal models for autoimmune disorders can also be used to assess the efficacy of anti-CD3 antibodies or pharmaceutical compositions of invention. Animal models for autoimmune disorders such as type 1 diabetes, thyroid autoimmunity, systemic lupus eruthematosus, and glomerulonephritis have been developed (Bluestone et al., 2004, PNAS 101: 14622-14626; Flanders et al., 1999, Autoimmunity 29:235-246; Krogh et al., 1999, Biochimie 81:511-515; Foster, 1999, Semin. Nephrol. 19:12-24).

The efficacy of anti-CD3 antibodies or pharmaceutical compositions of invention can also be tested in such autoimmune disorder models as an experimental allergic encephalomyelitis (EAE) model. EAE is an experimental autoimmune disease of the central nervous system (CNS) (Zamvil et al, 1990, Ann. Rev, Immunol. 8:579) and is a disease model for the human autoimmune condition, multiple sclerosis (MS). EAE is an example of a cell-mediated autoimmune disorder that is mediated via T cells. EAE is readily induced in mammalian species by immunizations of myelin basic protein (MBP) purified from the CNS or an encephalitogenic proteolipid (PLP). SJL/J mice are a susceptible strain of mice (H-2u) and, upon induction of EAE, these mice develop an acute paralytic disease and an acute cellular infiltrate is identifiable within the CNS. EAE spontaneously develops in MBP1-17 peptide-specific T cell receptor (TCR) transgenic mice (TgMBP+) of a RAG-1-deficient background (Lafulle et al., 1994, Cell 78:399).

Further, any assays known to those skilled in the art can be used to evaluate anti-CD3 antibodies or the pharmaceutical compositions disclosed herein for autoimmune and/or inflammatory diseases.

The toxicity and/or efficacy of anti-CD3 antibodies or pharmaceutical compositions of invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Anti-CD3 antibodies that exhibit large therapeutic indices are preferred. While anti-CD3 antibodies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of anti-human CD3 antibodies for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Efficacy in preventing or treating an autoimmune disorder may be demonstrated, e.g., by detecting the ability of a anti-human CD3 antibodies or composition of the invention to reduce one or more symptoms of the autoimmune disorder, to reduce mean absolute lymphocyte counts, to decrease T cell activation, to decrease T cell proliferation, to reduce cytokine production, or to modulate one or more particular cytokine profiles. Efficacy in treating diabetes may be demonstrated, e.g. by detecting the ability of a anti-human CD3 antibodies or composition of the invention to reduce one or more symptoms of diabetes, to preserve the C-peptide response to MMTT, to reduce the level HA1 or HA1c, to reduce the daily requirement for insulin, or to decrease T cell activation in pancreatic islet tissue. Efficacy in preventing or treating an inflammatory disorder may be demonstrated, e.g., by detecting, the ability of a an anti-CD3 antibody to reduce one or more symptoms of the inflammatory disorder, to decrease T cell activation, to decrease T cell proliferation, to modulate one or more cytokine profiles, to reduce cytokine production, to reduce inflammation of a joint, organ or tissue or to improve quality of life.

Changes in inflammatory disease activity may be assessed through tender and swollen joint counts, patient and physician global scores for pain and disease activity, and the ESRI-CRP. Progression of structural joint damage may be assessed by quantitative scoring of X-rays of hands, wrists, and feet (Sharp method). Changes in functional status in humans with inflammatory disorders may be evaluated using the Health Assessment Questionnaire (HAQ), and quality of life changes are assessed with the SF-36.

5.5 Methods of Monitoring Lymphocyte Counts and Percent Binding

The effect of one or more doses of one or more anti-human CD3 antibodies or composition on peripheral blood lymphocyte counts can be monitored/assessed using standard techniques known to one of skill in the art. Peripheral blood lymphocytes counts in a mammal can be determined by, e.g., obtaining a sample of peripheral blood from said mammal, separating the lymphocytes from other components of peripheral blood such as plasma using, e.g., Ficoll-Hypaque (Pharmacia) gradient centrifugation, and counting the lymphocytes using trypan blue. Peripheral blood T cell counts in mammal can be determined by, e.g., separating the lymphocytes from other components of peripheral blood such as plasma using, e.g., a use of Ficoll-Hypaque (Pharmacia) gradient centrifugation, labeling the T cells with an antibody directed to a T cell antigen such as CD2, CD3, CD4, and CD8 which is conjugated to FITC or phycoerythrin, and measuring the number of T cells by FACS. Further, the effect on a particular subset of T cells (e.g., $CD2^+$, $CD4^+$, $CD8^+$, $CD4^+RO^+$, $CD8^+RO^+$, $CD4^+RA^+$, or $CD8^+RA^+$) cells can be determined using standard techniques known to one of skill in the art such as FACS.

The percentage of CD3 polypeptides expressed by peripheral blood lymphocytes bound by anti-CD3 antibodies prior or after, or both prior to and after the administration of one or more doses of anti-CD3 antibodies can be assessed using standard techniques known to one of skill in the art. The percentage of CD3 polypeptides expressed by peripheral blood T cells bound by anti-CD3 antibodies can be determined by, e.g., obtaining a sample of peripheral blood from a mammal, separating the lymphocytes from other components of peripheral blood such as plasma using, e.g., Ficoll-Hypaque (Pharmacia) gradient centrifugation, and labeling the T cells with an anti-CD3 binding molecule antibody other than that of the invention conjugated to FITC and an antibody directed to a T cell antigen such as CD3, CD4 or CD8 which is conjugated to phycoerythrin, and determining the number of T cells labeled with anti-CD3 binding molecule antibody relative to the number of T cells labeled with an antibody directed to a T cell antigen using FACS.

5.6 Methods of Producing Antibodies

Antibodies that immunospecifically bind to a CD3 polypeptide can be produced by any method known in the art for the synthesis of antibodies, in particular, by chemical synthesis or preferably, by recombinant expression techniques.

Polyclonal antibodies that immunospecifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T cell Hybridomas 563 681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a CD3 antigen and once an immune response is detected, e.g., antibodies specific for a CD3 antigen (preferably, CD3 ε antigen) are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting an antibody of the invention wherein, preferably, the hybridoma is generated by fusing splenocytes isolated from a mouse immunized with a CD3 antigen with myeloma cells and then screening the hybridomas resulting from the fusion for hybridoma clones that secrete an antibody able to bind to a CD3 antigen (preferably, CD3ε antigen).

Antibody fragments which recognize specific CD3 antigens (preferably, CD3ε antigen) may be generated by any technique known to those of skill in the art. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli and the E. coli is infected with helper phage. Phage used in these methods are typically filamentous phage including fd and M13 and the VH and VL domains are usually recombinantly fused to either the phage gene HI or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/01134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569, 825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos.

5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fabc, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments of the invention include, but are not limited to, C-kappa and C-gamma-1 (nG1m) described in Johnson et al. (1997) *J. Infect. Dis.* 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%. Humanized antibody can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16): 10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

5.7 Polynucleotides Encoding Antibodies

The invention provides polynucleotides comprising a nucleotide sequence encoding an antibody that immunospecifically binds to a CD3 polypeptide. The invention also encompasses polynucleotides that hybridize under high stringency, intermediate or lower stringency hybridization conditions, e.g., as defined supra, to polynucleotides that encode an antibody of the invention.

The polynucleotides may be obtained, and the nucleotide sequence of the polynucleotides determined, by any method known in the art. The nucleotide sequence of antibodies immunospecific for a CD3 polypeptide can be obtained, e.g., from the literature or a database such as GenBank. Since the amino acid sequences of, e.g., humanized OKT3 is known, nucleotide sequences encoding these antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an antibody that specifically binds to a CD3 polypeptide. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

5.8 Recombinant Expression of Molecules of the Invention

Once a nucleic acid sequence encoding molecules of the invention (i.e., antibodies) has been obtained, the vector for the production of the molecules may be produced by recombinant DNA technology using techniques well known in the art. Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY).

An expression vector comprising the nucleotide sequence of a molecule identified by the methods of the invention (i.e., an antibody) can be transferred to a host cell by conventional techniques (e.g., electroporation, liposomal transfection, and calcium phosphate precipitation) and the transfected cells are then cultured by conventional techniques to produce the molecules of the invention. In specific embodiments, the expression of the molecules of the invention is regulated by a constitutive, an inducible or a tissue, specific promoter. In specific embodiments the expression vector is pMGX1303 (FIG. 3).

The host cells used to express the molecules identified by the methods of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, *Gene* 45:101; Cockett et al., 1990, *Bio/Technology* 8:2).

A variety of host-expression vector systems may be utilized to express the molecules identified by the methods of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the molecules identified by the methods of the invention; yeast (e.g., *Saccharomyces Pichia*) transformed with recombinant yeast expression vectors containing sequences encoding the molecules identified by the methods of the invention; insect cell systems infected with recombinant virus expression vectors (e.g., baculovirus) containing the sequences encoding the molecules identified by the methods of the invention; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules identified by the methods of the invention; or mammalian cell systems (e.g., COS, CHO, BHK, 293, 293T, 3T3 cells, lymphatic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited to, the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, *Cell* 11: 223), hypoxanthine-guanine phosphoribosyltransferase (Szybalska & Szybalski, 1992, *Proc. Natl. Acad. Sci. USA* 48: 202), and adenine phosphoribosyltransferase (Lowy et al., 1980, *Cell* 22: 817) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78: 1527); gpt, which confers resistance to mycophenolic acid (Mulligan & Berg, 1981, *Proc. Natl. Acad. Sci. USA* 78: 2072); neo, which confers resistance to the aminoglycoside G-418 *Clinical Pharmacy* 12: 488-505; Wu and Wu, 1991, 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY; Colberre-Garapin et al., 1981, *J. Mol. Biol.* 150:1; and hygro, which confers resistance to hygromycin (Santerre et al., 1984, *Gene* 30:147).

The expression levels of an antibody of the invention can be increased by vector amplification (for a review, see Bebbington and Hentschel, *The use of vectors based on gene amplification for the expression of cloned genes in mammalian cells in DNA cloning*, Vol. 3 (Academic Press, New York, 1987). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once a molecule of the invention (i.e., antibodies) has been recombinantly expressed, it may be purified by any method known in the art for purification of polypeptides or antibodies, for example, by chromatography (e.g., ion exchange, affinity, particularly by affinity for the specific antigen after Protein A, and sizing column chromatography), centrifugation, differential solubility, or by any other standard technique for the purification of polypeptides or antibodies.

6. EXAMPLES 6.1 Anti-CD3 Monoclonal Antibody Therapy for Type 1 Patients

Patients:

Forty patients with Type 1 diabetes are recruited for participation according to the following criteria: between 7 and 20 years of age, within 6 weeks of diagnosis according to the American Diabetes Association criteria, and confirmation of the presence of anti-GAD65, anti-ICA512, and/or anti-insulin autoantibodies. The patients remain under the care of their personal physicians during the course of the study.

Eligible patients are randomly assigned to a control group and an anti-human CD3 antibody treatment group. After randomization, blood samples are drawn to establish baseline HA1c levels, a pretreatment C-peptide response to a MMTT is established and a pretreatment FPIR to IGTT is performed. Patients in both groups are hospitalized to receive either a 6-day course treatment of the anti-human CD3 monoclonal antibody hOKT3γ1 (ala-ala) or placebo. The antibody is administered intravenously in the following dosage: 17 µg/m$^2$ on day 1, 34.3 µg/m$^2$ on day 2, 69 µg/m$^2$ on day 3, 137.6 µg/m$^2$ on day 4, and 275.3 µg/m$^2$ on days 5 and 6. Alternatively, antibody may be administered intravenously in the following dosage: 1.6 µg/kg/day on day 1; 3.2 µg/kg/day on day 2; 6.5 µg/kg/day on day 3; 13 µg/kg/day on day 4; and 26 µg/kg/day on days 5 through 14. In dose escalation studies, the treatment may be, e.g., 1.42 µg/kg/day on day 1; 5.7 µg/kg/day on day 2; 11 µg/kg/day on day 3; 26 µg/kg/day on day 4; and 45.4 µg/kg/day on days 5 through 14. In subsequent studies, the therapy is altered to increase dosage and/or decrease the time course of treatment. For example, in subsequent studies patients may be administered a 4 day treatment: 6.4 µg/kg/day on day 1; 13 µg/kg/day on day 2, and 26 µg/kg/day on days 3 and 4; during additional dose escalation studies, the treatment may be 8 µg/kg/day on day 1; 16 µg/kg/day on day 2; and 32 µg/kg/day on days 3 and 4.

During initial studies the antibody dosage on the first three days of treatment is administered via slow infusion IV over 20 hours to monitor for adverse reactions. Subsequent studies will decrease the time of administration and/or split the dosage into 2 to 4 equal parts to be administered as bolus injections evenly distributed over the course of 12 hours. Patients in the control group undergo metabolic and immunologic tests but do no receive monoclonal antibodies. Patients are monitored throughout the study for immunosuppressive effects of the anti-human CD3 monoclonal antibody hOKT3γ1 (ala-ala).

Patients are monitored for 18 months after the treatment. β-cell function is determined every 6 months in the case of impaired glucose tolerance and every 12 months in case of normal glucose tolerance. Patients are allowed to have a normal diet, and remain under the care of their personal physician throughout the duration of the study. Immunological assays are repeated in intervals of 6 months. Insulin therapy will be given to the patients as directed by their personal physician.

β-cell function will be analyzed according to the changes of the C-peptide levels as measured by radioimmunoassay. After drawing samples for baseline C-peptide and glucose, the patients are given a mixed meal. The C-peptide levels are measured in samples drawn after 15, 30, 60, 90, 120, 150, 180, 210, and 240 min. The C-peptide response to the mixed-meal tolerance test (MMTT) is expressed as the total area under the response curve (AUC). A change in the response is considered to have occurred if the response differs by more than 7.5 percent from the response at study entry. The patients' C-peptide responses to MMTT are continuously monitored 6 months, 9 months, 12 months, 15 months and 18 months after the treatment. Alternatively, the β-cell function is assessed by FPIR to IGTT. Serum insulin levels are measured by a modification of a double-antibody radioimmunoassay method using monoiodinated tyrosine A14-labeled insulin (Amersham Pharmacia). FPIR is calculated as the sum of insulin levels at 1 and 3 minutes after a glucose load (0.5 g/kg). Glycosylated hemoglobin levels are measured by latex-agglutination inhibition test.

Immunological Monitoring:

The level of autoantibodies against GAD65, IA2/ICA512, and insulin are measured with radiobinding assays as known in the art (e.g., Woo et al., 2000, J. Immunol. Methods 244: 91-103). HLA-DQA and HLA-DQB genotyping are performed by direct sequencing of exon 2 polymorphisms after PCR amplification. The level of cytokines in serum after the administration of the monoclonal antibody is measured by enzyme-linked immunosorbent assay (ELISA). Production of anti-idiotype antibodies is monitored by ELISA assay using a plate bound hOKT3γ1 (ala-ala) or by flow cytometry to measure blockade of binding of hOKT3γ1 (ala-ala)-FITC to CD3.

Statistical Analysis:

Data analysis will be conducted on residual beta-cell function, autoantibody level, cytokine level, and glycosylated hemoglobin level. $\chi^2$ analysis will be performed to test the effect of drug treatment before and after drug administration. Comparison between the control group and the treatment group will be made with the Mann-Whitney U test.

6.2 Anti-CD3 Monoclonal Antibody Therapy in Subjects Predisposed to Type 1 Diabetes Patients:

Screening for subjects with predisposition for developing type 1 diabetes is based on first or second degree relationship with a diagnosed Type-1 diabetic; an impaired fasting glucose level; an impaired glucose response to OGTT; the presence of serum autoantibodies against GAD65, against 1A2/ICA512, and/or against insulin; or impaired insulin production after MMTT, OGTT, IGTT or two phase glucose clamp procedure as determined by C-peptide response or FPIR. Patients who have been diagnosed with type 1 diabetes according to the criteria established by the American Diabetes Association by a physician, or who otherwise meet said criteria, are excluded from this study.

Patients selected for the study are randomly placed into two equal-sized groups. Treatment protocols and clinical monitoring are as described in section 6.1. Additionally, antibody therapy may be adjusted relative to residual β-cell function, i.e., patients with more impaired β-cell function as determined by C-peptide response or FPIR will receive a higher total dose of anti-CD3 monoclonal antibody. For example, given two patients with C-peptide responses of 40 and 110 µmol/ml/240 min, the patient with impaired response will be given the higher of the two dosages tested, e.g., 1.42 µg/kg/day on day 1; 5.7 µg/kg/day on day 2; 11 µg/kg/day on day 3; 26 µg/kg/day on day 4; and 45.4 µg/kg/day on days 5 through 14.

Patients are monitored for 18 months after the treatment. β-cell function is determined every 6 months in the case of impaired glucose tolerance and every 12 months in case of normal glucose tolerance. Patients are allowed to have a normal diet, and remain under the care of their personal physician throughout the duration of the study. Immunological assays are repeated in intervals of 6 months. Insulin therapy will be given to the patients as directed by their personal physician.

6.3 Anti-CD3 Monoclonal Antibody Therapy in Multiple Sclerosis

Patients:

Patients with relapsing-remitting or secondary progressive multiple sclerosis, confirmed according to Poser and/or McDonald criteria are included in this study. Primary selection criteria also include at least two documented exacerbations in the last two year, age 18 or above, and baseline EDSS score between 0 and 5.

The selected patients are randomly assigned into a treatment group and a control group. Treatment protocols are as outlined in section 6.1. All patients remain under the care of their personal physician during the course of the study and receive equivalent neurological monitoring at equivalent time points.

Monitoring MS:

Neurological examinations are scheduled prior to treatment to establish baseline values, and subsequently every three months for a total of 36 months. The clinical assessment of patients is performed by two neurologists to monitor increases in the frequency, duration and/or severity of attacks, and/or to monitor for increases in EDSS score. Additionally, Gadolinium-enhanced MRI scans are performed to obtain baseline measurement of brain or spinal lesion number and/or volume and are repeated every three months for a total of 36 months. Patients remain under the care of personal physicians) during the course of the study. Patients with relapse are treated with Avonex and reexamined at monthly intervals for a period of at least 6 months.

An increase of one point on the EDSS which persists for at least two scheduled neurological examinations indicates progression of disability. The efficacy of the treatment is evaluated according to time to first relapse, relapse rate, and the accumulation of permanent physical disability. Comparison will be made between the treatment group and the control group. The extent and number of active lesions on MRI will also be recorded and compared.

7. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

---

What is claimed:

1. A method of treating, slowing the progression of, or ameliorating one or more symptoms of an autoimmune disorder in a patient diagnosed with said disorder, said method comprising administering to said patient a course of treatment with a therapeutically effective amount of an anti-human CD3 antibody wherein said antibody is humanized OKT3γ1 (ala-ala), wherein less than 9000 μg/m² is administered parenterally in total during said course of treatment;

wherein said treatment comprises a dosage regimen comprising doses of increasing amounts of said antibody on at least the initial 4 days of said course of treatment;

wherein said autoimmune disorder is rheumatoid arthritis; and wherein said patient is in early stages of the autoimmune disorder, during which, autoreactive cytotoxic T-lymphocytes are detected in synovial tissues but clinical symptoms of rheumatoid arthritis have not yet developed.

2. The method of claim 1, wherein the antibody is ChAglyCD3 or visilizumab.

3. The method of claim 1, wherein the dose on day 1 is approximately 51 μg/m², the dose on day 2 is approximately 103 μg/m², the dose on day 3 is approximately 207 μg/m², the dose on day 4 is approximately 413 μg/m², and the dose on subsequent days is approximately 826 μg/m².

4. The method of claim 1 wherein each dose of said antibody is administered intravenously in one infusion over a period of at least 18 hours.

5. The method of claim 4 in which said administration results in serum levels of free anti-human CD3 antibody that do not exceed 200 ng/ml.

6. The method of claim 1, in which said administration does not result in EBV-induced lymphoproliferative diseases or lymphocyte counts less than 1000 lymphocytes/μl serum.

7. The method of claim 1, further comprising redosing said patient with an additional round of said course of treatment.

8. The method of claim 7, wherein said patient had been administered a 6 to 20 day course of treatment with said anti-human CD3 antibodies prior to said additional round.

* * * * *

SEQUENCE LISTING

```
<160> NUMBER OF SEQ ID NOS: 13

<210> SEQ ID NO 1
<211> LENGTH: 107
<212> TYPE: PRT
<213> ORGANISM: Artificial Sequence
<220> FEATURE:
<223> OTHER INFORMATION: humanized light chain Okt3vl variable region

<400> SEQUENCE: 1

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
                100                 105

<210> SEQ ID NO 2
<211> LENGTH: 108
<212> TYPE: PRT
<213> ORGANISM: Artificial Sequence
<220> FEATURE:
<223> OTHER INFORMATION: Light Chain variable domain from REI

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
                20                  25                  30

Leu Asn Trp Tyr Gln Gln Thr Pro Gly Lys Ala Pro Lys Leu Leu Ile
            35                  40                  45

Tyr Glu Ala Ser Asn Leu Gln Ala Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95
```

```
Thr Phe Gly Gln Gly Thr Lys Leu Gln Ile Thr Arg
            100                 105
```

<210> SEQ ID NO 3
<211> LENGTH: 107
<212> TYPE: PRT
<213> ORGANISM: Artificial Sequence
<220> FEATURE:
<223> OTHER INFORMATION: gLA -light chain variable domain of a humanized Okt3vl

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Ile Thr Arg
            100                 105
```

<210> SEQ ID NO 4
<211> LENGTH: 107
<212> TYPE: PRT
<213> ORGANISM: Artificial Sequence
<220> FEATURE:
<223> OTHER INFORMATION: gLC -light chain variable domain of a humanized Okt3vl

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105
```

<210> SEQ ID NO 5
<211> LENGTH: 119
<212> TYPE: PRT
<213> ORGANISM: Artificial Sequence
<220> FEATURE:
<223> OTHER INFORMATION: humanized heavy chain Okt3vh variable region

<400> SEQUENCE: 5

```
Gln Val Gln Leu Gln Gln Ser Gly Ala Glu Leu Ala Arg Pro Gly Ala
1               5                   10                  15
```

```
Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115

<210> SEQ ID NO 6
<211> LENGTH: 126
<212> TYPE: PRT
<213> ORGANISM: Artificial Sequence
<220> FEATURE:
<223> OTHER INFORMATION: Light chain variable domain from KOL

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Ser Tyr
            20                  25                  30

Ala Met Tyr Trp Val Arg Gln Ala Pro Gly Lys Gly Leu Glu Trp Val
        35                  40                  45

Ala Ile Ile Trp Asp Asp Gly Ser Asp Gln His Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
            100                 105                 110

Pro Asp Tyr Trp Gly Gln Gly Thr Pro Val Thr Val Ser Ser
            115                 120                 125

<210> SEQ ID NO 7
<211> LENGTH: 119
<212> TYPE: PRT
<213> ORGANISM: Artificial Sequence
<220> FEATURE:
<223> OTHER INFORMATION: gH -heavy chain variable domain of a humanized
      Okt3vh

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ser Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Ala Tyr Ile Asn Pro Ser Arg Gly Tyr Thr Asn Tyr Asn Gln Lys Phe
    50                  55                  60
```

```
Lys Asp Arg Phe Thr Ile Ser Arg Asp Asn Ser Lys Asn Thr Leu Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115
```

<210> SEQ ID NO 8
<211> LENGTH: 119
<212> TYPE: PRT
<213> ORGANISM: Artificial Sequence
<220> FEATURE:
<223> OTHER INFORMATION: gHA -heavy chain variable domain of a humanized Okt3vh

<400> SEQUENCE: 8

```
Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
 50                  55                  60

Lys Asp Arg Phe Thr Ile Ser Thr Asp Lys Ser Lys Ser Thr Ala Phe
 65                  70                  75                  80

Leu Gln Met Asp Ser Leu Arg Pro Glu Asp Thr Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115
```

<210> SEQ ID NO 9
<211> LENGTH: 119
<212> TYPE: PRT
<213> ORGANISM: Artificial Sequence
<220> FEATURE:
<223> OTHER INFORMATION: gHG -heavy chain variable domain of a humanized Okt3vh

<400> SEQUENCE: 9

```
Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
 50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Cys Leu Asp Tyr Trp Gly Gln Gly
            100                 105                 110
```

Thr Pro Val Thr Val Ser Ser
        115

<210> SEQ ID NO 10
<211> LENGTH: 699
<212> TYPE: DNA
<213> ORGANISM: Artificial Sequence
<220> FEATURE:
<223> OTHER INFORMATION: Nucleotide sequence of the Light chain of a
      humanized OKT3

<400> SEQUENCE: 10

```
atgggatgga gctgtatcat cctcttcttg gtagcaacag ctacaggtgt ccactccgac      60
atccagatga cccagtctcc ttcttctctg tctgcttctg tcggagacag agtcacaatc     120
acatgttctg cttctagctc tgtctcttac atgaactggt accagcagac acctggaaag     180
gctcctaagc ggtggatcta cgacacatct aagctcgctt ctggagtccc ttctagattc     240
tctggttctg gctctggaac agactacaca ttcacaatct cttctctcca acctgaggac     300
atcgctacat actactgcca acagtggtct agcaatcctt tcacattcgg acagggaaca     360
aagctgcaga tcacaagaac tgtggcggcg ccgtctgtct tcatcttccc gccatctgat     420
gagcagttga aatctggaac tgcctctgtt gtgtgcctgc tgaataactt ctatcccaga     480
gaggccaaag tacagtggaa ggtggataac gccctccaat cgggtaactc ccaggagagt     540
gtcacagagc aggacagcaa ggacagcacc tacagcctca gcagcaccct gacgctgagc     600
aaagcagact acgagaaaca caaagtctac gcctgcgaag tcacccatca gggcctgagc     660
tcgcccgtca caaagagctt caacagggga gagtgttag                             699
```

<210> SEQ ID NO 11
<211> LENGTH: 232
<212> TYPE: PRT
<213> ORGANISM: Artificial Sequence
<220> FEATURE:
<223> OTHER INFORMATION: Amino acid sequence of the Light chain of a
      humanized OKT3

<400> SEQUENCE: 11

Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Ser Ser Ser Val
        35                  40                  45

Ser Tyr Met Asn Trp Tyr Gln Gln Thr Pro Gly Lys Ala Pro Lys Arg
    50                  55                  60

Trp Ile Tyr Asp Thr Ser Lys Leu Ala Ser Gly Val Pro Ser Arg Phe
65                  70                  75                  80

Ser Gly Ser Gly Ser Gly Thr Asp Tyr Thr Phe Thr Ile Ser Ser Leu
                85                  90                  95

Gln Pro Glu Asp Ile Ala Thr Tyr Tyr Cys Gln Gln Trp Ser Ser Asn
            100                 105                 110

Pro Phe Thr Phe Gly Gln Gly Thr Lys Leu Gln Ile Thr Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 12
<211> LENGTH: 1407
<212> TYPE: DNA
<213> ORGANISM: Artificial Sequence
<220> FEATURE:
<223> OTHER INFORMATION: Nucleotide sequence of the heavy chain of a
      humanized OKT3

<400> SEQUENCE: 12

```
atgggatgga gctgtatcat cctcttcttg gtagcaacag ctacaggtgt ccactcccag     60
gttcagctgg tgcagtctgg aggaggagtc gtccagcctg gaaggtccct gagactgtct    120
tgtaaggctt ctggatacac cttcactaga tacacaatgc actgggtcag acaggctcct    180
ggaaagggac tcgagtggat tggatacatt aatcctagca gaggttatac taactacaat    240
cagaaggtga aggacagatt cacaatttct agagacaatt ctaagaatac agccttcctg    300
cagatggact cactcagacc tgaggatacc ggagtctatt tttgtgctag atattacgat    360
gaccactact gtctggacta ctggggccaa gtaccccggt caccgtgagc tcagcttcc    420
accaagggcc catcggtctt ccccctggca ccctcctcca gagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660
tgcaacgtga atcacaagcc cagcaacacc aaggtggaca gaaagttga gcccaaatct    720
tgtgacaaaa ctcacacatg cccaccgtgc ccagcacctg aggccgcggg aggaccatca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                       1407
```

<210> SEQ ID NO 13
<211> LENGTH: 468
<212> TYPE: PRT
<213> ORGANISM: Artificial Sequence

```
<220> FEATURE:
<223> OTHER INFORMATION: Amino Acid sequence of the heavy chain of a
      humanized OKT3

<400> SEQUENCE: 13

Met Gly Trp Ser Cys Ile Ile Leu Phe Leu Val Ala Thr Ala Thr Gly
 1               5                  10                  15

Val His Ser Gln Val Gln Leu Val Gln Ser Gly Gly Val Val Gln
            20                  25                  30

Pro Gly Arg Ser Leu Arg Leu Ser Cys Lys Ala Ser Gly Tyr Thr Phe
            35                  40                  45

Thr Arg Tyr Thr Met His Trp Val Arg Gln Ala Pro Gly Lys Gly Leu
 50                      55                  60

Glu Trp Ile Gly Tyr Ile Asn Pro Ser Arg Gly Tyr Thr Asn Tyr Asn
 65              70                  75                      80

Gln Lys Val Lys Asp Arg Phe Thr Ile Ser Arg Asp Asn Ser Lys Asn
                85                  90                  95

Thr Ala Phe Leu Gln Met Asp Ser Leu Arg Pro Glu Asp Thr Gly Val
                100                 105                 110

Tyr Phe Cys Ala Arg Tyr Tyr Asp Asp His Tyr Cys Leu Asp Tyr Trp
                115                 120                 125

Gly Gln Gly Thr Pro Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
                210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

His Glu Asp Pro Glu Val Lys Phe Asn Trp Tyr Val Asp Gly Val Glu
                290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Asp Glu Leu Thr Lys Asn Gln Val
                370                 375                 380

Ser Leu Thr Cys Leu Val Lys Gly Phe Tyr Pro Ser Asp Ile Ala Val
```

-continued

```
                385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465
```